(12) United States Patent
Camphausen et al.

(10) Patent No.: US 9,469,676 B2
(45) Date of Patent: Oct. 18, 2016

(54) FC FUSION PROTEINS COMPRISING NOVEL LINKERS OR ARRANGEMENTS

(75) Inventors: Ray Camphausen, Wayland, MA (US); Amna Saeed-Kothe, West Roxbury, MA (US); Jonathan Davis, Auburndale, MA (US); Tracy S. Mitchell, Andover, MA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 153 days.

(21) Appl. No.: 14/111,327

(22) PCT Filed: Apr. 13, 2012

(86) PCT No.: PCT/US2012/033665
§ 371 (c)(1),
(2), (4) Date: Oct. 11, 2013

(87) PCT Pub. No.: WO2012/142515
PCT Pub. Date: Oct. 18, 2012

(65) Prior Publication Data
US 2014/0113370 A1    Apr. 24, 2014

Related U.S. Application Data

(60) Provisional application No. 61/475,004, filed on Apr. 13, 2011.

(51) Int. Cl.
| C07K 16/46 | (2006.01) |
|---|---|
| C07K 14/78 | (2006.01) |
| C07K 14/47 | (2006.01) |
| C07K 16/24 | (2006.01) |
| C07K 16/28 | (2006.01) |
| C07K 16/40 | (2006.01) |

(52) U.S. Cl.
CPC ............. *C07K 14/47* (2013.01); *C07K 14/78* (2013.01); *C07K 16/244* (2013.01); *C07K 16/2863* (2013.01); *C07K 16/40* (2013.01); *C07K 16/46* (2013.01); *C07K 2317/92* (2013.01); *C07K 2318/20* (2013.01); *C07K 2319/30* (2013.01)

(58) Field of Classification Search
CPC  C07K 16/2863; C07K 16/244; C07K 14/47; C07K 14/78; C07K 16/46; C07K 2316/52; C07K 2317/92; C07K 2318/00; C07K 2318/20; C07K 2319/30; C07K 2319/03; A61K 38/39

See application file for complete search history.

(56) References Cited

U.S. PATENT DOCUMENTS

| 5,310,875 A * | 5/1994 | Chang ............. A61K 47/48284 530/300 |
|---|---|---|
| 5,514,581 A | 5/1996 | Ferrari et al. |
| 5,545,620 A | 8/1996 | Wahl et al. |
| 5,624,821 A | 4/1997 | Winter et al. |
| 5,624,899 A * | 4/1997 | Bennett et al. ............ 514/7.5 |
| 5,641,648 A | 6/1997 | Ferrari et al. |
| 5,648,260 A | 7/1997 | Winter et al. |
| 5,731,168 A | 3/1998 | Carter et al. |
| 5,770,697 A | 6/1998 | Ferrari et al. |
| 5,792,742 A | 8/1998 | Gold et al. |
| 5,821,333 A | 10/1998 | Carter et al. |
| 6,018,030 A | 1/2000 | Ferrari et al. |
| 6,194,551 B1 | 2/2001 | Idusogie et al. |
| 6,207,446 B1 | 3/2001 | Szostak et al. |
| 6,214,553 B1 | 4/2001 | Szostak et al. |
| 6,258,558 B1 | 7/2001 | Szostak et al. |
| 6,261,804 B1 | 7/2001 | Szostak et al. |
| 6,277,375 B1 | 8/2001 | Ward |
| 6,281,344 B1 | 8/2001 | Szostak et al. |
| 6,462,189 B1 | 10/2002 | Koide |
| 6,518,018 B1 | 2/2003 | Szostak et al. |
| 6,737,056 B1 | 5/2004 | Presta |
| 6,818,418 B1 | 11/2004 | Lipovsek et al. |
| 7,115,396 B2 | 10/2006 | Lipovsek et al. |
| 7,317,091 B2 | 1/2008 | Lazar et al. |
| 7,556,925 B2 | 7/2009 | Koide et al. |
| 7,598,352 B2 | 10/2009 | Koide |
| 7,847,062 B2 | 12/2010 | Chen et al. |
| 7,858,739 B2 | 12/2010 | Chen et al. |
| 8,067,201 B2 | 11/2011 | Morin et al. |
| 8,101,720 B2 | 1/2012 | Lazar et al. |
| 8,221,765 B2 | 7/2012 | Camphausen et al. |
| 8,258,265 B2 | 9/2012 | Koide |

(Continued)

FOREIGN PATENT DOCUMENTS

| EP | 1266025 B1 | 11/2006 |
|---|---|---|
| EP | 1137941 B1 | 8/2009 |

(Continued)

OTHER PUBLICATIONS

Witkowski et al., Biochemistry 38(36): 11643-11650, 1999.*
Seffernick et al., J Bacteriol 183 (8): 2405-2410, Apr. 2001.*
Zuckier et al., Cancer Research 58: 3905-3908, 1998.*
International Preliminary Report on Patentability, PCT/US2012/033665, dated Oct. 15, 2013, pp. 1-5.
International Search Report and Written Opinion, PCT/US2012/033665, dated Oct. 25, 2012, pp. 1-9.

(Continued)

*Primary Examiner* — Phuong Huynh
(74) *Attorney, Agent, or Firm* — Nelson Mullins Riley & Scarborough LLP; Jane E. Remillard, Esq.; Christopher L. Frank

(57) ABSTRACT

The application provides Fc fusion proteins having novel arrangements. In one embodiment, the application provides Fc fusion proteins comprising a $^{10}$Fn3 domain. In another embodiment, the application provides Fc fusion proteins comprising linkers derived from the naturally occurring C-terminal tail regions of membrane bound or secretory immunoglobulins.

7 Claims, 32 Drawing Sheets

(56) References Cited

U.S. PATENT DOCUMENTS

| | | |
|---|---|---|
| 8,263,741 B2 | 9/2012 | Koide |
| 8,278,419 B2 | 10/2012 | Jacobs et al. |
| 8,293,482 B2 | 10/2012 | Jacobs et al. |
| 8,324,362 B2 | 12/2012 | Chen et al. |
| 8,343,501 B2 | 1/2013 | Emanuel et al. |
| 8,470,332 B2 | 6/2013 | Camphausen et al. |
| 8,524,244 B2 | 9/2013 | Camphausen et al. |
| 8,609,613 B2 | 12/2013 | Chen et al. |
| 8,728,483 B2 | 5/2014 | Camphausen et al. |
| 8,853,154 B2 | 10/2014 | Cload et al. |
| 8,933,199 B2 | 1/2015 | Cload et al. |
| 8,969,289 B2 | 3/2015 | Gosselin et al. |
| 8,993,265 B2 | 3/2015 | Cload et al. |
| 9,017,655 B2 | 4/2015 | Emanuel et al. |
| 2002/0019517 A1 | 2/2002 | Koide |
| 2002/0044944 A1* | 4/2002 | Nakamura ....... C07K 14/70578 424/185.1 |
| 2003/0170753 A1 | 9/2003 | Koide |
| 2003/0186385 A1 | 10/2003 | Koide |
| 2005/0136049 A1* | 6/2005 | Ledbetter .......... C07K 16/2818 424/132.1 |
| 2006/0210604 A1 | 9/2006 | Dadey et al. |
| 2006/0246059 A1 | 11/2006 | Lipovsek et al. |
| 2007/0082365 A1 | 4/2007 | Lipovsek et al. |
| 2007/0148126 A1 | 6/2007 | Chen et al. |
| 2008/0108798 A1 | 5/2008 | Lipovsek et al. |
| 2008/0220049 A1 | 9/2008 | Chen et al. |
| 2009/0176654 A1 | 7/2009 | Cappuccilli et al. |
| 2010/0144601 A1 | 6/2010 | Jacobs et al. |
| 2010/0152063 A1 | 6/2010 | Cappuccilli et al. |
| 2010/0273216 A1 | 10/2010 | Morin et al. |
| 2010/0298541 A1 | 11/2010 | Wu et al. |
| 2010/0322930 A1 | 12/2010 | Kolbinger et al. |
| 2011/0009323 A1 | 1/2011 | Gill |
| 2011/0021746 A1 | 1/2011 | Cappuccilli et al. |
| 2011/0038866 A1 | 2/2011 | Hastewell et al. |
| 2011/0123545 A1 | 5/2011 | Marsh et al. |
| 2011/0124527 A1 | 5/2011 | Cappuccilli et al. |
| 2011/0274623 A1 | 11/2011 | Jacobs |
| 2011/0275535 A1 | 11/2011 | Loew |
| 2012/0208704 A1 | 8/2012 | Loew et al. |
| 2012/0270797 A1 | 10/2012 | Wittrup et al. |
| 2013/0079243 A1 | 3/2013 | Diem et al. |
| 2013/0079280 A1 | 3/2013 | Baca et al. |
| 2013/0096019 A1 | 4/2013 | Jacobs et al. |
| 2013/0096058 A1 | 4/2013 | Baca et al. |
| 2013/0184212 A1 | 7/2013 | Camphausen et al. |
| 2013/0237684 A1 | 9/2013 | Koide |
| 2013/0267676 A1 | 10/2013 | Koide |
| 2013/0310317 A1 | 11/2013 | Camphausen et al. |
| 2014/0038893 A1 | 2/2014 | Camphausen et al. |
| 2014/0057807 A1 | 2/2014 | Loew et al. |
| 2014/0105896 A1 | 4/2014 | Cload et al. |
| 2014/0107020 A1 | 4/2014 | Cload et al. |
| 2014/0179896 A1 | 6/2014 | Chen et al. |
| 2014/0349929 A1 | 11/2014 | Camphausen et al. |
| 2015/0072919 A1 | 3/2015 | Cload et al. |
| 2015/0152147 A1 | 6/2015 | Gosselin et al. |
| 2015/0231211 A1 | 8/2015 | Cload et al. |

FOREIGN PATENT DOCUMENTS

| | | |
|---|---|---|
| EP | 2141243 A2 | 1/2010 |
| EP | 2385067 A1 | 11/2011 |
| EP | 2439212 A1 | 4/2012 |
| EP | 2379718 B1 | 3/2013 |
| WO | 88/07054 A1 | 9/1988 |
| WO | 88/07089 A1 | 9/1988 |
| WO | 94/29351 A2 | 12/1994 |
| WO | 96/27011 A1 | 9/1996 |
| WO | 96/32478 A1 | 10/1996 |
| WO | 97/34631 A1 | 9/1997 |
| WO | 98/31700 A1 | 7/1998 |
| WO | 98/56915 A2 | 12/1998 |
| WO | 99/51642 A1 | 10/1999 |
| WO | 99/51773 A1 | 10/1999 |
| WO | 00/34787 A1 | 6/2000 |
| WO | 00/42072 A2 | 7/2000 |
| WO | 01/58957 A2 | 8/2001 |
| WO | 01/64942 A1 | 9/2001 |
| WO | 02/04523 A2 | 1/2002 |
| WO | 02/06919 | 1/2002 |
| WO | 02/32925 A2 | 4/2002 |
| WO | WO0232925 * | 4/2002 |
| WO | 02/081497 A2 | 10/2002 |
| WO | 03/074679 A2 | 12/2003 |
| WO | 03/104418 A2 | 12/2003 |
| WO | 2004/016750 A2 | 2/2004 |
| WO | 2004/029207 A2 | 4/2004 |
| WO | 2004/035752 A2 | 4/2004 |
| WO | 2004/063351 A2 | 7/2004 |
| WO | 2004/074455 A2 | 9/2004 |
| WO | 2004/099249 A2 | 11/2004 |
| WO | 2005/040217 A2 | 5/2005 |
| WO | 2005/056764 A2 | 6/2005 |
| WO | 2005/070963 A1 | 8/2005 |
| WO | 2005/092925 A2 | 10/2005 |
| WO | 2006/020114 A2 | 2/2006 |
| WO | 2007/110205 A2 | 10/2007 |
| WO | 2008/012543 A1 | 1/2008 |
| WO | 2008/031098 A1 | 3/2008 |
| WO | 2008/066752 A2 | 6/2008 |
| WO | 2008/097497 A2 | 8/2008 |
| WO | 2008/131242 A1 | 10/2008 |
| WO | 2008/143954 A2 | 11/2008 |
| WO | 2009/006520 A1 | 1/2009 |
| WO | 2009/023184 A2 | 2/2009 |
| WO | 2009/025806 A2 | 2/2009 |
| WO | 2009/058379 A2 | 5/2009 |
| WO | 2009/073115 A1 | 6/2009 |
| WO | 2009/083804 A2 | 7/2009 |
| WO | 2009/086116 A2 | 7/2009 |
| WO | 2009/089004 A1 | 7/2009 |
| WO | WO 2009/083804 * | 7/2009 |
| WO | 2009/102421 A2 | 8/2009 |
| WO | 2009/133208 A1 | 11/2009 |
| WO | 2009/142773 A2 | 11/2009 |
| WO | 2010/051274 A2 | 5/2010 |
| WO | 2010/051310 A2 | 5/2010 |
| WO | 2010/060095 A1 | 5/2010 |
| WO | 2010/069913 A1 | 6/2010 |
| WO | 2010/093627 A2 | 8/2010 |
| WO | 2010/093771 A1 | 8/2010 |
| WO | 2010/129304 A2 | 11/2010 |
| WO | 2011/020033 A2 | 2/2011 |
| WO | 2011/035202 A2 | 3/2011 |
| WO | 2011/051333 A1 | 5/2011 |
| WO | 2011/051466 A1 | 5/2011 |
| WO | 2011/092233 A1 | 8/2011 |
| WO | 2011/100700 A2 | 8/2011 |
| WO | 2011/103105 A1 | 8/2011 |
| WO | 2011/130324 A1 | 10/2011 |
| WO | 2011/130328 A1 | 10/2011 |
| WO | 2011/130354 A1 | 10/2011 |
| WO | 2011/137319 A2 | 11/2011 |
| WO | 2011/140086 A2 | 11/2011 |
| WO | 2011/150133 A2 | 12/2011 |
| WO | 2012/016245 A2 | 2/2012 |
| WO | 2012/088006 A1 | 6/2012 |
| WO | 2012/142515 A2 | 10/2012 |
| WO | 2012/158678 A1 | 11/2012 |
| WO | 2012/158739 A1 | 11/2012 |
| WO | 2013/049275 A1 | 4/2013 |

OTHER PUBLICATIONS

Yeung et al., "Engineering Human IgG1 Affinity to Human Neonatal Fc Receptor: Impact of Affinity Improvement on Pharmacokinetics in Primates," 2010, J Immunol, 182:7663-7671.

Zheng et al., "IL-2 Receptor-Targeted Cytolytic IL-2/Fc Fusion Protein Treatment Blocks Diabetogenic Autoimmunity in Nonobese Diabetic Mice," J. Immunol. 163:4041-4048. (1999).

(56) References Cited

OTHER PUBLICATIONS

Baron, Martin et al., "H NMR Assignment and Secondary Structure of the Cell Adhesion Type III Module of Fibronectin," Biochemistry, vol. 31:2068-2073 (1992).
Bloom, L. et al., "FN3: a new protein scaffold reaches the clinic," Drug Discovery Today, Elsevier, vol. 14, No. 19-20, Oct. 1, 2009, pp. 949-955.
Campbell, Iain D. et al., "Building proteins with fibronectin type III modules. Fibronectin type III modules are versatile components of many proteins. Recent structures of module pairs show how these modules are joined together," Structure, vol. 2:333-337 (1994).
Canfield and Morrison, "The Binding Affinity of Human IgC for its High Affinity Fc Receptor Is Determined by Multiple Amino Acids in the Ch2 Domain and is Modulated by the Hinge Region," J. Exp. Med. 173:1483-1491 (1991).
Capon et al., "Designing CD4 immunoadhesins for AIDS therapy," (1989), Nature 337: 525-531.
Clarke, Jane et al., "Folding and Stability of a Fibronectin Type III Domain of Human Tenascin," J. Mol. Biol., vol. 270:771-778 (1997).
Connelly et al., "Mitogenic properties of a bispecific single-chain Fv-Ig fusion generated from CD2-specific mAb to distinct epitopes," International Immunology 10:1863-1872 (1998).
Copie, Valerie et al., "Solution Structure and Dynamics of Linked Cell Attachment Modules of Mouse Fibronectin Containing the RGD and Synergy Regions: Comparison with the Human Fibronectin Crystal Structure," J. Mol. Biol., vol. 277:663-682 (1998).
Dall'Acqua et al., "Increasing the Affinity of Human IgG1 for the Neonatal Dc Receptor: Biological Consequence," Journal of Immunology, 2002, 169:5171-5180.
Dall'Acqua et al., "Properties of Human IgG1s Engineered for Enhanced Binding to the Neonatal Fc Receptor (FcRn)," Journal of Biological Chemistry, (2006), 281:23514-23524.
Dickinson, Craig D. et al., "Crystal Structure of the Tenth Type III Cell Adhesion Module of Human Fibronectin," J. Mol. Biol., vol. 236:1079-1092 (1994).
Dickinson, Craig D. et al., "Crystals of the Cell-binding Module Module of Fibronectin Obtained from a Series of Recombinant Fragments Differing in length," J. Mol. Biol., vol. 238:123-127 (1994).
Duncan et al., "Localization of the Binding Site for the Human High-affinity Fc Receptor on IgG," Nature 332:563 (1988).
Ellison et al., "The nucleotide sequence of a human immunoglobulin C gamma1 gene," Nucl. Acids Res. 10:4071-4079 (1982).
Ely, Kathryn R. et al., "Common molecular scaffold for two unrelated RGD molecules," Protein Engineering, vol. 8 (8):823-827 (1995).
GenBank Accession No, P07589, 9 pages (1997).
GenBank Accession No. AAC48614.1, 2 pages, (1996).
GenBank Accession No. ABB78921, Lipovsek, D. et al., "New non-antibody proteins having an immunoglobulin fold, useful in research, therapeutic or diagnostic fields, particularly as scaffolds for designing proteins with specific properties, e.g. for binding any antigen of interest," 33 pages, (2005).
GenBank Accession No. CAA26536, Kornblihll, A.R. et al., "Isolation and characterizations of cDNA clones for human and bovine fibronectins," Proc. Natl. Acad. Sci. USA, vol. 80(11 ):3218-3222 (1983), 6 pages, (2005).
GenBank Accession No. X02761, Kornblihll, A.R. et al., "Isolation and characterization of cDNA clones for human and bovine fibronectins," Proc. Natl. Acad. Sci. USA, vol. 80(11 ):3218-3222 (1983), 4 pages, (2005).
Gillies S D et al., "Improving the Efficacy of Antibody-Interleukin 2 Fusion Protiens by Reducing Their Interaction with Fc Receptors," (1999) Cancer Res. 59:2159-2166.
Hinton et al., "An Engineered Human IgG1 Antibody with Longer Serum Half-Life," (2006) Journal of Immunology 176:346-356.

Hinton et al., "Engineered Human IgG Antitobies with Longer Serum Half-lives in Primates," (2004), J. Biol. Chem. 279 (8): 6213-6216.
Kaneko et al., "Anti-Inflammatory Activity of Immunoglobulin G Resulting from FC Sialylation," (2006), Science 313:670-673.
King, et al., "DNA vaccines with single-chain Fv fused to fragment C of tetanus toxin induce protective immunity against lymphoma and myeloma," Nat. Med. 4:1281-1286 (1998).
Koide, Akiko et al., "Stabilization of a Fibronectin Type III Domain by the Removal of Unfavorable Electrostatic Interactions on the Protein Surface," Biochemistry, vol. 40:10326-10333 (2001).
Koide, Shohei et al., "Directed Evolution of Fibronectin Type III Domain to Novel Ligand Binding Proteins," FASEB J., vol. 11 (9):A 1155, Abstract No. 1739 (1997).
Koide, Shohei et al., "Directed Evolution of Fibronectin Type III Domain to Novel Ligand Binding Proteins," FASEB J., vol. 11 (9):A837, Abstract No. M40 (1997).
Leahy, D.J. et al., "2.0 A Crystal Structure of a Four-Domain Segment of Human Fibronectin Encompassing the RGD Loop and Synergy Region," Cell, vol. 84(1):155-164 (1996).
Leahy, Daniel J. et al., "Structure of a Fibronectin Type III Domain from Tenascin Phased by MAD Analysis of the Selenomethionyl Protein," Science, vol. 258:987-991 (1992).
Lipovsek, Dasa et al., "In-vitro protein evolution by ribosome display and mRNA display," Journal of Immunological Methods, vol. 290:51-67 (2004).
Litvinovich, Sergei V. et al., "Interactions Between Type III Domains in the 110 kDa Cell-binding Fragments of Fibronectin," J. Mol. Biol., vol. 248:611-626 (1995).
Lombardo, A. et al., "Conformational flexibility and crystallization of tandemly linked type III modules of human fibronectin," Protein Science, vol. 5:1934-1938 (1996).
Main, Alison L. et al., "The Three-Dimensional Structure of the Tenth Type III Module of Fibronectin: An Insight into RGD-Mediated Interactions," Cell, vol. 71:671-678 (1992).
Mao et al., "Fibronectin fibrillogenesis, a cell-mediated matrix assembly process," Matrix Biology: Journal of the International Society for Matrix Biology 24(6):389-399 (2005).
Morgado et al., "Further evidence that BALB/c and C57BL/6 gamma 2a genes originate from two distinct isotypes," EMBO J. 8:3245-3251(1989).
Plaxco, Kevin W. et al., "A Comparison of the Folding Kinetics and Thermodynamics of Two Homologous Fibronectin Type III Modules," J. Mol. Biol.., vol. 270:763-770 (1997).
Plaxco, Kevin W. et al., "Rapid refolding of a proline-rich all-beta-sheet fibronectin type III module," Proc. Natl. Acad. Sci. USA, vol. 93:10703-10706 (1996).
Potts, Jennifer R. et al., "Fibronectin structure and assembly," Current Opinion in Cell Biology, vol. 6:648-655 (1994).
Potts, Jennifer R. et al., "Structure and Function of Fibronectin Modules," Matrix Biology, vol. 15:313-320 (1996).
Richards, Julie et al., "Engineered Fibronectin Type III Domain with a RGDWXE Sequence Binds with Enhanced Affinity and Specificity to Human alphavbeta3 Integrin," J. Mol. Biol.., vol. 326:1475-1488 (2003).
Scallon, et al., "Higher Levels of Sialylated Fc glycans in immunoglobulin G molecules can adversely Impact Functionality," 2007, Mol. Immunol. 44(7): 1524-1534.
Schreier et al., "Multiple differences between the nucleic acid sequences of the IgG2aa and IgG2ab alleles of the mouse," PNAS 78:4495-4499 (1981).
Shields et al, "High Resolution Mapping of the Binding Site on Human IgG1 for FcyRI, FcyRII, FcyRIII, and FcRn and Design of IgG1 Variants with Improved Binding to the FcyR," Journal of Biological Chemistry, 2001, 276(9):6591-6604.
Strohl, "Optimization of Fc-mediated effector functions of monoclonal antibodies," Current Opinion in Biotechnology (2009) 20:685-691.
Tao and Morrison, "Structural Features of Human Immunoglobulin G that Determine Isotype-specific Differences in Complement Activation," (1989) J. Immunol. 143:2595-2601.

(56) References Cited

OTHER PUBLICATIONS

Tao et al.,"Structural Features of Human Immunoglobulin G that Determine Isotype-specific Differences in Complement Activation," J. Exp. Med. 178:661-667 (1993).
Vuento and Vaheri, "Purification of Fibronectin from Human Plasma by Affinity Chromatography under Non-Denaturing Conditions," Biochem. J. 183:331-337 (1979).
Xu et al., "Directed Evolution of High-Affinity Antibody Mimics Using mRNA Display," Chemistry & Biology (2002) 9:933-942.
Fukui et al., "Duplicated immunoglobulin gamma 2a genes in wild mice," J. Mol. Cell. Immunol. 1:321 (1984).
U.S. Appl. No. 14/025,253, filed Sep. 12, 2013, Sharon Cload.
U.S. Appl. No. 14/275,542, filed May 12, 2014, Sharon Cload.
U.S. Appl. No. 14/632,436, filed Feb. 26, 2015, Sharon Cload.
U.S. Appl. No. 14/025,307, filed Sep. 12, 2013, Sharon Cload.
U.S. Appl. No. 14/481,641, filed Sep. 9, 2014, Sharon Cload.
U.S. Appl. No. 09/515,260, filed Feb. 29, 2000, Dasa Lipovsek.
U.S. Appl. No. 10/728,078, filed Dec. 3, 2003, Dasa Lipovsek.
U.S. Appl. No. 11/483,918, filed Jul. 7, 2006, Dasa Lipovsek.
U.S. Appl. No. 11/543,316, filed Oct. 3, 2006, Dasa Lipovsek.
U.S. Appl. No. 11/890,627, filed Aug. 6, 2007, Dasa Lipovsek.
U.S. Appl. No. 11/448,171, filed Jun. 5, 2006, Yan Chen.
U.S. Appl. No. 11/482,641, filed Jul. 7, 2006, Yan Chen.
U.S. Appl. No. 12/788,240, filed May 26, 2010, Yan Chen.
U.S. Appl. No. 13/552,398, filed Jul. 18, 2012, Yan Chen.
U.S. Appl. No. 14/071,069, filed Nov. 4, 2013, Yan Chen.
U.S. Appl. No. 12/312,725, filed Jan. 20, 2010, Ray Camphausen.
U.S. Appl. No. 13/892,418, filed May 13, 2013, Ray Camphausen.
U.S. Appl. No. 14/659,028, filed Mar. 16, 2015, Ray Camphausen.
U.S. Appl. No. 12/867,406, filed Oct. 29, 2010, Ray Camphausen.
U.S. Appl. No. 13/956,952, filed Aug. 1, 2013, Ray Camphausen.
U.S. Appl. No. 12/470,989, filed May 22, 2009, Ray Camphausen.
U.S. Appl. No. 13/533,382, filed Jun. 26, 2012, Ray Camphausen.
U.S. Appl. No. 14/229,415, filed Mar. 28, 2014, Ray Camphausen.
U.S. Appl. No. 12/625,217, filed Nov. 24, 2009, Stuart Emanuel.
U.S. Appl. No. 13/692,555, filed Dec. 3, 2012, Stuart Emanuel.
U.S. Appl. No. 14/664,290, filed Mar. 20, 2015, Stuart Emanuel.
U.S. Appl. No. 13/699,458, filed Mar. 28, 2013, Ray Camphausen.
U.S. Appl. No. 13/098,851, filed May 2, 2011, Michael L. Gosselin.
U.S. Appl. No. 14/552,823, filed Nov. 25, 2014, Michael L. Gosselin.

* cited by examiner

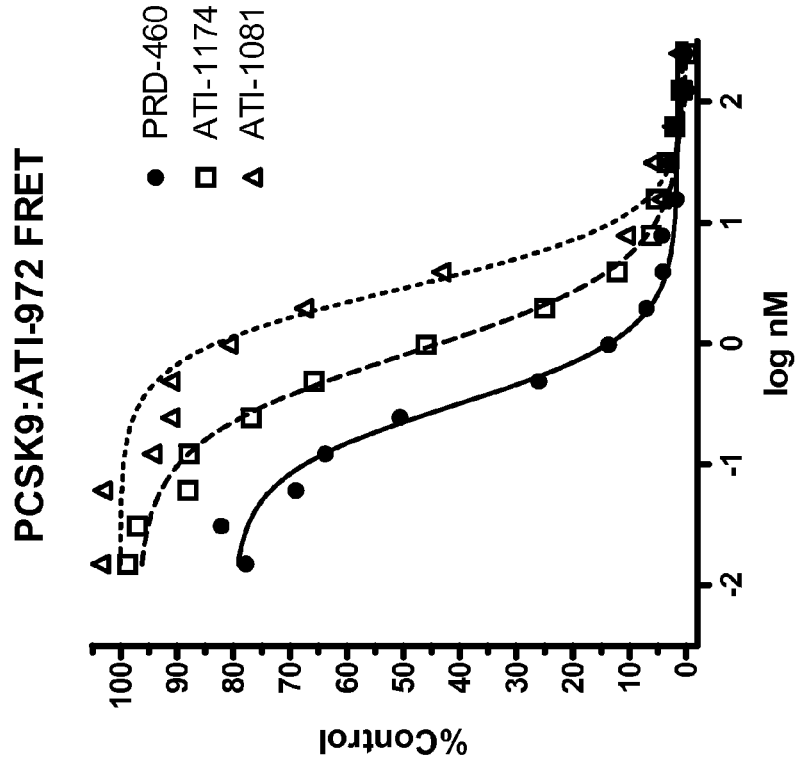
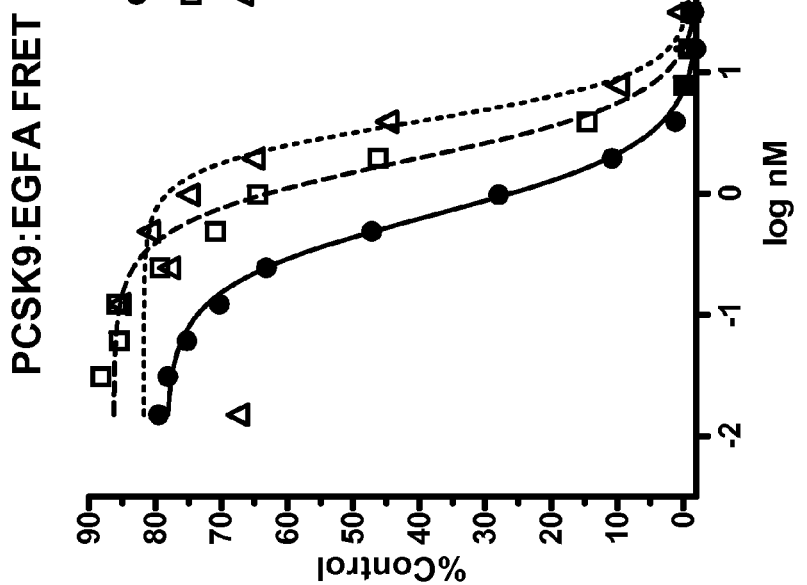
FIG. 1

FIG. 25

```
                              LC                         HC           HC
                              |                          |            |
     |216      218      220                              |    228     |  230|
Fc1  |Glu Pro  Lys Ser  Cys Asp Lys Thr His Thr Cys Pro Pro Cys Pro|
Fc4  | .   .   Arg  .   Ser  .   .   .   .   .   .   .   .   .   . |
Fc5  | .   .    .   .   Ser  .   .   .   .   .   .   .   .   .   . |
Fc6  | .   .    .   .   Ser  .   .   .   .   .   .   .   .   .   . |
Fc7  | .   .    .   .    .   .   .   .   .   .   .   .   .   .   . |
Fc8  | .   .   Arg  .   Ser  .   .   .   .   .   .   .   .   .   . |
Fc9  |                   |                                          |
Fc10 | .   .    .   .   Ser  .   .   .   .   .   .   .   .   .   . |
Fc11 | .   .    .   .   Ser  .   .   .   .   .   .   .   .   .   . |
Fc12 | .   .    .   .   Ser  .   .   .   .   .  Ser  .   .  Ser  . |
Fc13 | .   .    .   .   Ser  .   .   .   .   .  Ser  .   .  Ser  . |
Fc14 | .   .    .   .   Ser  .   .   .   .   .  Ser  .   .  Ser  . |
Fc15 | .  Ser   .  Tyr   -   -   -  Gly Pro Pro  .   .   .   .   . |
Fc16 | .   .    .   .   Ser  .   .   .   .   .   .   .   .   .   . |
Fc17 | .   .    .   .   Ser  .   .   .   .   .   .   .   .   .   . |
Fc18 | .   .    .   .   Ser  .   .   .   .   .   .   .   .   .   . |
Fc19 | .   .    .   .   Ser  .   .   .   .   .   .   .   .   .   . |
Fc21 | .   .    .   .   Ser  .   .   .   .   .  Ser  .   .  Ser  . |
Fc22 | .   .    .   .   Ser  .   .   .   .   .  Ser  .   .  Ser  . |
Fc23 | .   .    .   .   Ser  .   .   .   .   .   .   .   .   .   . |
     |                            <- hinge ->                      |

FcγRI    FcγRI
                     |  |      |
     |              234 235   237                        243      245
Fc1  |Ala Pro Glu  Leu Leu Gly Gly Pro Ser Val Phe Leu Phe Pro Pro
Fc4  | .   .   .   Ala Glu  .  Ala  .   .   .   .   .   .   .   .
Fc5  | .   .   .   Ala Glu  .  Ala  .   .   .   .   .   .   .   .
Fc6  | .   .   .   Ala Glu  .  Ala  .   .   .   .   .   .   .   .
Fc11 | .   .   .   Ala Glu  .  Ala  .   .   .   .   .   .   .   .
Fc12 | .   .   .   Ala Glu  .  Ala  .   .   .   .   .   .   .   .
Fc13 | .   .   .   Ala Glu  .  Ala  .   .   .   .   .   .   .   .
Fc15 | .   .   .   Phe  .   .   .   .   .   .   .   .   .   .   .
Fc17 | .   .   .    .   .   .   .   .   .   .   .   .  Ala  .   .
Fc19 | .   .   .   Ala Glu  .  Ala  .   .   .   .   .   .   .   .
Fc21 | .   .   .   Ala Glu  .  Ala  .   .   .   .   .   .   .   .
Fc23 | .   .   .   Ala Glu  .   .   .   .   .   .   .   .   .   .
     | CH2 ->

260
Fc1       Lys Pro Lys Asp Thr Leu Met Ile Ser Arg Thr Pro Glu Val Thr

275
Fc1       Cys Val Val Val Asp Val Ser His Glu Asp Pro Glu Val Lys Phe
Fc15       .   .   .   .   .   .   .  Gln  .   .   .   .   .  Gln  .

290
Fc1       Asn Trp Tyr Val Asp Gly Val Glu Val His Asn Ala Lys Thr Lys
```

FIG. 25 (continued)

```
                                      carbohydrate
                                           |
                                          297                              305
Fc1     Pro Arg Glu Glu Gln Tyr Asn Ser Thr Tyr Arg Val Val Ser Val
Fc7      .   .   .   .   .   .  Gln  .   .   .   .   .   .   .   .
Fc15     .   .   .   .   .  Phe  .   .   .   .   .   .   .   .   .
Fc19     .   .   .   .   .   .  Gln  .   .   .   .   .   .   .   .

320
Fc1     Leu Thr Val Leu His Gln Asp Trp Leu Asn Gly Lys Glu Tyr Lys

C1q
                                              330 331                     335
Fc1     Cys Lys Val Ser Asn Lys Ala Leu Pro Ala Pro Ile Glu Lys Thr
Fc4      .   .   .   .   .   .   .   .   .  Ser Ser  .   .   .   .
Fc5      .   .   .   .   .   .   .   .   .  Ser Ser  .   .   .   .
Fc6      .   .   .   .   .   .   .   .   .  Ser Ser  .   .   .   .
Fc12     .   .   .   .   .   .   .   .   .  Ser Ser  .   .   .   .
Fc13     .   .   .   .   .   .   .   .   .  Ser Ser  .   .   .   .
Fc15     .   .   .   .   .   .  Gly  .   .  Ser Ser  .   .   .   .
Fc19     .   .   .   .   .   .   .   .   .  Ser Ser  .   .   .   .
Fc21     .   .   .   .   .   .   .   .   .  Ser Ser  .   .   .   .
Fc23     .   .   .   .   .   .   .   .   .   .  Ser  .   .   .   .

|                                          350
Fc1     Ile Ser Lys Ala Lys|Gly Gln Pro Arg Glu Pro Gln Val Tyr Thr
                       <- CH2|CH3 ->

356     358                             365
Fc1     Leu Pro Pro Ser Arg Asp Glu Leu Thr Lys Asn Gln Val Ser Leu
Fc15     .   .   .   .  Gln Glu  .  Met  .   .   .   .   .   .   .
Fc16     .   .   .   .  Gln Glu  .  Met  .   .   .   .   .   .   .

380
Fc1     Thr Cys Leu Val Lys Gly Phe Tyr Pro Ser Asp Ile Ala Val Glu

395
Fc1     Trp Glu Ser Asn Gly Gln Pro Glu Asn Asn Tyr Lys Thr Thr Pro

410
Fc1     Pro Val Leu Asp Ser Asp Gly Ser Phe Phe Leu Tyr Ser Lys Leu
Fc13     .   .   .   .   .   .   .   .   .   .   .  Gly  .   .   .
Fc14     .   .   .   .   .   .   .   .   .   .   .  Gly  .   .   .
Fc15     .   .   .   .   .   .   .   .   .   .   .   .   .  Arg  .
Fc16     .   .   .   .   .   .   .   .   .   .   .   .   .  Arg  .
Fc21     .   .   .   .   .   .   .   .   .  Ala  .  Ala  .   .   .
Fc22     .   .   .   .   .   .   .   .   .  Ala  .  Ala  .   .   .
```

FIG. 25 (continued)

```
                                                                     425
Fc1     Thr Val Asp Lys Ser Arg Trp Gln Gln Gly Asn Val Phe Ser Cys
Fc15     .   .   .   .   .   .   .   .  Glu  .   .   .   .   .   .
Fc16     .   .   .   .   .   .   .   .  Glu  .   .   .   .   .   .

431         435             440
Fc1     Ser Val Met His Glu Ala Leu His Asn His Tyr Thr Gln Lys Ser
Fc18     .   .   .   .   .   .   .   .   .  Ala  .   .   .   .   .

446
Fc1     Leu Ser Leu Ser Pro Gly Lys ***
Fc6      .   .   .   .   .   .  ***
Fc15     .   .   .   .  Leu  .   .  ***
Fc16     .   .   .   .  Leu  .   .  ***
```

FIG. 26

```
                                                        HC
                                                        |
      |216       218 219 220         221                |
mFc1  |Glu Pro   Arg Gly Pro   -   Thr Ile Lys Pro Cys Pro Pro   -   -
mFc2  |  .   .    .   .  Ser   .    -   .   .   .   .   .   .    -   -
mFc3  |  .   .    .   .  Val   .   Ile   .  Gln Asn  .   .   .  Leu Lys
mFc4  |  .   .    .   .  Ser   .   Ile   .  Gln Asn  .   .   .  Leu Lys
      |                              <- hinge ->

HC              HC                    FcγRI+II
          |               |                        |
          |               |  230|                234 235         237
mFc1   -  Cys Lys  -     Cys Pro|Ala Pro Asn Leu Leu Gly Gly Pro Ser
mFc2   -   .   .  -      .   . |  .   .   .   .  Glu  .   .   .   .
mFc3  Glu  .  Pro Pro    .  Ala|  .   .  Asp  .   .   .   .   .   .
mFc4  Glu  .  Pro Pro    .  Ala|  .   .  Asp  .  Glu  .   .   .   .
                               |CH2 ->

245
mFc1  Val Phe Ile Phe Pro Pro Lys Ile Lys Asp Val Leu Met Ile Ser
mFc2   .   .   .   .   .   .   .   .   .   .   .   .   .   .   .
mFc3   .   .   .   .   .   .   .   .   .   .   .   .   .   .   .
mFc4   .   .   .   .   .   .   .   .   .   .   .   .   .   .   .

260
mFc1  Leu Ser Pro Ile Val Thr Cys Val Val Val Asp Val Ser Glu Asp
mFc2   .   .   .   .   .   .   .   .   .   .   .   .   .   .   .
mFc3   .   .   .  Met  .   .   .   .   .   .   .   .   .   .   .
mFc4   .   .   .  Met  .   .   .   .   .   .   .   .   .   .   .

275
mFc1  Asp Pro Asp Val Gln Ile Ser Trp Phe Val Asn Asn Val Glu Val
mFc2   .   .   .   .   .   .   .   .   .   .   .   .   .   .   .
mFc3   .   .   .   .   .   .   .   .   .   .   .   .   .   .   .
mFc4   .   .   .   .   .   .   .   .   .   .   .   .   .   .   .
```

FIG. 26 (continued)

```
                                                              carbohydrate
                                                                   |
                            290                                   297
mFc1    His Thr Ala Gln Thr Gln Thr His Arg Glu Asp Tyr Asn Ser Thr
mFc2     .   .   .   .   .   .   .   .   .   .   .   .   .   .   .
mFc3     .   .   .   .   .   .   .   .   .   .   .   .   .   .   .
mFc4     .   .   .   .   .   .   .   .   .   .   .   .   .   .   .

305
mFc1    Leu Arg Val Val Ser Ala Leu Pro Ile Gln His Gln Asp Trp Met
mFc2     .   .   .   .   .   .   .   .   .   .   .   .   .   .   .
mFc3     .   .   .   .   .   .   .   .   .   .   .   .   .   .   .
mFc4     .   .   .   .   .   .   .   .   .   .   .   .   .   .   .

C1q     C1q     C1q
                     |       |       |
                    318     320     322
mFc1    Ser Gly Lys Glu Phe Lys Cys Lys Val Asn Asn Lys Asp Leu Pro
mFc2     .   .   .  Ala  .  Ala  .  Ala  .   .   .   .   .   .   .
mFc3     .   .   .   .   .   .   .   .   .   .   .  Arg Ala  .   .
mFc4     .   .   .  Ala  .  Ala  .  Ala  .   .   .  Arg Ala  .   .

330 331         335                      |
mFc1    Ala Pro Ile Glu Arg Thr Ile Ser Lys Pro Lys|Gly Ser Val Arg
mFc2     .   .   .   .   .   .   .   .   .   .   . |  .   .   .   .
mFc3    Ser  .   .   .  Lys  .   .   .   .   .  Arg|  .  Pro  .   .
mFc4    Ser  .   .   .  Lys  .   .   .   .   .  Arg|  .  Pro  .   .
                                                <- CH2|CH3 ->

350
mFc1    Ala Pro Gln Val Tyr Val Leu Pro Pro Pro Glu Glu Glu Met Thr
mFc2     .   .   .   .   .   .   .   .   .   .   .   .   .   .   .
mFc3     .   .   .   .   .   .   .   .   .   .  Ala  .   .   .   .
mFc4     .   .   .   .   .   .   .   .   .   .  Ala  .   .   .   .

365
mFc1    Lys Lys Gln Val Thr Leu Thr Cys Met Val Thr Asp Phe Met Pro
mFc2     .   .   .   .   .   .   .   .   .   .   .   .   .   .   .
mFc3     .   .  Glu Phe Ser  .   .   .   .  Ile  .  Gly  .  Leu  .
mFc4     .   .  Glu Phe Ser  .   .   .   .  Ile  .  Gly  .  Leu  .
```

FIG. 26 (continued)

```
              380
mFc1   Glu Asp Ile Tyr Val Glu Trp Thr Asn Asn Gly Lys Thr Glu Leu
mFc2    .   .   .   .   .   .   .   .   .   .   .   .   .   .   .
mFc3   Ala Glu  .  Ala  .  Asp  .   .  Ser  .   .  Arg  .   .  Gln
mFc4   Ala Glu  .  Ala  .  Asp  .   .  Ser  .   .  Arg  .   .  Gln 395
mFc1   Asn Tyr Lys Asn Thr Glu Pro Val Leu Asp Ser Asp Gly Ser Tyr
mFc2    .   .   .   .   .   .   .   .   .   .   .   .   .   .   .
mFc3    .   .   .   .   .  Ala Thr  .   .   .   .   .   .   .   .
mFc4    .   .   .   .   .  Ala Thr  .   .   .   .   .   .   .   .

410
mFc1   Phe Met Tyr Ser Lys Leu Arg Val Glu Lys Lys Asn Trp Val Glu
mFc2    .   .   .   .   .   .   .   .   .   .   .   .   .   .   .
mFc3    .   .   .   .   .   .   .   .  Gln  .  Ser Thr  .  Glu Arg
mFc4    .   .   .   .   .   .   .   .  Gln  .  Ser Thr  .  Glu Arg 425
mFc1   Arg Asn Ser Tyr Ser Cys Ser Val Val His Glu Gly Leu His Asn
mFc2    .   .   .   .   .   .   .   .   .   .   .   .   .   .   .
mFc3   Gly Ser Leu Phe Ala  .   .   .   .   .   .   .   .   .   .
mFc4   Gly Ser Leu Phe Ala  .   .   .   .   .   .   .   .   .   .

440              446
mFc1   His His Thr Thr Lys Ser Phe Ser Arg Thr Pro Gly Lys
mFc2    .   .   .   .   .   .   .   .   .   .   .   .   .
mFc3    .  Leu  .   .   .  Thr Ile  .   .  Ser Leu  .   .
mFc4    .  Leu  .   .   .  Thr Ile  .   .  Ser Leu  .   .
```

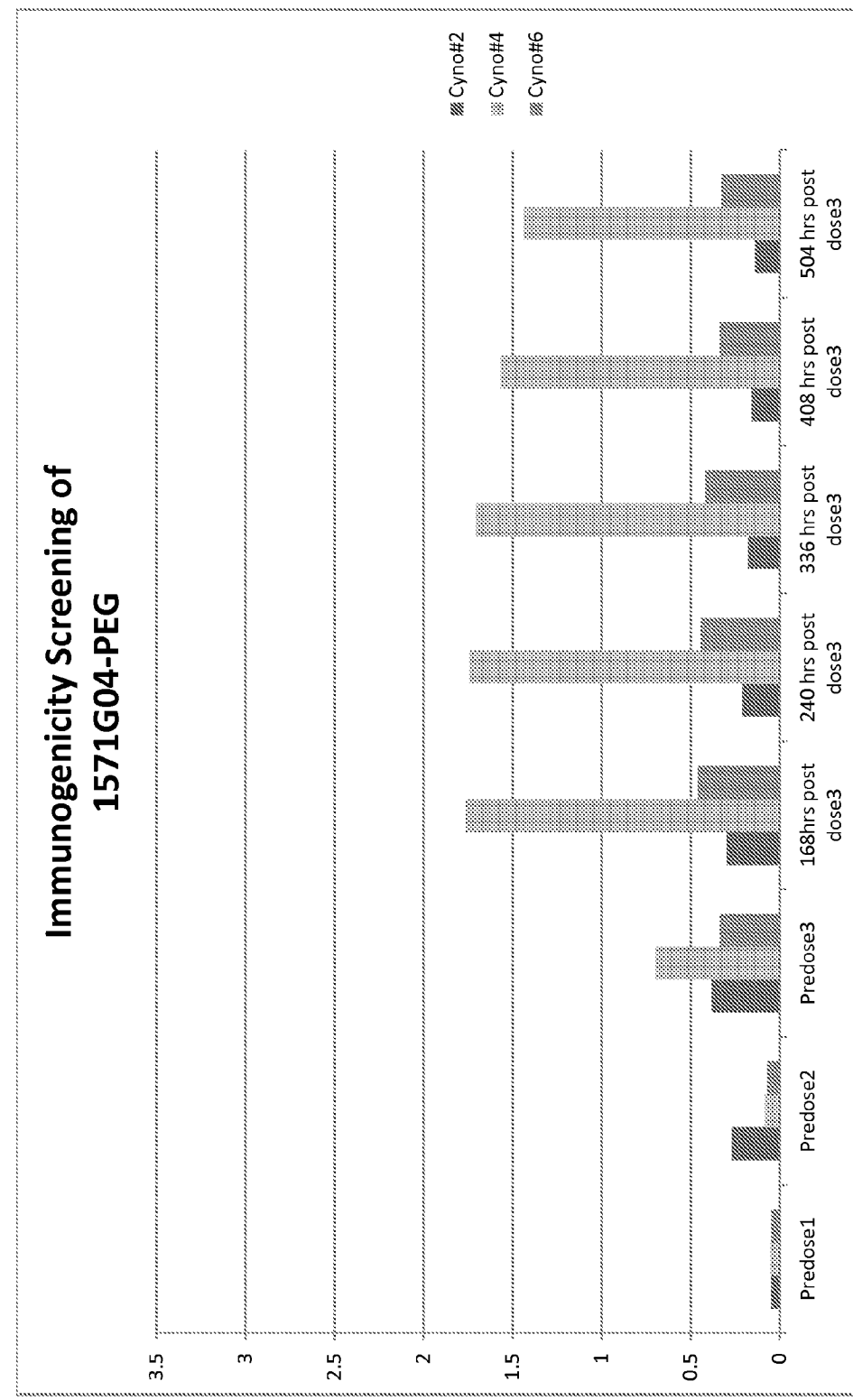

FC FUSION PROTEINS COMPRISING NOVEL LINKERS OR ARRANGEMENTS

CROSS-REFERENCE TO RELATED APPLICATIONS

This application is a 35 U.S.C. 371 national stage filing of International Patent Application No. PCT/US2012/033665, filed Apr. 13, 2012, which claims priority to U.S. Provisional Patent Application No. 61/475,004, filed Apr. 13, 2011, the entire contents of which are incorporated in their entirety by reference herein.

SEQUENCE LISTING

The instant application contains a Sequence Listing which has been submitted electronically in ASCII format and is hereby incorporated by reference in its entirety. Said ASCII copy, created on Dec. 10, 2015, is named MXI_526US_Sequence_Listing.txt and is 143,879 bytes in size.

BACKGROUND

The utility of many therapeutics, particularly biologicals such as peptides, polypeptides and polynucleotides, suffer from inadequate serum half-lives. This necessitates the administration of such therapeutics at high frequencies and/or higher doses, or the use of sustained release formulations, in order to maintain the serum levels necessary for therapeutic effects. Frequent systemic administration of drugs is associated with considerable negative side effects. For example, frequent systemic injections represent a considerable discomfort to the subject, and pose a high risk of administration related infections, and may require hospitalization or frequent visits to the hospital, in particular when the therapeutic is to be administered intravenously. Moreover, in long term treatments daily intravenous injections can also lead to considerable side effects of tissue scarring and vascular pathologies caused by the repeated puncturing of vessels. Similar problems are known for all frequent systemic administrations of therapeutics, such as, for example, the administration of insulin to diabetics, or interferon drugs in patients suffering from multiple sclerosis. All these factors lead to a decrease in patient compliance and increased costs for the health system.

One method for increasing the serum half-life of a protein is to attach it to a pharmacokinetic moiety. One type of pharmacokinetic moiety that has been used is an "Fc" domain of an antibody. Antibodies comprise two functionally independent parts, a variable domain known as "Fab", which binds antigen, and a constant domain known as "Fc", which links to such effector functions as complement activation and attack by phagocytic cells. An Fc domain has a long serum half-life. Capon et al. (1989), Nature 337: 525-31. When fused to a therapeutic protein, an Fc domain can provide longer half-life or incorporate such functions as Fc receptor binding, protein A binding, complement fixation and perhaps even placental transfer.

This application provides novel Fc fusion proteins that increase the serum half-life of various therapeutics, polypeptides having increased serum half-life, and methods for increasing the serum half-life of therapeutics.

SUMMARY

The application provides novel Fc fusion proteins.

In one aspect, the application provides a polypeptide comprising: (a) a $^{10}$Fn3 domain having an altered amino acid sequence relative to the wild-type sequence, wherein the $^{10}$Fn3 domain binds to a target molecule with a $K_D$ of less than 500 nM; (b) an immunoglobulin (Ig) Fc domain; and (c) a hinge sequence.

In certain embodiments, the polypeptide may have the following arrangement from N-terminus to C-terminus: $^{10}$Fn3 domain-hinge-Fc domain. In alternative embodiments, the polypeptide may have the following arrangement from N-terminus to C-terminus: hinge-Fc domain-linker-$^{10}$Fn3 domain.

In exemplary embodiments, the polypeptide is a dimer. The dimer preferably forms via a disulfide bond between free cysteine residues in the hinge region.

In certain embodiments, the polypeptide further comprises a second $^{10}$Fn3 domain having an altered amino acid sequence relative to the wild-type sequence and wherein the second $^{10}$Fn3 domain binds to a target molecule with a $K_D$ of less than 500 nM. The two $^{10}$Fn3 domains may bind to the same or different targets.

In certain embodiments, the Fc domain of the polypeptide may be from an IgG, IgM, IgD, IgE, or IgA. In exemplary embodiments, the Fc domain is derived from an IgG, such as an IgG1.

In various embodiments, the hinge sequence and the Fc domain may be derived from the same or different Ig isotypes.

In certain embodiments, the hinge region comprises residues 104-119 of SEQ ID NO: 22 or a sequence having at least 90% sequence identity thereto.

In another aspect, the application provides a polypeptide comprising an immunoglobulin Fc domain and a heterologous polypeptide, wherein the heterologous polypeptide is fused to the C-terminus of the Fc domain by a polypeptide linker comprising a sequence derived from the C-terminal tail region of the heavy chain of a membrane bound or secretory immunoglobulin.

In certain embodiments, the polypeptide linker comprises a sequence that is at least 80% identical to any one of SEQ ID NOs: 51-70, comprises at least 5 or 10 contiguous amino acids of any one of SEQ ID NOs: 51-70, or comprises the sequence of any one of SEQ ID NOs: 51-70.

In certain embodiments, the heterologous polypeptide comprises a $^{10}$Fn3 domain. In certain embodiments, the heterologous polypeptide comprises two $^{10}$Fn3 domains, wherein the two $^{10}$Fn3 domains may bind to the same or different targets.

In another aspect, the application provides a nucleic acid encoding the Fc fusion proteins provided herein. Also provided are vectors, including expression vectors, comprising a nucleic acid encoding any of the Fc fusion proteins described herein. Also provided are host cells containing such expression vectors and methods for producing the Fc fusion proteins described herein in the host cells.

BRIEF DESCRIPTION OF DRAWINGS

FIG. 1. Inhibition of PCSK9:EGFA (left panel) and PCSK9:ATI-972 (right panel) by PRD460 in a FRET assay.

FIG. 25. Comparison of the wild type human □1 constant region Fc (Fc1) amino acid sequence (SEQ ID NO: 154) with Fc variants Fc4 through Fc23 (SEQ ID NOS: 155-173, respectively). The $C_H1$ domain of the human □1 constant region is not part of the Fc and is therefore not shown. The locations of the hinge region, the $C_H2$ domain, and the $C_H3$ domain are indicated. The Cys residues normally involved in disulfide bonding to the light chain constant region (LC) and heavy chain constant region (HC) are indicated. A ".'' indicates identity to wild type at that position. A "-" indicates a gap introduced into the sequence to optimize alignment. Only locations where the Fc variants differ from wild type are shown, otherwise the Fc sequences match the wild type sequence shown. The sequence positions are numbered according to the universally accepted EU Index numbering system for immunoglobulin proteins. *** indicates the location of the carboxyl terminus and is included to clarify the difference in the carboxyl terminus of Fc6 relative to the other Fc versions.

FIG. 26. Comparison of the wild type BALB/c mouse □2a constant region Fc (mFc1)(SEQ ID NO: 174) and the wild type C57BL/6 mouse □2c constant region Fc (mFc3) (SEQ ID NO: 176) amino acid sequences with mouse Fc effector function minus variants mFc2 (SEQ ID NO: 175) and mFc4 (SEQ ID NO: 177). The location of the hinge region, the $C_H2$ domain, and the $C_H3$ domain are indicated. The Cys residues normally involved in disulfide bonding to the heavy chain constant region (HC) are indicated. A ".'' indicates identity to wild type at that position. A "-" indicates a gap inserted in the sequence to maximize the alignment. The sequence positions are numbered according to the universally accepted EU Index numbering system for immunoglobulin proteins.

FIG. 27. Immunogenicity of 1571G04-PEG in cynomolgus monkeys.

DETAILED DESCRIPTION

Definitions

Figure 2:
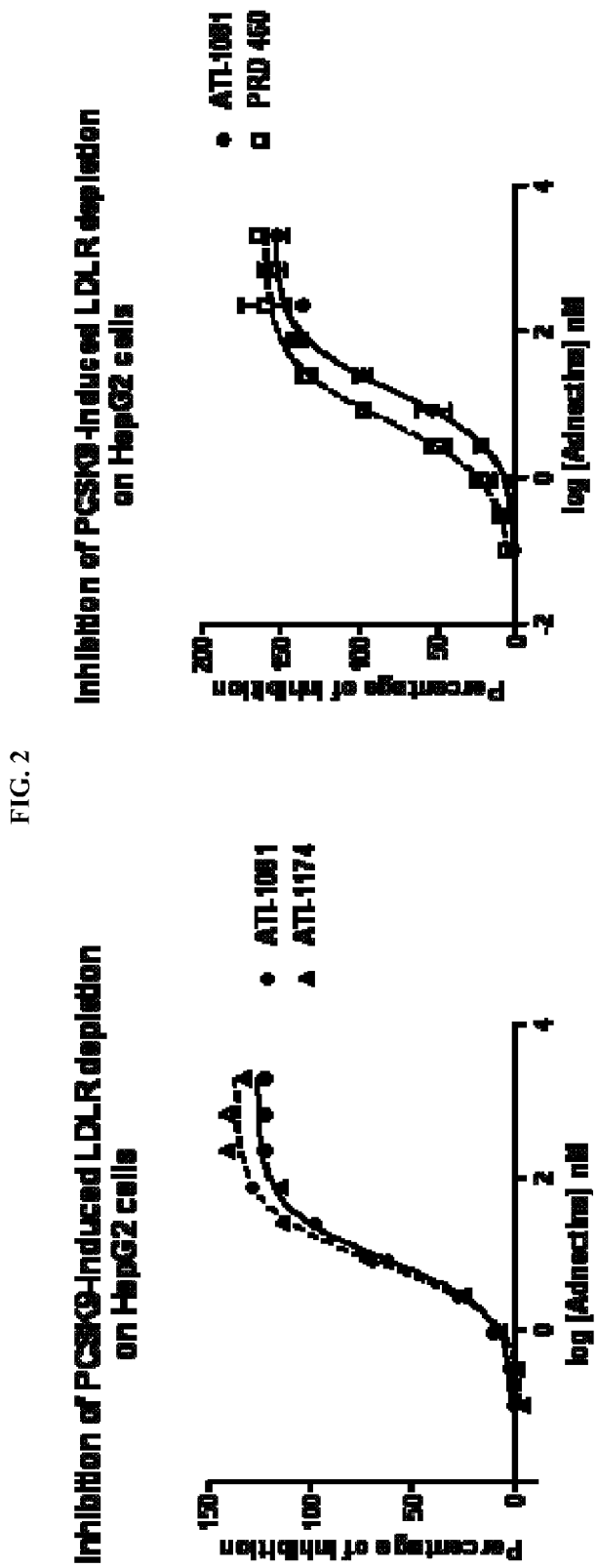
FIG. 2. Inhibition of PCSK9-induced LDLR depletion from HepG2 cell surface by anti-PCSK9 Adnectins.

By a "polypeptide" is meant any sequence of two or more amino acids, regardless of length, post-translation modification, or function. "Polypeptide," "peptide," and "protein" are used interchangeably herein. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxyterminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

The notations "mpk", "mg/kg", or "mg per kg" refer to milligrams per kilogram. All notations are used interchangeably throughout the present disclosure.

The "half-life" of a polypeptide can generally be defined as the time taken for the serum concentration of the polypeptide to be reduced by 50%, in vivo, for example due to degradation of the polypeptide and/or clearance or sequestration of the polypeptide by natural mechanisms. The half-life can be determined in any manner known per se, such as by pharmacokinetic analysis. Suitable techniques will be clear to the person skilled in the art, and may, for example, generally involve the steps of administering a suitable dose of a polypeptide to a rodent or primate; collecting blood samples or other samples from said primate at regular intervals; determining the level or concentration of the polypeptide in said blood sample; and calculating, from (a plot of) the data thus obtained, the time until the level or concentration of the polypeptide has been reduced by 50% compared to the initial level upon dosing. Methods for determining half-life may be found, for example, in Kenneth et al., Chemical Stability of Pharmaceuticals: A Handbook for Pharmacists (1986); Peters et al, Pharmacokinete analysis: A Practical Approach (1996); and "Pharmacokinetics", M Gibaldi & D Perron, published by Marcel Dekker, 2nd Rev. edition (1982).

Half-life can be expressed using parameters such as the t1/2-alpha, t1/2-beta, HL_Lambda_z, and the area under the curve (AUC). In the present specification, an "increase in half-life" refers to an increase in any one of these parameters, any two of these parameters, any three of these parameters or all four of these parameters. An "increase in half-life" in particular refers to an increase in the t1/2-beta and/or HL_Lambda_z, either with or without an increase in the t1/2-alpha and/or the AUC or both. Other PK parameters that can be assessed include volume of distribution (VD), clearance (CL), and mean residence time (MRT). In the present specification, a "change in pharmacokinetics" refers to changes in any one of these parameters, any two of these parameters, or all three of these parameters, in the presence or absence of changes in the half-life parameters listed above.

Fc Fusion Proteins

This application relates to novel Fc fusion proteins having improved properties. The application provides Fc-X fusion proteins having novel linkers that confer favorable properties such as increased expression, reduced immunogenicity and/or increased protease resistance. The application also relates to novel fibronectin based scaffold polypeptide Fc fusions having improved pharmacokinetics properties compared to their non-Fc fusion counterparts. The novel fibronectin based scaffold polypeptide Fc fusions described herein may be designed to bind to any target of interest. In exemplary embodiments, the target is an antigen, a polypeptide or a therapeutic protein target of interest. Exemplary therapeutically desirable targets, include, for example, tumor necrosis factor alpha (TNF-alpha), delta-like protein 4 (DLL4), interleukin 17 (IL-17), proprotein convertase subtilisin kexin type 9 (PCSK9), pregnane X receptor (PXR), epidermal growth factor receptor (EGFR), insulin-like growth factor 1 receptor (IGF-1R), vascular endothelial growth factor receptor (VEGFR2) and interleukin 23 (IL-23).

Fc-X Fusion Proteins with Novel Linkers

In many cases, Fc fusion proteins having the arrangement Fc-X (e.g., a heterologous polypeptide attached to the C-terminus of the Fc domain) contain a linker sequence separating the immunoglobulin domain (Ig domain) from the heterologous polypeptide. These linkers typically are artificial flexible domains, such as GGGGS. However, these sequences are not natural sequences and may lead to undesirable properties, such as immunogenicity. Accordingly, in one aspect, the application provides for novel, improved Fc fusion proteins using linker sequences derived from naturally occurring antibody sequences, including natural allelic or splice variants. In particular, the application provides novel Fc fusion proteins having the arrangement from N-terminus to C-terminus: Fc-$L_1$-X, where Fc is an Fc domain (as described further below), $L_1$ is linker a sequence derived from the natural tail sequence of a membrane-bound or secretory form of an antibody, and X is a heterologous polypeptide. The linker will be positioned in the Fc fusion protein in its natural context, e.g., in its natural place in the Ig CH3 of CH4 sequence. These natural linker sequences will permit the construction of Fc fusion proteins with linkers of varying length that will be in a natural context and therefore likely to have favorable properties with regard to expression, immunogenicity and/or protease resistance.

Most immunoglobulins exist in soluble and membrane-bound isoforms. The membrane-bound isoform consists of the soluble form with a tail alternatively spliced in the CH3 or CH4 domain towards the C-terminus before the stop codon. The tail of the membrane-bound isoform consists of a linker, a trans-membrane segment, and an intracellular segment. Certain immunoglobulins, such as IgA, contain tail segments in their secretory forms, which may also be used as linkers.

In one embodiment, the application provides an Fc fusion protein having the arrangement Fc-$L_1$-X, wherein $L_1$ is a linker sequence derived from the tail segment of a membrane bound form of an immunoglobulin. Exemplary linker sequences include for example: (i) the tail region of the membrane long isoform of IgA1 (m$\alpha 1_L$): SCSVADWQMPPPYVVLDLPQETLEEETPGAN (SEQ ID NO: 51), (ii) the tail region of the membrane variant long isoform of IgA1 (m$\alpha 1_L$ with extra cys): SCCVADWQMPPPYVVLDLPQETLEEETPGAN (SEQ ID NO: 52), (iii) the tail region of the membrane short isoform of IgA1 (m$\alpha 1_s$ with 6 amino acid N-terminal deletion): DWQMPPPYVVLDLPQETLEEETPGAN (SEQ ID NO: 53), (iv) the tail region of the membrane bound form of IgA2: SCCVADWQMPPPYVVLDLPQETLEEETPGAN (SEQ ID NO: 54), (v) the tail region of the membrane bound form of IgD: YLAMTPLIPQSKDENSDDYTTFDDVGS (SEQ ID NO: 55), (vi) the tail region of the membrane-bound form of IgE: ELDVCVEEAEGEAPW (SEQ ID NO: 56), (vii) the tail region of the membrane bound form of IgG: ELQLEES- CAEAQDGELDG (SEQ ID NO: 57), and (viii) the tail region of the membrane bound form of IgM EGEVSADEEGFEN (SEQ ID NO: 58).

In other embodiments, the application provides the application provides an Fc fusion protein having the arrangement Fc-L$_1$-X, wherein L1 is a linker sequence derived from the tail segment of a secretory or soluble form of an immunoglobulin. Exemplary linker sequences include for example: (i) the tail region of the soluble form of IgA1: KPTHVNVSVVMAEVDGTCY (SEQ ID NO: 59), (ii) the tail region of the soluble form of IgA2: KPTHVNVSVVMAEVDGTCY (SEQ ID NO: 60), (iii) the tail region of the soluble form of IgD: YVTDHGPMK (SEQ ID NO: 61), and (iv): the tail region of the soluble form of IgM: PTLYNVSLVMSDTAGTCY (SEQ ID NO: 62).

In certain embodiments, it may be desirable to have a linker sequence containing a free cysteine residue in order to permit the formation of a disulfide bond between linkers thereby forming dimers of the Fc fusion proteins. In other embodiments, it may be desirable to alter the linker sequences to remove free cysteine residues, e.g., by mutating one or more cysteine residues in a linker to another residue, such as a serine, alanine or glycine. Examples of linker sequences derived from the tail regions of membrane bound immunoglobulins that have been altered to remove free cysteine residues include: (i) SXSVADWQMPPPYVVLDLPQETLEEETPGAN, wherein X is serine, alanine or glycine (SEQ ID NO: 63), (ii) SXXVADWQMPPPYVVLDLPQETLEEETPGAN, wherein each X is independently selected from serine, alanine or glycine (SEQ ID NO: 64), (iii) SXXVADWQMPPPYVVLDLPQETLEEETPGAN, wherein each X is independently selected from serine, alanine or glycine (SEQ ID NO: 65), (iv) ELDVXVEEAEGEAPW, wherein X is serine, alanine or glycine (SEQ ID NO: 66), and (v) ELQLEESXAEAQDGELDG, wherein X is serine, alanine or glycine (SEQ ID NO: 67). Examples of linker sequences derived from the tail regions of secretory forms of immunoglobulins that have been altered to remove free cysteine residues include: (i) KPTHVNVSVVMAEVDGTXY, wherein X is serine, alanine or glycine (SEQ ID NO: 68), (ii) KPTHVNVSVVMAEVDGTXY, wherein X is serine, alanine or glycine (SEQ ID NO: 69), and (iii) PTLYNVSLVMSDTAGTXY, wherein X is serine, alanine or glycine (SEQ ID NO: 70).

In one embodiment, the application provides an Fc fusion protein having the arrangement Fc-L$_1$-X, wherein L$_1$ is a linker sequence comprising, consisting essentially of, or consisting of an amino acid sequence that is at least 50%, 60%, 75%, 80%, 85%, 90%, 95%, 96%, 97%, 98%, or 99% to any one of SEQ ID NOs: 51-70, or an amino acid sequence comprising, consisting essentially of, or consisting of any one of SEQ ID NOs: 51-70. In another embodiment, the application provides an Fc fusion protein having the arrangement Fc-L$_1$-X, wherein L$_1$ is a linker sequence comprising at least 2, 5, 10, 12, 15, 20, 25, or 30 contiguous amino acid residues from any of SEQ ID NOs: 51-70, or a sequence comprising from 1-5, 1-10, 1-15, 1-20, 1-25, 2-5, 2-10, 2-15, 2-20, 2-25, 5-10, 5-15, 5-20, 5-25, 5-30, 10-15, 10-20, 10-25, 10-30, 15-20, 15-25, 15-30, 20-25, 25-30 or 25-30 contiguous amino acid residues from any of SEQ ID NOs: 51-70. In certain embodiments, the linker sequence does not contain a cysteine residue. In certain embodiments, the linker sequence may be extended in length by repetition, concatenation or combination of any one of SEQ ID NOs: 51-70, or fragments thereof.

In certain embodiments, the Fc-L$_1$-X fusion proteins provided herein may have increased expression, decreased immunogenicity, and/or improved protease resistance relative to Fc fusion proteins having different linker sequences. For example, a host cell comprising an expression vector encoding for an Fc-L$_1$-X fusion protein provided herein may provide at least 10%, 20%, 30%, 40%, 50% 75% or 100% greater expression than an equivalent Fc fusion protein having a non-naturally occurring linker sequence, or at least 2-fold, 3-fold, 4-fold, 5-fold or 10-fold higher levels of expression than an equivalent Fc fusion protein having a non-naturally occurring linker sequence. In certain embodiments, an Fc-L$_1$-X fusion protein provided herein may have reduced immunogenicity relative an equivalent Fc fusion protein having a non-naturally occurring linker sequence. The immunogenicity of a polypeptide described herein may be assessed, for example, by one or more of the following methods: Human Leukocyte Antigen ("HLA") binding, in silico prediction of HLA binding (for example, with the Epimatrix program), in vitro activation of human T-cells, in vivo animal immune response, or other methods for evaluating immunogenicity potential. In other embodiments, an Fc-L$_1$-X fusion protein provided herein may have increased protease resistance relative to an equivalent Fc fusion protein having a non-naturally occurring linker sequence.

The Fc-L$_1$-X fusion proteins described herein contain an X portion that may be any protein of interest. In exemplary embodiments, the X portion is a therapeutic peptide or protein, such as, for example, interferon alpha, L-asparaginas, or granulocyte colony-stimulating factor. In certain embodiments, the X portion of the fusions described herein is an antibody, or fragment thereof, such as, for example, and anti-TNF-alpha antibody. In an exemplary embodiment, the X portion of the Fc fusion proteins is a polypeptide comprising $^{10}$Fn3 domain, including, for example, a polypeptide comprising a $^{10}$Fn3 domain that binds to a target such as tumor necrosis factor alpha (TNF-alpha), delta-like protein 4 (DLL4), interleukin 17 (IL-17), proprotein convertase subtilisin kexin type 9 (PCSK9), pregnane X receptor (PXR), epidermal growth factor receptor (EGFR), insulin-like growth factor 1 receptor (IGF-1R), vascular endothelial growth factor receptor (VEGFR2) and interleukin 23 (IL-23).

Fibronectin Based Scaffold Protein-Fc Fusions

Provided herein are Fc fusion proteins comprising an Fc domain fused to a polypeptide that binds to a target. The polypeptide that binds to a target may be derived from a fibronectin or tenascin molecule or it may be a synthetic molecule that is based on the sequences and structure of fibronectin and tenascin molecules. Polypeptides that may be used in Fc fusion proteins are described, e.g., in WO2010/051274, WO2010/051310 and WO2009/086116.

In one aspect, the application provides Fc fusion proteins comprising an Fc domain fused, a polypeptide comprising a $^{10}$Fn3 domain, and a hinge sequence. These fusions are referred to collectively herein as Fc-$^{10}$Fn3 fusions. The Fc-$^{10}$Fn3 fusion proteins may be arranged in either order, e.g., from N-terminus to C-terminus, Fc-$^{10}$Fn3 or $^{10}$Fn3-Fc. In an exemplary embodiment, a Fc-$^{10}$Fn3 fusion protein has the following arrangement from N-terminus to C-terminus: $^{10}$Fn3-hinge-Fc domain, wherein $^{10}$Fn3 refers to a polypeptide comprising a $^{10}$Fn3 domain, hinge refers to an immunoglobulin hinge sequence as described further herein, and Fc refers to an immunoglobulin Fc domain. In an exemplary embodiment, a Fc-$^{10}$Fn3 fusion protein has the following arrangement from N-terminus to C-terminus: $^{10}$Fn3-Fc domain, wherein $^{10}$Fn3 refers to a polypeptide comprising a $^{10}$Fn3 domain and Fc refers to an immunoglobulin Fc domain. In another exemplary embodiment, a Fc-$^{10}$Fn3 fusion protein has the following arrangement from N-terminus to C-terminus: hinge-Fc domain-L$_2$-$^{10}$Fn3, wherein hinge refers to an immunoglobulin hinge sequence as described further herein, Fc refers to an immunoglobulin Fc domain, L$_2$ refers to a linker as further defined herein, and $^{10}$Fn3 refers to a polypeptide comprising a $^{10}$Fn3 domain. In an exemplary embodiment, a Fc-$^{10}$Fn3 fusion protein has the following arrangement from N-terminus to C-terminus: Fc domain-L$_2$-$^{10}$Fn3, wherein Fc refers to an immunoglobulin Fc domain, L$_2$ refers to a linker as further defined herein, and $^{10}$Fn3 refers to a polypeptide comprising a $^{10}$Fn3 domain. In an exemplary embodiment, a Fc-$^{10}$Fn3 fusion protein has the following arrangement from N-terminus to C-terminus: Fc domain-$^{10}$Fn3, wherein Fc refers to an immunoglobulin Fc domain and $^{10}$Fn3 refers to a polypeptide comprising a $^{10}$Fn3 domain. In an exemplary embodiment, a Fc-$^{10}$Fn3 fusion protein has the following arrangement from N-terminus to C-terminus: hinge-Fc domain-$^{10}$Fn3, wherein hinge refers to an immunoglobulin hinge sequence as described further herein, Fc refers to an immunoglobulin Fc domain, and $^{10}$Fn3 refers to a polypeptide comprising a $^{10}$Fn3 domain. In either orientation, the Fc-$^{10}$Fn3 fusion proteins described herein may further contain an N-terminal methionine and/or a leader sequence (e.g., for expression in mammalian cells).

In certain embodiments, the Fc-$^{10}$Fn3 fusion proteins described herein comprise a hinge sequence, preferably a hinge sequence that contains a free cysteine residue that is capable of forming a disulfide bond such that the Fc-$^{10}$Fn3 fusion protein forms a dimer. The hinge sequence may naturally contain a cysteine residue, or may be engineered to contain one or more cysteine residues.

The Fc-$^{10}$Fn3 fusion proteins described herein may contain an immunoglobulin hinge region. The hinge region may be derived from antibodies belonging any of the immunoglobulin classes, i.e. IgA, IgD, IgE, IgG, or IgM. In certain embodiments, the hinge region is derived from any of the IgG antibody subclasses, i.e. IgG1, IgG2, IgG3, and IgG4. In some embodiments, the hinge region may further include residues derived from the CH1 and CH2 regions that flank the core hinge sequence, as discussed further below.

Shown below is the sequence of a human IgG1 immunoglobulin constant region, and the relative position of each domain within the constant region are indicated based on the EU numbering format: ASTKGPSVFPLAPSSKSTSGG-TAALGCLVKDYFPEPVTVSWNSGALTSGVHTFPAV-LQSSGLYS LSSVVTVPSSSLGTQTYICNVNHKPSNTK-VDKKVEPKSC<u>DKTHTCPPCPAPELLGG</u>PSVFLFP PKPKDTLMISRTPEVTCVVVDVSHEDPEVKFN-WYVDGVEVHNAKTKPREEQYNSTYR VVSVLTVL-HQDWLNGKEYKCKVSNKALPAPIEKTISKAK-GQPREPQVYTLPPSRDELTK NQVSLTCLVKGFYPSDIAVEWESNGQPENNYKTTP-PVLDSDGSFFLYSKLTVDKSRWQ QGNVFSCSVM-HEALHNHYTQKSLSLSPGK (SEQ ID NO: 22). The core hinge sequence is underlined, and the CH1 region is italicized; the CH2 and CH3 regions are in regular text. It should be understood that the C-terminal lysine is optional. In certain embodiments, the C-terminal lysine of an IgG sequence may be removed or replaced with a non-lysine amino acid, such as alanine, to further increase the serum half-life of the Fc fusion protein.

In certain embodiments, the Fc-$^{10}$Fn3 fusion proteins described herein comprise a hinge region derived from a human IgG1. In some embodiments, the hinge region comprises the core hinge residues spanning positions 104-119 of SEQ ID NO: 22 (DKTHTCPPCPAPELLG; SEQ ID NO: 23) of IgG1, which corresponds to positions 221-236 according to EU numbering.

In certain embodiments, the hinge sequence may include substitutions that confer desirable pharmacokinetic, biophysical, and/or biological properties. Some exemplary hinge sequences include EPKSS<u>DKTHTCPPCPAPELLGG</u>PS (SEQ ID NO: 24; core hinge region underlined), EPKSS<u>DKTHTCPPCPAPELLGG</u>SS (SEQ ID NO: 25; core hinge region underlined), EPKSS<u>GSTHTCPPCPAPELLGG</u>SS (SEQ ID NO: 26; core hinge region underlined), <u>DKTHTCPPCPAPELLGG</u>PS (SEQ ID NO: 27; core hinge region underlined), and <u>DKTHTCPPCPAPELLGG</u>SS (SEQ ID NO: 28, core hinge region underlined). In one embodiment, the hinge sequence is a derivative of an IgG1 hinge comprising a P122S substitution based on the numbering in SEQ ID NO: 22 (EU numbering 238) (e.g., the Proline residue at position 122 in SEQ ID NO: 22 is substituted with serine). The P122S substitution ablates Fc effector function and is exemplified by the hinges having any one of SEQ ID NOs: 25, 26, and 28. In another embodiment, the hinge sequence is a derivative of an IgG1 hinge comprising D104G and K105S substitutions based on the numbering in SEQ ID NO: 22 (EU numbering 221-222). The D104G and K105S substitutions remove a potential cleavage site and therefore increase the protease resistance of the fusion molecule. A hinge having D104G and K105S substitutions is exemplified in SEQ ID NO: 26. In another embodiment, the hinge sequence is a derivative of an IgG1 hinge comprising a C103S substitution based on the numbering in SEQ ID NO: 22 (EU numbering 220). The C103S substitution prevents improper cysteine bond formation in the absence of a light chain. Hinges having a C103S substitution are exemplified by SEQ ID NOs: 24-26.

In one embodiment, the application provides a Fc-$^{10}$Fn3 fusion protein, wherein the hinge sequence comprises, consists essentially of, or consists of an amino acid sequence that is at least 50%, 60%, 75%, 80%, 85%, 90%, 95%, 96%, 97%, 98%, or 99% to any one of SEQ ID NOs: 24-28, or comprises, consists essentially of, or consists of an amino acid sequence of any one of SEQ ID NOs: 24-28. In another embodiment, the application provides a Fc-$^{10}$Fn3 fusion protein, wherein the hinge portion comprises at least 2, 5, 10, 12, 15, 18 or 20 contiguous amino acid residues of any of SEQ ID NOs: 24-28, or a sequence comprising from 1-5, 1-10, 1-15, 1-20, 2-5, 2-10, 2-15, 2-20, 5-10, 5-15, 5-20, 10-15, 10-20, or 15-20 contiguous amino acid residues from any of SEQ ID NOs: 24-28. In exemplary embodiments, the hinge sequence comprises a cysteine residue.

In certain embodiments, an Fc fusion protein does not comprise a hinge. For example, an Fc fusion protein may comprise an Fc domain linked to a heterologous protein, e.g., in the Fc-X or X-Fc format, without comprising a hinge or a core hinge. In one example, an Fc fusion protein does not comprise the sequence EPKSSDKTHTCPPCP (SEQ ID NO: 89) or a variant thereof.

In certain embodiments, an Fc fusion protein does not comprise a linker. For example, an Fc fusion protein may comprise an Fc domain that is linked directly to a heterologous protein, e.g., a $^{10}$Fn3 protein without an intervening sequence. In certain embodiments, there may be 1, 2, 3, 4 or 5 amino acids (e.g., from 1-5 or 1-10 amino acids) between the Fc domain and the heterologous protein. Such Fc fusion proteins may be X-Fc or Fc-X fusion proteins, wherein X is the heterologous protein, and wherein X and Fc are directly linked to each other.

In certain embodiments, an Fc fusion protein does not comprise a hinge and does not comprise a linker.

The Fc-$^{10}$Fn3 fusion proteins described herein comprise an Fc domain, as described further below. In certain embodiments, the Fc domain and the hinge region may be derived from one antibody class or subclass. For example, the hinge region and the Fc domain may be derived from IgG1. In other embodiments, the Fc domain and hinge region may be derived from different antibody classes or subclasses. For example, the Fc domain may be derived from IgG2 or IgG4 and the hinge region may be derived from IgG1.

In certain embodiments, a Fc-$^{10}$Fn3 fusion protein described herein has the arrangement hinge-Fc domain-$L_2$-$^{10}$Fn3, wherein $L_2$ is a linker that connects the Fc domain to the polypeptide comprising a $^{10}$Fn3 domain. In exemplary embodiments, the $L_2$ linker is selected from the group consisting of: GSGSGSGSGSGS (SEQ ID NO: 33), AGGGGSG (SEQ ID NO: 37), AGGGGSGG (SEQ ID NO: 38), QPDEPGGS (SEQ ID NO: 45), ELQLEESAAEAQD-GELD (SEQ ID NO: 46), TVAAPS (SEQ ID NO: 47), QPDEPGGSG (SEQ ID NO: 48), ELQLEESAAEAQD-GELDG (SEQ ID NO: 49), TVAAPSG (SEQ ID NO: 50), and any one of SEQ ID NOs: 51-70, 81-88 and 90-98. In other embodiments, the $L_2$ linker comprises, consists essentially of, or consists of an amino acid sequence that is at least 50%, 60%, 75%, 80%, 85%, 90%, 95%, 96%, 97%, 98%, or 99% to any one of SEQ ID NOs: 33, 37-38, 45-70, 81-88 and 90-98, or comprises, consists essentially of, or consists of any one of SEQ ID NOs: 33, 37-38, 45-70, 81-88 and 90-98. In another embodiment, $L_2$ comprises at least 2, 5, 10, 12, 15, 20, 25, or 30 contiguous amino acid residues from any of SEQ ID NOs: 33, 37-38, 45-70, 81-88 and 90-98, or a sequence comprising from 1-5, 1-10, 1-15, 1-20, 1-25, 2-5, 2-10, 2-15, 2-20, 2-25, 5-10, 5-15, 5-20, 5-25, 5-30, 10-15, 10-20, 10-25, 10-30, 15-20, 15-25, 15-30, 20-25, 25-30 or 25-30 contiguous amino acid residues from any of SEQ ID NOs: 33, 37-38, 45-70, 81-88 and 90-98. In certain embodiments, the $L_2$ linker sequence does not contain a cysteine residue. In certain embodiments, the linker sequence may be extended in length by repetition, concatenation or combination of any one of SEQ ID NOs: 33, 37-38, 45-70, 81-88 and 90-98, or fragments thereof.

Suitable Fc domains and polypeptides comprising $^{10}$Fn3 domains for use in the Fc-$^{10}$Fn3 fusion proteins are described further below.

In certain embodiments, the Fc-$^{10}$Fn3 fusion proteins provided herein may have an increased serum half-life relative to a $^{10}$Fn3 domain without the Fc fusion or relative to a $^{10}$Fn3 domain fused to a different pharmacokinetic moiety, such as, for example a polyethylene glycol (PEG) moiety. For example, a Fc-$^{10}$Fn3 fusion protein provided herein may have a serum half life that is at least 10%, 20%, 30%, 40%, 50% 75% or 100% greater than the serum half life of an equivalent $^{10}$Fn3 domain without the Fc domain or relative to an equivalent $^{10}$Fn3 domain fused to a different pharmacokinetic moiety, such as, for example a polyethylene glycol (PEG) moiety. In certain embodiments, a Fc-$^{10}$Fn3 fusion protein provided herein has a serum half life that is at least 2-fold, 3-fold, 4-fold, 5-fold or 10-fold longer than the serum half life of an equivalent $^{10}$Fn3 domain without the Fc domain or relative to an equivalent $^{10}$Fn3 domain fused to a different pharmacokinetic moiety, such as, for example a polyethylene glycol (PEG) moiety.

In certain embodiments, an Fc fusion protein, e.g., a $^{10}$Fn3-Fc fusion protein, is a dimer, wherein each monomer comprises a fusion protein (a homodimer). In certain embodiments, an Fc fusion protein, e.g., a $^{10}$Fn3-Fc fusion protein, is a heterodimer comprising, e.g., a monomer that comprises an Fc fusion protein and a monomer that comprises an Fc that is not linked to a heterologous protein. The Fc portion of a monomer may comprise one or more amino acid modifications (or mutations) relative to a wild type Fc that favor dimer formation with another Fc. For example, an Fc of a dimer may comprise a "hole" and the other Fc of the dimer may comprise a "bump" or "knob," as described, e.g., in WO96/027011; U.S. Pat. No. 5,731,168 and U.S. Pat. No. 5,821,333. Other modification, such as electrostatic modifications may be used to enhance dimer formation. Exemplary modifications are described, e.g., in WO2007/110205; WO2009/089004 and WO2010/129304. Such changes are particularly useful for enhancing the association of two heterologous monomers to form a dimer, such as a dimer that comprises a monomer comprising an Fc fusion protein and a monomer comprising an Fc that is different from the Fc fusion protein, e.g., by the lack of a heterologous protein. Monomers of the dimer may be linked covalently or non covalently to each other.

In certain embodiments, an Fc fusion protein comprises a monomer comprising the structure X-Fc and a monomer comprising the structure Fc-X (or Fc-Y), wherein each monomer may optionally comprise a linker and optionally comprise a hinge.

A heterodimeric Fc fusion protein may comprise a single chain Fc (scFc), wherein the first and the second Fc domain (or the first and the second hinge-Fc domains) are linked through a linker. In one embodiment, a scFc comprises in N- to C-terminal order a first CH2 domain, which first CH2 domain is linked to a first CH3 domain, which CH3 domain is linked to an Fc linker, which Fc linker is linked the a second CH2 domain, which second CH2 domain is linked to a second CH3 domain, wherein the first and the second CH2 and CH3 domains associate to form a dimeric Fc. An scFc may comprise in N- to C-terminal order a first hinge, which first hinge is linked to a first CH2 domain, which first CH2 domain is linked to a first CH3 domain, which first CH3 domain is linked to an Fc linker, which Fc linker is linked to a second hinge, which second hinge is linked to a second CH2 domain, which second CH2 domain is linked to a second CH3 domain, wherein the first and the second hinges, CH2 domains and CH3 domains associate to form a dimeric Fc. scFcs are described, e.g., in WO2008/131242, WO2008/143954 and WO2008/012543.

Fc Domains

Described herein are polypeptide fusions that comprise an Fc portion fused to a heterologous portion. In some aspects, the heterologous portion is a $^{10}$Fn3 domain.

As used herein, "Fc portion" encompasses domains derived from the constant region of an immunoglobulin, preferably a human immunoglobulin, including a fragment, analog, variant, mutant or derivative of the constant region. Suitable immunoglobulins include IgG1, IgG2, IgG3, IgG4, and other classes such as IgA, IgD, IgE and IgM. The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in combination.

The constant region of an immunoglobulin is responsible for many important antibody functions including Fc receptor (FcR) binding and complement fixation. There are five major classes of heavy chain constant region, classified as IgA, IgG, IgD, IgE, IgM, each with characteristic effector functions designated by isotype. For example, IgG is separated into four subclasses known as IgG1, IgG2, IgG3, and IgG4.

Ig molecules interact with multiple classes of cellular receptors. For example IgG molecules interact with three classes of Fcγreceptors (FcγR) specific for the IgG class of antibody, namely FcγRI, FcγRII, and FcγRIII. The important sequences for the binding of IgG to the FcγR receptors have been reported to be located in the CH2 and CH3 domains. The serum half-life of an antibody is influenced by the ability of that antibody to bind to an Fc receptor (FcR). Similarly, the serum half-life of IgFc fusion proteins is also influenced by the ability to bind to such receptors (Gillies S D et al., (1999) *Cancer Res.* 59:2159-66).

The fusion proteins disclosed herein comprise an Fc portion that includes at least a portion of the carboxy-terminus of an immunoglobulin heavy chain. For example, the Fc portion may comprise: a CH2 domain, a CH3 domain, a CH4 domain, a CH2-CH3 domain, a CH2-CH4 domain, a CH2-CH3-CH4 domain, a hinge-CH2 domain, a hinge-CH2-CH3 domain, a hing-CH2-CH4 domain, or a hinge-CH2-CH3-CH4 domain. The Fc domain may be derived from antibodies belonging any of the immunoglobulin classes, i.e., IgA, IgD, IgE, IgG, or IgM or any of the IgG antibody subclasses, i.e., IgG1, IgG2, IgG3, and IgG4. The Fc domain may be a naturally occurring Fc sequence, including natural allelic or splice variants. Alternatively, the Fc domain may be a hybrid domain comprising a portion of an Fc domain from two or more different Ig isotypes, for example, an IgG2/IgG4 hybrid Fc domain. In exemplary embodiments, the Fc domain is derived from a human immunoglobulin molecule. Alternatively, the Fc domain may be a humanized or deimmunized version of an Fc domain from a non-human animal, including but not limited to mouse, rat, rabbit, camel, llama, dromedary and monkey.

In certain embodiments, the Fc domain is a variant Fc sequence, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity.

For example, one may make modifications in the Fc region in order to generate an Fc variant that (a) has increased or decreased antibody-dependent cell-mediated cytotoxicity (ADCC), (b) increased or decreased complement mediated cytotoxicity (CDC), (c) has increased or decreased affinity for C1q and/or (d) has increased or decreased affinity for a Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc substitutions therein, e.g. of the specific Fc region positions identified herein.

A variant Fc domain may also comprise a sequence alteration wherein sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). Even when cysteine residues are removed, the single chain Fc domains can still form a dimeric Fc domain that is held together non-covalently. In other embodiments, a native Fc domain may be modified to make it more compatible with a selected host cell. For example, one may remove the PA sequence near the N-terminus of a typical native Fc, which may be recognized by a digestive enzyme in *E. coli* such as proline iminopeptidase. One may also add an N-terminal methionine residue, especially when the molecule is expressed recombinantly in a bacterial cell such as *E. coli*. In another embodiment, a portion of the N-terminus of a native Fc domain is removed to prevent N-terminal heterogeneity when expressed in a selected host cell. For this purpose, one may delete any of the first 20 amino acid residues at the N-terminus, particularly those at positions 1, 2, 3, 4 and 5. In other embodiments, one or more glycosylation sites within the Fc domain may be removed. Residues that are typically glycosylated (e.g., asparagine) may confer cytolytic response. Such residues may be deleted or substituted with unglycosylated residues (e.g., alanine) In other embodiments, sites involved in interaction with complement, such as the C1q binding site, may be removed from the Fc domain. For example, one may delete or substitute the EKK sequence of human IgG1. In certain embodiments, sites that affect binding to Fc receptors may be removed, preferably sites other than salvage receptor binding sites. In other embodiments, an Fc domain may be modified to remove an ADCC site. ADCC sites are known in the art; see, for example, Molec. Immunol. 29 (5): 633-9 (1992) with regard to ADCC sites in IgG1. Specific examples of variant Fc domains are disclosed for example, in WO 97/34631 and WO 96/32478.

In certain embodiments, an Fc fusion protein described herein comprises the CH2 and CH3 regions of a human IgG1 as shown below: VFLFPPKPKDTLMISRTPEVTCVVVD-VSHEDPEVKFNWYVDGVEVHNAKTKPREEQYN STYRVVSVLTVLHQDWLNGKEYKCKVSNKALPA-PIEKTISKAKGQPREPQVYTLPPSRD ELTKNQVSLT-CLVKGFYPSDIAVEWESNGQPENNYKTTPPVLDS-DGSFFLYSKLTVDKS RWQQGNVFSCSVMHEALHNHYTQKSLSLSPGK (SEQ ID NO: 31). It should be understood that the glycine and lysine at the end of SEQ ID NO: 31 are optional. In other embodiments, an Fc fusion protein described herein comprises an Fc domain that is at least 50%, 60%, 75%, 80%, 85%, 90%, 95%, 96%, 97%, 98%, or 99% identical to SEQ ID NO: 31. In other embodiments, an Fc fusion protein described herein comprises an Fc domain having at least 50, 100, or 150 contiguous amino acids of SEQ ID NO: 31. In other embodiments, an Fc fusion protein described herein comprises an Fc domain having from 50-100, 50-150, or 100-150 contiguous amino acids of SEQ ID NO: 31. In yet other embodiments, an Fc fusion protein described herein comprises an Fc domain comprising SEQ ID NO: 31 with from 1-5, 1-10, 1-15, 1-20, or 1-25 substitutions or conservative substitutions.

Additional Fc variants are described below. It is understood that the Fc regions of the disclosure comprise the numbering scheme according to the EU index as in Kabat et al. (1991, NIH Publication 91-3242, National Technical Information Service, Springfield, Va.).

The present disclosure encompasses variant Fc portions which have altered binding properties for an Fc ligand relative to an unmodified parent Fc molecule. For example, an Fc fusion protein described herein may comprise an Fc region having one or more of amino acid residues 234, 235, 236, 237, 297, 318, 320 and 322 substituted to a different amino acid residue, such that the variant Fc region has an altered affinity for an effector ligand, e.g., an Fc receptor or the C1 component of complement, as described in U.S. Pat. Nos. 5,624,821 and 5,648,260, both to Winter et al.

In another example, one or more of amino acid residues 329, 331 and 322 can be replaced such that the variant Fc region has altered C1q binding and/or reduced or abolished complement dependent cytotoxicity (CDC), as described in U.S. Pat. No. 6,194,551 by Idusogie et al.

In another example, one or more amino acid residues within amino acid positions 231 and 239 may be altered to thereby alter the ability of the variant Fc region to fix complement. This approach is described further in WO 94/29351 by Bodmer et al.

In yet another example, the Fc region may be modified to increase antibody dependent cellular cytotoxicity (ADCC) and/or to increase the affinity for an Fcy receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439. Exemplary substitutions include 236A, 239D, 239E, 268D, 267E, 268E, 268F, 324T, 332D, and 332E. Exemplary variants include 239D/332E, 236A/332E, 236A/239D/332E, 268F/324T, 267E/268F, 267E/324T, and 267E/268F/324T. Other modifications for enhancing FcyR and complement interactions include but are not limited to substitutions 298A, 333A, 334A, 326A, 247I, 339D, 339Q, 280H, 290S, 298D, 298V, 243L, 292P, 300L, 396L, 305I, and 396L. These and other modifications are reviewed in Strohl, 2009, Current Opinion in Biotechnology 20:685-691.

Fc modifications that increase binding to an Fc gamma receptor include amino acid modifications at any one or more of amino acid positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 324, 327, 329, 330, 335, 337, 3338, 340, 360, 373, 376, 379, 382, 388, 389, 398, 414, 416, 419, 430, 434, 435, 437, 438 or 439 of the Fc region, wherein the numbering of the residues in the Fc region is that of the EU index as in Kabat (WO00/42072).

Other Fc modifications that can be made to Fcs are those for reducing or ablating binding to FcyR5 and/or complement proteins, thereby reducing or ablating Fc-mediated effector functions such as ADCC, ADCP, and CDC. Exemplary modifications include but are not limited substitutions, insertions, and deletions at positions 234, 235, 236, 237, 267, 269, 325, and 328, wherein numbering is according to the EU index. Exemplary substitutions include but are not limited to 234G, 235G, 236R, 237K, 267R, 269R, 325L, and 328R, wherein numbering is according to the EU index. An Fc variant may comprise 236R/328R. Other modifications for reducing FcyR and complement interactions include substitutions 297A, 234A, 235A, 237A, 318A, 228P, 236E, 268Q, 309L, 330S, 331 S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, Current Opinion in Biotechnology 20:685-691.

Optionally, the Fc region may comprise a non-naturally occurring amino acid residue at additional and/or alternative positions known to one skilled in the art (see, e.g., U.S. Pat. Nos. 5,624,821; 6,277,375; 6,737,056; 6,194,551; 7,317,091; 8,101,720; PCT Patent Publications WO 00/42072; WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/020114).

Fc variants that enhance affinity for an inhibitory receptor FcyRllb may also be used. Such variants may provide an Fc fusion protein with immunomodulatory activities related to FcyR1 lb$^+$ cells, including for example B cells and monocytes. In one embodiment, the Fc variants provide selectively enhanced affinity to FcyRllb relative to one or more activating receptors. Modifications for altering binding to FcyR1 lb include one or more modifications at a position selected from the group consisting of 234, 235, 236, 237, 239, 266, 267, 268, 325, 326, 327, 328, and 332, according to the EU index. Exemplary substitutions for enhancing FcyR1 lb affinity include but are not limited to 234D, 234E, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. Exemplary substitutions include 235Y, 236D, 239D, 266M, 267E, 268D, 268E, 328F, 328W, and 328Y. Other Fc variants for enhancing binding to FcyR1 lb include 235Y/267E, 236D/267E, 239D/268D, 239D/267E, 267E/268D, 267E/268E, and 267E/328F.

The affinities and binding properties of an Fc region for its ligand may be determined by a variety of in vitro assay methods (biochemical or immunological based assays) known in the art including but not limited to, equilibrium methods (e.g., enzyme-linked immunoabsorbent assay (ELISA), or radioimmunoassay (RIA)), or kinetics (e.g., BIACORE analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

An Fc fusion protein of the present disclosure may also comprise an Fc portion which increases the serum half-life of the Fc-fusion protein. For example, this may be done by increasing the binding affinity of the Fc region for FcRn. For example, one or more of more of following residues can be mutated: 252, 254, 256, 433, 435, 436, as described in U.S. Pat. No. 6,277,375.

Other exemplary variants that increase binding to FcRn and/or improve pharmacokinetic properties include substitutions at positions 259, 308, 428, and 434, including for example 259I, 308F, 428L, 428M, 434S, 434H, 434F, 434Y, and 434M. Other variants that increase Fc binding to FcRn include: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 286A, 305A, 307A, 307Q, 311A, 312A, 376A, 378Q, 380A, 382A, 434A (Shields et al, Journal of Biological Chemistry, 2001, 276(9):6591-6604), 252F, 252T, 252Y, 252W, 254T, 256S, 256R, 256Q, 256E, 256D, 256T, 309P, 311 S, 433R, 433S, 433I, 433P, 433Q, 434H, 434F, 434Y, 252Y/254T/256E, 433K/434F/436H, 308T/309P/311S (Dall Acqua et al. Journal of Immunology, 2002, 169:5171-5180, Dall'Acqua et al., 2006, Journal of Biological Chemistry 281:23514-23524). Other modifications for modulating FcRn binding are described in Yeung et al., 2010, J Immunol, 182:7663-7671. In certain embodiments, hybrid IgG isotypes with particular biological characteristics may be used. For example, an IgG1/IgG3 hybrid variant may be constructed by substituting 1gG1 positions in the CH2 and/or CH3 region with the amino acids from 1gG3 at positions where the two isotypes differ. Thus a hybrid variant IgG antibody may be constructed that comprises one or more substitutions, e.g., 274Q, 276K, 300F, 339T, 356E, 358M, 384S, 392N, 397M, 4221, 435R, and 436F. In other embodiments of the invention, an 1gG1/1gG2 hybrid variant may be constructed by substituting IgG2 positions in the CH2 and/or CH3 region with amino acids from 1gG1 at positions where the two isotypes differ. Thus a hybrid variant IgG antibody may be constructed that comprises one or more substitutions, e.g., one or more of the following amino acid substitutions: 233E, 234L, 235L, -236G (referring to an insertion of a glycine at position 236), and 327A.

In certain embodiments, the glycosylation of the Fc is modified. Oligosaccharides that are covalently attached to the Fc region can be changed, for example by expressing an IgG in various organisms or cell lines, engineered or otherwise (for example Lec-13 CHO cells or rat hybridoma YB2/0 cells), by regulating enzymes involved in the glycosylation pathway (for example FUT8 [a1,6-fucosyltransferase] and/or β1-4-N-acetylglucosaminyltransferase III [GnTIII]), by modifying carbohydrate(s) after the IgG has been expressed, or by expressing an Fc fusion protein in the presence of fucose analogs as enzymatic inhibitors. Other methods for modifying glycoforms of Fc fusion proteins include using glycoengineered strains of yeast (Li et al., 2006, Nature Biotechnology 24(2):210-215), moss (Nechansky et al., 2007, Mol. Immunol. 44(7): 1826-8), and plants (Cox et al., 2006, Nat Biotechnol 24(12):1591-7). In one embodiment, Fc fusions are glycoengineered to alter the level of sialylation. Higher levels of sialylated Fc glycans in Fc molecules can adversely impact functionality (Scallon et al., 2007, Mol Immunol. 44(7): 1524-34), and differences in levels of Fc sialylation can result in modified anti-inflammatory activity (Kaneko et al., 2006, Science 313:670-673). The level of glycosylation of an Fc molecule may also be modified by specific mutations. For example, a mutation at amino acid position 297 or 299 removes the glycosyation at position 297. Such mutants may also be used with Fc fusion proteins.

Other Fc modifications that may be used in Fc fusion proteins include those described in WO88/07054, WO88/07089, U.S. Pat. No. 6,277,375, WO99/051642, WO01/058957, WO2003/074679, WO2004/029207, U.S. Pat. No. 7,317,091 and WO2004/099249.

Moreover, the following Fc variants may also be used for the Fc portion of the Fc fusion proteins described herein. FIG. 25 shows the comparison of the wild type human γ1 constant region Fc (human IgG1Fc; designated as Fc1 in FIG. 25) with Fc4 (SEQ ID NO: 99), Fc5 (SEQ ID NO: 100), Fc6 (SEQ ID NO: 101), Fc7 (SEQ ID NO: 102), Fc8 (SEQ ID NO: 103), Fc9 (SEQ ID NO: 104), Fc10 (SEQ ID NO: 105), Fc11 (SEQ ID NO: 106), Fc12 (SEQ ID NO: 107), Fc13 (SEQ ID NO: 108), Fc14 (SEQ ID NO: 109), Fc15 (SEQ ID NO: 110), Fc16 (SEQ ID NO: 111), Fc17 (SEQ ID NO: 112), Fc18 (SEQ ID NO: 113), Fc19 (SEQ ID NO: 114), Fc21 (SEQ ID NO: 115), Fc22 (SEQ ID NO: 116), Fc23 (SEQ ID NO: 117). In some aspects, an Fc fusion protein described herein comprises an Fc domain having at least 50, 100, or 150 contiguous amino acids of any one of SEQ ID NOs: 99-117. In other embodiments, an Fc fusion protein described herein comprises an Fc domain having from 50-100, 50-150, or 100-150 contiguous amino acids of SEQ ID NOs: 99-117. In yet other embodiments, an Fc fusion protein described herein comprises an Fc domain comprising SEQ ID NOs: 99-117 with from 1-5,1-10, 1-15, 1-20, or 1-25 substitutions or conservative substitutions. The human wild type γ1 constant region sequence was first described by Leroy Hood's group in Ellison et al., Nucl. Acids Res. 10:4071 (1982). EU Index positions 356, 358, and 431 define the G1m γ1 haplotype. The wild type sequence shown here is of the G1m(1), positions 356 and 368, and nG1m(2), position 431, haplotype.

The Fc4 variant contains a γ1 hinge region, but Arg 218 has been introduced in the hinge region to include a BglII restriction enzyme recognition sequence to facilitate cloning. Cys 220 is the Cys residue that forms the disulfide bond to the light chain constant region in an intact immunoglobulin IgG1 protein. Fc4 also includes a Ser for Cys residue substitution to prevent deleterious effects due to the potential presence of an unpaired sulfhydral group. The CH2 region of Fc4 is based on the γ1 CH2 and contains three amino acid substitutions that reduce Fc γ receptor I (FcγRI) binding. These are the substitutions at EU index positions 234, 235, and 237. These substitutions were described by Greg Winter's group in Duncan et al., Nature 332:563 (1988) and were shown in that paper to reduce binding to the Fc γ RI.

Two amino acid substitutions in the complement C1q binding site were introduced to reduce complement fixation. These are the substitutions at EU index positions 330 and 331. The importance, or relevance, of positions 330 and 331 in complement C1q binding (or lack of complement fixation or activation) is described by Sherie Morrison's group in Tao et al., J. Exp. Med. 178:661 (1993) and Canfield and Morrison, J. Exp. Med. 173:1483 (1991). The CH3 region in the Fc4 variant remains identical to the wild type γ1 Fc.

Fc5 is a variant of Fc4. In the Fc5 hinge region the Arg 218 substitution was returned to the wild type Lys 218 residue. Fc5 contains the same Cys 220 to Ser substitution as described above for Fc4. Fc5 contains the same CH2 substitutions as does Fc4, and the Fc5 CH2 region is identical to the wild type γ1 Fc.

The Fc6 variant contains the same hinge region substitutions as Fc5 and contains the same CH2 substitutions as Fc4. The Fc6 CH3 region does not contain a carboxyl terminal lysine residue. This particular Lys residue does not have an assigned EU index number. This lysine is removed to a varying degree from mature immunoglobulins and therefore predominantly not found on circulating antibodies. The absence of this residue on recombinant Fc fusion proteins may result in a more homogeneous product.

The Fc7 variant is identical to the wild type γ1 Fc in the hinge region. Its CH2 region is based on γ1 CH2, but the N-linked carbohydrate attachment site at residue Asn-297 is changed to Gln to produce a deglycosylated Fc. (See e.g., Tao and Morrison (1989) J. Immunol. 143:2595-2601). The CH3 region is identical to the wild type γ1 Fc.

Fc8 variant has a hinge region that is identical to Fc4, and both the CH2 region and the CH3 region are identical to the corresponding wild type γ1 Fc regions.

The Fc9 variant contains a shortened γ1 hinge starting at the Asp residue just carboxy-terminal to the Cys residue involved in disulfide linkage to the light chain. The remaining hinge sequence is identical to the wild type γ1 hinge. Both the CH2 region sequence and the CH3 region sequence are identical to the corresponding regions for the wild-type γ1 Fc.

The Fc10 variant contains the same hinge region substitution as Fc5. Both the CH2 region sequence and the CH3 region sequence are identical to the corresponding regions for the wild-type γ1 Fc.

The Fc11 variant contains the same hinge region substitutions as Fc5. Its CH2 domain is based on γ1 CH2, but contains the substitutions to decrease Fcγ Receptor binding (substitutions at EU index positions 234, 235, and 237). Fc11 is wild type for C1q binding and complement fixation. The CH3 domain of Fc11 is identical to the wild type γ1 CH3.

The Fc12 variant contains a γ1 hinge with Cys 220 Ser, Cys 226 Ser, and Cys 229 Ser substitutions, has a CH2 domain that is identical to that of Fc5, and has wild-type γ1 CH3 domain.

The Fc13 variant contains a γ1 hinge with Cys 220 Ser, Cys 226 Ser, and Cys 229 Ser substitutions, has CH2 domain that is identical to that of Fc5, and has a wild-type γ1 CH3 with Tyr 407 Gly substitution.

The Fc14 variant contains a □1 hinge with Cys 220 Ser, Cys 226 Ser, and Cys 229 Ser substitutions, has a wild-type □1 CH2, and has a wild-type □1 CH3 with Tyr 407 Gly substitution. The Fc15 variant contains a □4 hinge with a Ser 228 Pro substitution to decrease IgG4 "Fab exchange", and has a wild-type □4 CH2 and CH3 domains.

The Fc16 variant contains a γ1 hinge that contains a Cys 220 Ser substitution, has a CH2 domain identical to the γ1 CH2, and has a CH3 domain identical to the wild type γ4 CH3.

The Fc17 variant contains a γ1 hinge with a Cys 220 Ser substitution, has a γ1 CH2 domain with a Phe 243 Ala substitution, and has a CH3 domain identical to the wild type γ1 CH3.

The Fc18 variant contains a γ1 hinge with a Cys 220 Ser substitution, has a γ1 CH2 domain identical to the wild type γ1 CH2, and contains a γ1 CH3 with a H is 435 Ala substitution.

The Fc19 variant contains a hinge identical to Fc5, has a CH2 domain identical to Fc5, except N-linked carbohydrate attachment site at residue Asn-297 is changed to Gln to produce a deglycosylated Fc, and has a CH3 domain identical to the wild type γ1 CH3.

The Fc21 variant contains a γ1 hinge with Cys 220 Ser, Cys 226 Ser, and Cys 229 Ser substitutions, has a CH2 domain identical to Fc5, and has a γ1 CH3 with Phe 405 Ala and Tyr 407 Gly substitutions.

The Fc22 variant contains a γ1 hinge with Cys 220 Ser, Cys 226 Ser, and Cys 229 Ser substitutions, has a CH2 domain identical to Fc1, and has a γ1 CH3 with Phe 405 Ala and Tyr 407 Gly substitutions.

The Fc23 variant contains a γ1 hinge with Cys 220 Ser substitution, has a γ1 CH2 domain with Leu 234 Ala, Leu 235 Glu, Pro 331 Ser substitutions, and a CH3 domain identical to the wild type γ1 Fc.

FIG. 26 shows an alignment of additional Fc variants that may also be used for the Fc portion of the Fc fusion proteins described herein. FIG. 26 shows the comparison of the amino acid sequences of wild type BALB/c mouse γ2a constant region Fc (mFc1; SEQ ID NO: 118) and wild type C57BL/6 mouse γ2c constant region Fc (mFc3; SEQ ID NO: 119) with two mouse Fc variants, mFc2 (SEQ ID NO: 120) and mFc4 (SEQ ID NO: 121), which have little or no effector function. The wild type C57BL/6γ2c was initially isolated and sequenced in the early 1980's and referred to as the mouse γ2a, b allotype (Schreier et al. PNAS 78:4495 (1981)). Subsequent sequence analysis comparisons have shown that the gene corresponds in fact to mouse γ2c (Fukui et al., J. Mol. Cell. Immunol. 1:321 (1984) and Morgado et al., EMBO J. 8:3245 (1989)). Note that several different allotypes do exist for both the γ2a and γ2c sequences. The sequence of mFc1 corresponds to GenBank Accession #V00825 while the sequence of mFc3 corresponds to Gen-Bank Accession #Y10606.

In some aspects, an Fc fusion protein described herein comprises an Fc domain having at least 50, 100, or 150 contiguous amino acids of any one of SEQ ID NOs: 118-121. In other embodiments, an Fc fusion protein described herein comprises an Fc domain having from 50-100, 50-150, or 100-150 contiguous amino acids of SEQ ID NOs: 118-121. In yet other embodiments, an Fc fusion protein described herein comprises an Fc domain comprising SEQ ID NOs: 118-121 with from 1-5, 1-10, 1-15, 1-20, or 1-25 substitutions or conservative substitutions.

The mFc1 variant contains a wild type BALB/c mouse γ2a Fc.

The mFc2 variant contains a BALB/c mouse γ2a hinge with a Gly 219 Ser substitution. The mFc2 CH2 domain contains an amino acid substitution relative to mouse wild type γ2a at position 235 (Leu to Glu) to inactivate binding to FcγRI and FcγRII as described in Duncan et al., Nature 332:563 (1988) and Zheng et al., J. Immunol. 163:4041 (1999). Three additional changes were made at the complement C1q binding site to reduce complement fixation at positions 318, 320 and 322. These substitutions are also described by Zheng et al. The interaction of IgG and C1q was originally identified in Duncan and Winter, Nature 332:738 (1988). The CH3 domain is identical to the wild type mouse γ2a Fc.

The mFc3 variant contains a wild type C57BL/6 mouse γ2c Fc.

The mFc3 variant is identical to mFc3 except that it contains the Gly 219 Ser and Leu 235 Glu substitutions present in mFc2.

Other modifications/substitutions/additions/deletions of the Fc domain will be readily apparent to one skilled in the art.

Polypeptides Comprising $^{10}$Fn3 Domains

In certain embodiments, the Fc fusion proteins provided herein comprise a $^{10}$Fn3 domain, which is a fibronectin based scaffold protein. Fibronectin based scaffold proteins generally make use of a scaffold derived from a fibronectin type III (Fn3) or Fn3-like domain and function in a manner characteristic of natural or engineered antibodies (that is, polyclonal, monoclonal, or single-chain antibodies) and, in addition, possess structural advantages. Specifically, the structure of these antibody mimics has been designed for optimal folding, stability, and solubility, even under conditions that normally lead to the loss of structure and function in antibodies. An example of fibronectin-based scaffold proteins are Adnectins™ (Adnexus, a wholly owned subsidiary of Bristol-Myers Squibb). Fibronectin-based scaffold proteins and Adnectins™ may be monovalent or multivalent.

An Fn3 domain is small, monomeric, soluble, and stable. It lacks disulfide bonds and, therefore, is stable under reducing conditions. The overall structure of Fn3 resembles the Ig fold. Fn3 domains comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. The seven antiparallel β-strands are arranged as two beta sheets that form a stable core, while creating two "faces" composed of the loops that connect the beta or beta-like strands. Loops AB, CD, and EF are located at one face and loops BC, DE, and FG are located on the opposing face. Any or all of loops AB, BC, CD, DE, EF and FG may participate in ligand binding. There are at least 15 different modules of Fn3, and while the sequence homology between the modules is low, they all share a high similarity in tertiary structure.

The amino acid sequence of the naturally occurring human tenth fibronectin type III domain, i.e., the tenth module of human Fn3 ($^{10}$Fn3), is set forth in SEQ ID NO: 1: VSDVPRDLEVVAAT<u>PTSLLISWDAPAVTVRYY</u>-RITYGE<u>TGGNSPVQEFTVPGSKST</u> ATI<u>SGLKPGVD</u>-YTITVYAVTGRGDSPASSKPISINYRT (SEQ ID NO:1) (the AB, CD and EF loops are underlined, and the BC, FG, and DE loops are emphasized in bold).

In SEQ ID NO:1, the AB loop corresponds to residues 15-16, the BC loop corresponds to residues 21-30, the CD loop corresponds to residues 39-45, the DE loop corresponds to residues 51-56, the EF loop corresponds to residues 60-66, and the FG loop corresponds to residues 76-87. See e.g., Xu et al., Chemistry & Biology 2002 9:933-942. The BC, DE and FG loops align along one face of the molecule (sometimes referred to as the "north pole" loops) and the AB, CD and EF loops align along the opposite face of the molecule (sometimes referred to as the "south pole" loops). In SEQ ID NO: 1, beta strand A corresponds to residues 9-14, beta strand B corresponds to residues 17-20, beta strand C corresponds to residues 31-38, beta strand D corresponds to residues 46-50, beta strand E corresponds to residues 57-59, beta strand F corresponds to residues 67-75, and beta strand G corresponds to residues 88-94. The strands are connected to each other through the corresponding loop, e.g., strands A and B are connected via loop AB in the formation of strand A, loop AB, strand B, etc. The first 8 amino acids of SEQ ID NO:1 (italicized above) may be deleted while still retaining binding activity of the molecule. Residues involved in forming the hydrophobic core (the "core amino acid residues") include the amino acids corresponding to the following amino acids of SEQ ID NO: 1: L8, V10, A13, L18, I20, W22, Y32, I34, Y36, F48, V50, A57, I59, L62, Y68, I70, V72, A74, I88, I90 and Y92, wherein the core amino acid residues are represented by the single letter amino acid code followed by the position at which they are located within SEQ ID NO: 1. See e.g., Dickinson et al., J. Mol. Biol. 236: 1079-1092 (1994).

$^{10}$Fn3 domains are structurally and functionally analogous to antibodies, specifically the variable region of an antibody. While $^{10}$Fn3 domains may be described as "antibody mimics" or "antibody-like proteins", they do offer a number of advantages over conventional antibodies. In particular, they exhibit better folding and thermostability properties as compared to antibodies, and they lack disulphide bonds, which are known to impede or prevent proper folding under certain conditions.

The BC, DE, and FG loops of $^{10}$Fn3 domains are analogous to the complementary determining regions (CDRs) from immunoglobulins. Alteration of the amino acid sequence in these loop regions changes the binding specificity of $^{10}$Fn3. $^{10}$Fn3 domains with modifications in the AB, CD and EF loops may also be made in order to produce a molecule that binds to a desired target. The protein sequences outside of the loops are analogous to the framework regions from immunoglobulins and play a role in the structural conformation of the $^{10}$Fn3. Alterations in the framework-like regions of $^{10}$Fn3 are permissible to the extent that the structural conformation is not so altered as to disrupt ligand binding. Methods for generating $^{10}$Fn3 ligand specific binders have been described in PCT Publication Nos. WO 00/034787, WO 01/64942, and WO 02/032925, disclosing high affinity TNFα binders, PCT Publication No. WO 2008/097497, disclosing high affinity VEGFR2 binders, and PCT Publication No. WO 2008/066752, disclosing high affinity IGFIR binders. Additional references discussing $^{10}$Fn3 binders and methods of selecting binders include PCT Publication Nos. WO 98/056915, WO 02/081497, and WO 2008/031098 and U.S. Publication No. 2003186385.

As described above, amino acid residues corresponding to residues 21-30, 51-56, and 76-87 of SEQ ID NO: 1 define the BC, DE and FG loops, respectively. However, it should be understood that not every residue within the loop region needs to be modified in order to achieve a $^{10}$Fn3 binder having strong affinity for a desired target. For example, in many cases, only residues corresponding to amino acids 23-30 of the BC loop and 52-55 of the DE loop are modified and result in high affinity $^{10}$Fn3 binders. Accordingly, in certain embodiments, the BC loop may be defined by amino acids corresponding to residues 23-30 of SEQ ID NO: 1, and the DE loop may be defined by amino acids corresponding to residues 52-55 of SEQ ID NO: 1. Additionally, insertions and deletions in the loop regions may also be made while still producing high affinity $^{10}$Fn3 binders.

Accordingly, in some embodiments, one or more loops selected from BC, DE, and FG may be extended or shortened in length relative to the corresponding loop in wild-type human $^{10}$Fn3. In some embodiments, the length of the loop may be extended by 2-25 amino acids. In some embodiments, the length of the loop may be decreased by 1-11 amino acids. In particular, the FG loop of $^{10}$Fn3 is 12 residues long, whereas the corresponding loop in antibody heavy chains ranges from 4-28 residues. To optimize antigen binding, therefore, the length of the FG loop of $^{10}$Fn3 may be altered in length as well as in sequence to cover the CDR3 range of 4-28 residues to obtain the greatest possible flexibility and affinity in antigen binding. In some embodiments, the integrin-binding motif "arginine-glycine-aspartic acid" (RGD), located at residues 79-81 of SEQ ID NO: 1, may be modified in order to disrupt integrin binding. For example, the RGD sequence may be replaced with SGE or RGE.

As described herein, the non-ligand binding sequences of $^{10}$Fn3, i.e., the "$^{10}$Fn3 scaffold", may be altered provided that the $^{10}$Fn3 retains ligand binding function and/or structural stability. In some embodiments, one or more of Asp 7, Glu 9, and Asp 23 are replaced by another amino acid, such as, for example, a non-negatively charged amino acid residue (e.g., Asn, Lys, etc.). These mutations have been reported to have the effect of promoting greater stability of the mutant $^{10}$Fn3 at neutral pH as compared to the wild-type form (See, PCT Publication No. WO 02/04523). A variety of additional alterations in the $^{10}$Fn3 scaffold that are either beneficial or neutral have been disclosed. See, for example, Batori et al., Protein Eng. 2002 15(12):1015-20; Koide et al., Biochemistry 2001 40(34):10326-33. In some embodiments, the hydrophobic core amino acids are not modified relative to the wild-type sequence. In other embodiments, the following hydrophobic amino acids may be mutated: W22 and/or L62.

The $^{10}$Fn3 scaffold may be modified by one or more conservative substitutions. As many as 5%, 10%, 20% or even 30% or more of the amino acids in the $^{10}$Fn3 scaffold may be altered by a conservative substitution without substantially altering the affinity of the $^{10}$Fn3 for a ligand. In certain embodiments, the scaffold may comprise anywhere from 0-15, 0-10, 0-8, 0-6, 0-5, 0-4, 0-3, 1-15, 1-10, 1-8, 1-6, 1-5, 1-4, 1-3, 2-15, 2-10, 2-8, 2-6, 2-5, 2-4, 5-15, or 5-10 conservative amino acid substitutions. In certain embodiments, the substitutions in the scaffold do not include substitutions of the hydrophobic core amino acid residues. Preferably, the scaffold modification reduces the binding affinity of the $^{10}$Fn3 binder for a ligand by less than 100-fold, 50-fold, 25-fold, 10-fold, 5-fold, or 2-fold. It may be that such changes will alter the immunogenicity of the $^{10}$Fn3 in vivo, and where the immunogenicity is decreased, such changes will be desirable. As used herein, "conservative substitutions" refers to replacement of one amino acid with another amino acid that is physically or functionally similar to the amino acid being replaced. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., Atlas of Protein Sequence and Structure 5:345-352 (1978 & Supp.). Examples of conservative substitutions are substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine.

In some embodiments, the application provides an Fc fusion protein comprising a $^{10}$Fn3 domain, wherein the $^{10}$Fn3 polypeptide is at least 40%, 50%, 55%, 60%, 65%, 70%, 75%, 80%, 85%, or 90% identity to the human $^{10}$Fn3 domain having the amino acid sequence of SEQ ID NO: 1. Much of the variability will generally occur in one or more of the loops. Each of the beta or beta-like strands of a $^{10}$Fn3 domain in a fibronectin based scaffold protein may comprise, consist essentially of, or consist of an amino acid sequence that is at least 80%, 85%, 90%, 95% or 100% identical to the sequence of a corresponding beta or beta-like strand of SEQ ID NO: 1, provided that such variation does not disrupt the stability of the polypeptide in physiological conditions. In exemplary embodiments, the $^{10}$Fn3 domain binds to a desired target with a $K_D$ of less than 500 nM, 100 nM, 10 nM, 1 nM, 500 pM, 100 pM or less. In exemplary embodiments, the fibronectin based scaffold protein binds specifically to a target that is not bound by a wild-type $^{10}$Fn3 domain, particularly the wild-type human $^{10}$Fn3 domain.

In some embodiments, the application provides an Fc fusion protein comprising a $^{10}$Fn3 domain, wherein the $^{10}$Fn3 polypeptide has an amino acid sequence at least 80, 85, 90, 95, 98, or 100% identical to the non-loop regions of SEQ ID NO: 1, wherein at least one loop selected from BC, DE, and FG is altered. In some embodiments, the altered BC loop has up to 10 amino acid substitutions, up to 4 amino acid deletions, up to 10 amino acid insertions, or a combination thereof. In some embodiments, the altered DE loop has up to 6 amino acid substitutions, up to 4 amino acid deletions, up to 13 amino acid insertions, or a combination thereof. In some embodiments, the FG loop has up to 12 amino acid substitutions, up to 11 amino acid deletions, up to 25 amino acid insertions, or a combination thereof.

In some embodiments, the application provides Fc fusion proteins comprising a $^{10}$Fn3 domain, wherein the $^{10}$Fn3 domain comprises a loop, AB; a loop, BC; a loop, CD; a loop, DE; a loop, EF; and a loop, FG; and has at least one loop selected from loop BC, DE, and FG with an altered amino acid sequence relative to the sequence of the corresponding loop of the human $^{10}$Fn3 domain. In some embodiments, the BC and FG loops are altered. In some embodiments, the BC, DE, and FG loops are altered, i.e., the $^{10}$Fn3 domain comprises non-naturally occurring loops. By "altered" is meant one or more amino acid sequence alterations relative to a template sequence (i.e., the corresponding human fibronectin domain) and includes amino acid additions, deletions, and substitutions. Altering an amino acid sequence may be accomplished through intentional, blind, or spontaneous sequence variation, generally of a nucleic acid coding sequence, and may occur by any technique, for example, PCR, error-prone PCR, or chemical DNA synthesis.

In certain embodiments, the application provides Fc fusion proteins comprising a $^{10}$Fn3 domain, wherein the $^{10}$Fn3 domain can be defined generally by the following core amino acid sequence: <u>EVVAAT</u>(X)$_a$<u>SLLI</u>(X)$_x$ <u>YYRITYGE</u>(X)$_b$<u>QEFTV</u>(X)$_y$<u>ATI</u>(X)$_c$<u>DYTITVYAV</u>(X)$_z$ <u>ISINYRT</u> (SEQ ID NO:2).

In SEQ ID NO:2, the AB loop is represented by $X_a$, the CD loop is represented by $X_b$, the EF loop is represented by $X_c$, the BC loop is represented by $X_x$, the DE loop is represented by $X_y$, and the FG loop is represented by $X_z$. X represents any amino acid and the subscript following the X represents an integer of the number of amino acids. In particular, a may be anywhere from 1-15, 2-15, 1-10, 2-10, 1-8, 2-8, 1-5, 2-5, 1-4, 2-4, 1-3, 2-3, or 1-2 amino acids; and b, c, x, y and z may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids. In preferred embodiments, a is 2 amino acids, b is 7 amino acids, c is 7 amino acids, x is 9 amino acids, y is 6 amino acids, and z is 12 amino acids. The sequences of the beta strands (underlined in SEQ ID NO: 2) may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 2. In an exemplary embodiment, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 2. In certain embodiments, the hydrophobic core amino acid residues are fixed and any substitutions, conservative substitutions, deletions or additions occur at residues other than the core amino acid residues. In exemplary embodiments, the BC, DE, and FG loops as represented by $(X)_x$, $(X)_y$, and $(X)_z$, respectively, are replaced with polypeptides comprising BC, DE and FG loop sequences that bind to specific targets.

In certain embodiments, the application provides Fc fusion proteins comprising a $^{10}$Fn3 domain, wherein the $^{10}$Fn3 domain can be defined generally by the sequence: <u>EVVAATPTSLLI</u>(X)$_x$<u>YYRITYGETGGNSPVQEFTV</u>(X)$_y$ <u>ATISGLKPGVDYTITVYAV</u>(X)$_z$<u>ISINYRT</u> (SEQ ID NO:3).

In SEQ ID NO:3, the BC loop is represented by $X_x$, the DE loop is represented by $X_y$, and the FG loop is represented by $X_z$. X represents any amino acid and the subscript following the X represents an integer of the number of amino acids. In particular, x, y and z may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids. In preferred embodiments, x is 9 amino acids, y is 6 amino acids, and z is 12 amino acids. The sequences of the beta strands and south pole loops (underlined in SEQ ID NO: 3) may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions and south pole loops relative to the corresponding amino acids shown in SEQ ID NO: 3. In an exemplary embodiment, the sequences of the beta strands and south pole loops may have anywhere from 0 to 10, from 0 to 8, from 0 to 6, from 0 to 5, from 0 to 4, from 0 to 3, from 0 to 2, or from 0 to 1 conservative substitutions across all 7 scaffold regions and south pole loops relative to the corresponding amino acids shown in SEQ ID NO: 3. In certain embodiments, the core amino acid residues are fixed and any substitutions, conservative substitutions, deletions or additions occur at residues other than the core amino acid residues. In exemplary embodiments, the BC, DE, and FG loops as represented by $(X)_x$, $(X)_y$, and $(X)_z$, respectively, are replaced with polypeptides comprising BC, DE and FG loop sequences that bind to specific targets.

A $^{10}$Fn3 domain as described herein may optionally contain a modified N- and/or C-terminal sequence. For example, with reference to SEQ ID NO:2 or 3, the $^{10}$Fn3 domain may comprise an N-terminal extension and/or a C-terminal tail as described further below.

In certain embodiments, the $^{10}$Fn3 domain as shown in SEQ ID NO: 2 or 3 may optionally comprise an N-terminal extension of from 1-20, 1-15, 1-10, 1-8, 1-5, 1-4, 1-3, 1-2, or 1 amino acids in length. Exemplary N-terminal extensions include (represented by the single letter amino acid code) M, MG, G, MGVSDVPRDL (SEQ ID NO: 4), VSDVPRDL (SEQ ID NO: 5), and GVSDVPRDL (SEQ ID NO: 6), or N-terminal truncations of any one of SEQ ID NOs: 4, 5 or 6. Other suitable N-terminal extensions include, for example, $X_n$SDVPRDL (SEQ ID NO: 7), $X_n$DVPRDL (SEQ ID NO: 8), $X_n$VPRDL (SEQ ID NO: 9), $X_n$PRDL (SEQ ID NO: 10), $X_n$RDL (SEQ ID NO: 11), $X_n$DL (SEQ ID NO: 12), or $X_n$L, wherein n=0, 1 or 2 amino acids, wherein when n=1, X is Met or Gly, and when n=2, X is Met-Gly. When a Met-Gly sequence is added to the N-terminus of a $^{10}$Fn3 domain, the M will usually be cleaved off, leaving a G at the N-terminus.

In certain embodiments, the $^{10}$Fn3 domain as shown in SEQ ID NO: 2 or 3 may optionally comprise a C-terminal tail of from 1-20, 1-15, 1-10, 1-8, 1-5, or 1-4 amino acids in length. Specific examples of tail sequences include, for example, polypeptides comprising, consisting essentially of, or consisting of, EIEK (SEQ ID NO: 13), EGSGC (SEQ ID NO: 14), EIEKPCQ (SEQ ID NO: 15), EIEKPSQ (SEQ ID NO: 16), EIEKP (SEQ ID NO: 17), EIEKPS (SEQ ID NO: 18), EIEKPC (SEQ ID NO: 19), EIDKPSQ (SEQ ID NO: 20), or EIDKPSQLE (SEQ ID NO: 21). In certain embodiments, the $^{10}$Fn3 domain comprises a C-terminal tail comprising a sequence $X(ED)_n$, wherein n is an integer from 2-10, 2-8, 2-5, 3-10, 3-8, 3-7, 3-5, 4-7, or wherein n is 2, 3, 4, 5, 6, 7, 8, 9 or 10, and X is optional, and when present is an E, I or EI. Such ED repeat tails may enhance solubility and/or reduce aggregation of the $^{10}$Fn3 domain. In exemplary embodiments, the C-terminal tail comprises, consists essentially of, or consists of the amino acid sequence of SEQ ID NO: 15. In preferred embodiments, the C-terminal sequences lack DK sequences.

In certain embodiments, the fibronectin based scaffold proteins comprise a $^{10}$Fn3 domain having both an N-terminal extension and a C-terminal tail.

In certain embodiments, a $^{10}$Fn3 domain is a domain set forth in WO 2012/016245.

Multivalent Fibronectin Based Scaffold Proteins

In certain embodiments, the application provides an Fc fusion protein comprising a polypeptide having two or more $^{10}$Fn3 domains, e.g., a multivalent fibronectin based scaffold protein. For example, a multivalent fibronectin based scaffold protein may comprise 2, 3 or more $^{10}$Fn3 domains that are covalently associated. In exemplary embodiments, the fibronectin based scaffold protein is a bispecific or dimeric protein comprising two $^{10}$Fn3 domains. In certain embodiments, a multivalent fibronectin based protein scaffold comprises a first $^{10}$Fn3 domain that binds to a first target molecule and a second $^{10}$Fn3 domain that binds to a second target molecule. The first and second target molecules may be the same or different target molecules. When the first and second target molecules are the same, the $^{10}$Fn3 domains, i.e., the binding loops, may be the same or different. Furthermore, when the first and second $^{10}$Fn3 domains bind to the same target, they may bind to the same or different epitopes on the target.

In exemplary embodiments, each $^{10}$Fn3 domain of a multivalent fibronectin based protein scaffold binds to a desired target with a $K_D$ of less than 1 mM, 100 μM, 10 μM, 1 μM, 500 nM, 100 nM, 10 nM, 1 nM, 500 pM, 100 pM or less. In exemplary embodiments, each $^{10}$Fn3 domain of a multivalent fibronectin based protein scaffold binds specifically to a target that is not bound by a wild-type $^{10}$Fn3 domain, particularly the wild-type human $^{10}$Fn3 domain. In exemplary embodiments, none of the $^{10}$Fn3 domains of a multivalent fibronectin based protein scaffold bind to an integrin protein.

In the case of multivalent fibronectin based scaffold proteins, preferably none of the $^{10}$Fn3 domains comprise a C-terminal tail containing a DK sequence. In exemplary embodiments, a multivalent fibronectin based scaffold protein comprises two or more $^{10}$Fn3 domains, wherein each domain comprises a C-terminal tail that does not contain a DK sequence. In certain embodiments, a multivalent fibronectin based scaffold protein comprises two or more $^{10}$Fn3 domains, wherein each domain comprises a C-terminal tail that does not contain a DK sequence.

The $^{10}$Fn3 domains in a multivalent fibronectin based scaffold protein may be connected by a peptide linker. Exemplary peptide linkers include peptides having from 1-20, 1-15, 1-10, 1-8, 1-5, 1-4, 1-3, or 1-2 amino acids. Suitable linkers for joining the $^{10}$Fn3 domains are those which allow the separate domains to fold independently of each other forming a three dimensional structure that permits high affinity binding to a target molecule. In some embodiments, suitable linkers that allow the separate domains or portions to fold independently of each other comprise glycine-serine based linkers, glycine-proline based linkers and proline-alanine based linkers. The Examples described in WO 2009/142773 demonstrate that Fn3 domains joined via these linkers retain their target binding function. In some embodiments, the linker is a glycine-serine based linker. These linkers comprise glycine and serine residues and may be between 8 and 50, 10 and 30, and 10 and 20 amino acids in length. Examples of such linkers include GSGSGSGSGS (SEQ ID NO: 32), GSGSGSGSGSGS (SEQ ID NO: 33), GSGSGSGSGSGSGSGSGS (SEQ ID NO: 34), GGGGSGGGGSGGGGS (SEQ ID NO: 35), GGGGSGGGGSGGGGSGGGGSGGGGS (SEQ ID NO: 80), and GGGGSGGGGSGGGSG (SEQ ID NO: 36). In some embodiments, the linker is a glycine-proline based linker. These linkers comprise glycine and proline residues and may be between 3 and 30, 10 and 30, and 3 and 20 amino acids in length. Examples of such linkers include GPG (SEQ ID NO: 39), GPGPGPG (SEQ ID NO: 40) and GPGPGPGPGPG (SEQ ID NO: 41). In some embodiments, the linker is a proline-alanine based linker. These linkers comprise proline and alanine residues and may be between 3 and 30, 10 and 30, 3 and 20 and 6 and 18 amino acids in length. Examples of such linkers include PAPAPA (SEQ ID NO: 42), PAPAPAPAPAPA (SEQ ID NO: 43) and PAPAPAPAPAPAPAPA (SEQ ID NO: 44). In other embodiments, the linker comprises the sequence PSTSTST (SEQ ID NO: 71). It is contemplated, that the optimal linker length and amino acid composition may be determined by routine experimentation based on the teachings provided herein. In exemplary embodiments, the linker does not contain any DK sequences.

Vectors & Polynucleotides

In other embodiments, the application provides nucleic acids encoding any of the various Fc fusion proteins disclosed herein. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA*, 100(2):438-442 (Jan. 21, 2003); Sinclair et al., *Protein Expr. Purif.*, 26(I):96-105 (October 2002); Connell, N.D., *Curr. Opin. Biotechnol.*, 12(5):446-449 (October 2001); Makrides et al., *Microbiol Rev.*, 60(3):512-538 (September 1996); and Sharp et al., *Yeast*, 7(7):657-678 (October 1991).

General techniques for nucleic acid manipulation are described for example in Sambrook et al., *Molecular Cloning: A Laboratory Manual*, 2nd Edition, Vols. 1-3, Cold Spring Harbor Laboratory Press (1989), or Ausubel, F. et al., *Current Protocols in Molecular Biology*, Green Publishing and Wiley-Interscience, New York (1987) and periodic updates, herein incorporated by reference. Generally, the DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The Fc fusion proteins described herein may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. An exemplary N-terminal leader sequence for production of polypeptides in a mammalian system is METDTLLLWVLLLWVPGSTG (SEQ ID NO: 29), which is removed by the host cell following expression.

For prokaryotic host cells that do not recognize and process a native signal sequence, the signal sequence is substituted by a prokaryotic signal sequence selected, for example, from the group of the alkaline phosphatase, penicillinase, 1 pp, or heat-stable enterotoxin II leaders.

For yeast secretion the native signal sequence may be substituted by, e.g., the yeast invertase leader, a factor leader (including *Saccharomyces* and *Kluyveromyces* alpha-factor leaders), or acid phosphatase leader, the *C. albicans* glucoamylase leader, or the signal described in U.S. Pat. No. 5,631,144. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 micron plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tracycline, (b) complement auxotrophic deficiencies, or (c) supply critical nutrients not available from complex media, e.g., the gene encoding D-alanine racemase for Bacilli.

Expression and cloning vectors usually contain a promoter that is recognized by the host organism and is operably linked to the nucleic acid encoding the protein disclosed herein, e.g., a fibronectin-based scaffold protein. Promoters suitable for use with prokaryotic hosts include the phoA promoter, beta-lactamase and lactose promoter systems, alkaline phosphatase, a tryptophan (trp) promoter system, and hybrid promoters such as the tan promoter. However, other known bacterial promoters are suitable. Promoters for use in bacterial systems also will contain a Shine-Dalgarno (S.D.) sequence operably linked to the DNA encoding the protein disclosed herein. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tall to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

Transcription of a DNA encoding proteins disclosed herein by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature,* 297:17-18 (1982) on enhancing elements for activation of eukaryotic promoters. The enhancer may be spliced into the vector at a position 5' or 3' to the peptide-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of mRNA encoding the protein disclosed herein. One useful transcription termination component is the bovine growth hormone polyadenylation region. See WO94/11026 and the expression vector disclosed therein.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual,* (Elsevier, New York (1985)), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae,* may also be used for production of polypeptides. Various mammalian or insect cell culture systems can also be employed to express recombinant proteins. Baculovirus systems for production of heterologous proteins in insect cells are reviewed by Luckow et al. (*Bio/Technology,* 6:47 (1988)). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Protein Production

In other aspects, the application provides host cells containing vectors encoding the Fc fusion proteins described herein, as well as methods for producing the Fc fusion proteins described herein. Host cells may be transformed with the herein-described expression or cloning vectors for protein production and cultured in conventional nutrient media modified as appropriate for inducing promoters, selecting transformants, or amplifying the genes encoding the desired sequences. Host cells useful for high-throughput protein production (HTPP) and mid-scale production include the HMS174-bacterial strain. The host cells used to produce the proteins disclosed herein may be cultured in a variety of media. Commercially available media such as Ham's F10 (Sigma), Minimal Essential Medium ((MEM), (Sigma)), RPMI-1640 (Sigma), and Dulbecco's Modified Eagle's Medium ((DMEM), Sigma)) are suitable for culturing the host cells. In addition, may of the media described in Ham et al., *Meth. Enzymol.,* 58:44 (1979), Barites et al., *Anal. Biochem.,* 102:255 (1980), U.S. Pat. Nos. 4,767,704, 4,657,866, 4,927,762, 4,560,655, 5,122,469, 6,048,728, 5,672,502, or U.S. Pat. No. RE 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The Fc fusion proteins provided herein can also be produced using cell-translation systems. For such purposes the nucleic acids encoding the fusion protein must be modified to allow in vitro transcription to produce mRNA and to allow cell-free translation of the mRNA in the particular cell-free system being utilized (eukaryotic such as a mammalian or yeast cell-free translation system or prokaryotic such as a bacterial ceil-free translation system.

The Fc fusion proteins disclosed herein can also be produced by chemical synthesis (e.g., by the methods described in *Solid Phase Peptide Synthesis,* 2nd Edition, The Pierce Chemical Co., Rockford, Ill. (1984)). Modifications to the Fc fusion proteins can also be produced by chemical synthesis.

The Fc fusion proteins disclosed herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, get filtration, gel permeation chromatography, affinity chromatography, electrophoresis, countercurrant distribution or any combinations of these. After purification, polypeptides may be exchanged into different buffers and/or concentrated by any of a variety of methods known to the art, including, but not limited to, filtration and dialysis.

The purified Fc fusion proteins is preferably at least 85% pure, or preferably at least 95% pure, and most preferably at least 98% pure. Regardless of the exact numerical value of the purity, the Fc fusion protein is sufficiently pure for use as a pharmaceutical product.

Exemplary Uses

In one aspect, the application provides Fc fusion proteins that are useful as diagnostic or therapeutic agents. Fc fusion proteins useful as diagnostic agents may be labeled with a detectable moiety. The Fc fusion proteins may be used for a variety of diagnostic applications. The detectable moiety can be any one which is capable of producing, either directly or indirectly, a detectable signal. For example, the detectable moiety may be a radioisotope, such as H3, C14, C13, P32, S35, or I131; a fluorescent or chemiluminescent compound, such as fluorescein isothiocyanate, rhodamine, or luciferin; or an enzyme, such as alkaline phosphatase, beta-galactosidase or horseradish peroxidase.

Any method known in the art for conjugating a protein to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982). In vitro methods, include conjugation chemistry well know in the art including chemistry compatible with proteins, such as chemistry for specific amino acids, such as Cys and Lys. In order to link a detectable moiety to an Fc protein, a linking group or reactive group is used. Suitable linking groups are well known in the art and include disulfide groups, thioether groups, acid labile groups, photolabile groups, peptidase labile groups and esterase labile groups. Preferred linking groups are disulfide groups and thioether groups depending on the application. For polypeptides without a Cys amino acid, a Cys can be engineered in a location to allow for activity of the protein to exist while creating a location for conjugation.

Fc fusion proteins linked with a detectable moiety are useful for in vitro or in vivo imaging. The polypeptide may be linked to a radio-opaque agent or radioisotope, administered to a subject, preferably into the bloodstream, and the presence and location of the labeled protein in the subject may be assayed. This imaging technique is useful, for example, in the staging and treatment of malignancies when the Fc fusion protein binds to a target associated with cancer. The Fc fusion protein may be labeled with any moiety that is detectable in a subject, whether by nuclear magnetic resonance, radiology, or other detection means known in the art.

Fc fusion proteins also are useful as affinity purification agents. In this process, the Fc fusion proteins are immobilized on a suitable support, such as Sephadex resin or filter paper, using methods well known in the art.

Fc fusion proteins can be employed in any known assay method, such as competitive binding assays, direct and indirect sandwich assays, and immunoprecipitation assays (Zola, Monoclonal Antibodies: A Manual of Techniques, pp. 147-158 (CRC Press, Inc., 1987)).

In certain aspects, the disclosure provides methods for detecting a target molecule in a sample. A method may comprise contacting the sample with an Fc fusion protein described herein, wherein said contacting is carried out under conditions that allow the Fc fusion protein-target complex formation; and detecting said complex, thereby detecting said target in said sample. Detection may be carried out using any technique known in the art, such as, for example, radiography, immunological assay, fluorescence detection, mass spectroscopy, or surface plasmon resonance. The sample will often by a biological sample, such as a biopsy, and particularly a biopsy of a tumor, or a suspected tumor, where the Fc fusion protein binds to a target associated with cancer. The sample may be from a human or other mammal. The Fc fusion protein may be labeled with a labeling moiety, such as a radioactive moiety, a fluorescent moiety, a chromogenic moiety, a chemiluminescent moiety, or a hapten moiety. The Fc fusion protein may be immobilized on a solid support.

In one aspect, the application provides Fc fusion proteins useful in the treatment of disorders. The diseases or disorders that may be treated will be dictated by the identity of the protein fused to the Fc domain. Exemplary therapeutic proteins that may be bound to an Fc domain include, for example, interferon alpha (for treating hepatitis), L-asparaginase (for the treatment of acute lymphoblastic leukemia), or granulocyte colony-stimulating factor (for treatment of cancer chemotherapy induced neutropenia). In certain embodiments, the Fc fusion proteins described herein comprise an antibody, or fragment thereof, such as, for example, and anti-TNF-alpha antibody (for the treatment of autoimmune diseases like rheumatoid arthritis or Crohn's disease). In an exemplary embodiment, the Fc fusion protein described herein comprise a polypeptide comprising $^{10}$Fn3 domain, including, for example, a polypeptide comprising a $^{10}$Fn3 domain that binds to a target such as tumor necrosis factor alpha (TNF-alpha), delta-like protein 4 (DLL4), interleukin 17 (IL-17), proprotein convertase subtilisin kexin type 9 (PCSK9), pregnane X receptor (PXR), epidermal growth factor receptor (EGFR), insulin-like growth factor 1 receptor (IGF-1R), vascular endothelial growth factor receptor (VEGFR2), and interleukin 23 (IL-23). $^{10}$Fn3 domains that bind to TNF-alpha may be used to treat autoimmune disorders such as rheumatoid arthritis, inflammatory bowel disease, psoriasis, and asthma; $^{10}$Fn3 domains that bind to IL-17 may be used to treat asthma; $^{10}$Fn3 domains that bind to DLL4, EGFR, VEGFR2 or IGF-1R may be used to treat hyperproliferative disorders or diseases associated with unwanted angiogenesis, such as cancers or tumors; and $^{10}$Fn3 domains that bind to PCSK9 may be used to treat atherosclerosis, hypercholesterolemia and other cholesterol related diseases.

The application also provides methods for administering Fc fusion proteins to a subject. In some embodiments, the subject is a human. In some embodiments, the Fc fusion proteins are pharmaceutically acceptable to a mammal, in particular a human. A "pharmaceutically acceptable" composition refers to a composition that is administered to an animal without significant adverse medical consequences. Examples of pharmaceutically acceptable compositions include compositions that are essentially endotoxin or pyrogen free or have very low endotoxin or pyrogen levels.

Formulation and Administration

The application further provides pharmaceutically acceptable compositions comprising the Fc fusion proteins described herein. Therapeutic formulations comprising Fc fusion proteins are prepared for storage by mixing the described proteins having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations herein may also contain more than one active compounds as necessary for the particular indication being treated, preferably those with complementary activities that do not adversely affect each other. Such molecules are suitably present in combination in amounts that are effective for the purpose intended.

The Fc fusion proteins may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the fibronectin based scaffold proteins described herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

While the skilled artisan will understand that the dosage of each Fc fusion protein will be dependent on the identity of the protein, the preferred dosages can range from about 10 mg/square meter to about 2000 mg/square meter, more preferably from about 50 mg/square meter to about 1000 mg/square meter.

For therapeutic applications, the Fc fusion proteins are administered to a subject, in a pharmaceutically acceptable dosage form. They can be administered intravenously as a bolus or by continuous infusion over a period of time, by intramuscular, subcutaneous, intra-articular, intrasynovial, intrathecal, oral, topical, or inhalation routes. The protein may also be administered by intratumoral, peritumoral, intralesional, or perilesional routes, to exert local as well as systemic therapeutic effects. Suitable pharmaceutically acceptable carriers, diluents, and excipients are well known and can be determined by those of skill in the art as the clinical situation warrants. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose. The methods of the present invention can be practiced in vitro, in vivo, or ex vivo.

Administration of Fc fusion proteins, and one or more additional therapeutic agents, whether co-administered or administered sequentially, may occur as described above for therapeutic applications. Suitable pharmaceutically acceptable carriers, diluents, and excipients for co-administration will be understood by the skilled artisan to depend on the identity of the particular therapeutic agent being co-administered.

When present in an aqueous dosage form, rather than being lyophilized, the Fc fusion protein typically will be formulated at a concentration of about 0.1 mg/ml to 100 mg/ml, although wide variation outside of these ranges is permitted. For the treatment of disease, the appropriate dosage of Fc fusion proteins will depend on the type of disease to be treated, the severity and course of the disease, whether the Fc fusion proteins are administered for preventive or therapeutic purposes, the course of previous therapy, the patient's clinical history and response to the Fc fusion protein, and the discretion of the attending physician. The Fc fusion protein is suitably administered to the patient at one time or over a series of treatments.

Sequence listing

WT $^{10}$Fn3 Sequence
VSDVPRDLEVVAAT<u>PTSLLI</u>SWDAPAVTVRYYRITYGE<u>TGGN</u>SPVQEFTVPGSKST
ATI<u>SGLKPGV</u>DYTITVYAVTGRGDSPASSKPISINYRT (SEQ ID NO: 1)

WT Core $^{10}$Fn3 Sequence
EVVAAT(X)$_a$<u>SLLI</u>(X)$_b$<u>YYRITYGE</u>(X)$_c$<u>QEFTV</u>(X)$_d$<u>ATI</u>(X)$_e$<u>DYTITVYAV</u>(X)$_f$<u>ISINYRT</u>
(SEQ ID NO: 2)

EVVAATPTSLLI(X)$_b$<u>YYRITYGETGGNSPVQEFTV</u>(X)$_d$<u>ATISGLKPGVDYTITVYAV</u>(X)$_f$<u>IS</u>
INYRT (SEQ ID NO: 3)

MGVSDVPRDL (SEQ ID NO: 4)

VSDVPRDL (SEQ ID NO: 5)

GVSDVPRDL (SEQ ID NO: 6)

-continued

Sequence listing $X_n$SDVPRDL (SEQ ID NO: 7)

$X_n$DVPRDL (SEQ ID NO: 8)

$X_n$VPRDL (SEQ ID NO: 9)

$X_n$PRDL (SEQ ID NO: 10)

$X_n$RDL (SEQ ID NO: 11)

$X_n$DL (SEQ ID NO: 12)

EIEK (SEQ ID NO: 13)

EGSGC (SEQ ID NO: 14)

EIEKPCQ (SEQ ID NO: 15)

EIEKPSQ (SEQ ID NO: 16)

EIEKP (SEQ ID NO: 17)

EIEKPS (SEQ ID NO: 18)

EIEKPC (SEQ ID NO: 19)

EIDKPSQ (SEQ ID NO: 20)

EIDKPSQLE (SEQ ID NO: 21)

Human IgG1 Constant Region
*ASTKGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKVEPKSC*DKTHTCPPCPAPELLGGPSVFLFP
PKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSRDELTK
NQVSLTCLVKGFYPSDIAVEWESNGQPENNYKTTPPVLDSDGSFFLYSKLTVDKSRWQ
QGNVFSCSVMHEALHNHYTQKSLSLSPGK (SEQ ID NO: 22)

DKTHTCPPCPAPELLG (SEQ ID NO: 23)

EPKSSDKTHTCPPCPAPELLGGPS
(SEQ ID NO: 24; core hinge region underlined)

EPKSSDKTHTCPPCPAPELLGGSS
(SEQ ID NO: 25; core hinge region underlined)

EPKSSGSTHTCPPCPAPELLGGSS
(SEQ ID NO: 26; core hinge region underlined)

DKTHTCPPCPAPELLGGPS
(SEQ ID NO: 27; core hinge region underlined)

DKTHTCPPCPAPELLGGSS
(SEQ ID NO: 28, core hinge region underlined)

METDTLLLWVLLLWVPGSTG (SEQ ID NO: 29)

PRD460 Amino Acid Sequence
*GVSDVPRDLEVVAATPTSLLISWVPPSDDYGYYRITYGETGGNSPVQEFTVPIGKGTATISGLK
PGVDYTITVYAVEFPWPHAGYYHRPISINYRTEI*EPKSSGSTHTCPPCPAPELLGGSSVFLPPP
KPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO: 30)

CH2 and CH3 Regions of Human IgG1
VFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVDKS
RWQQGNVFSCSVMHEALHNHYTQKSLSLSPGK (SEQ ID NO: 31)

GSGSGSGSGS (SEQ ID NO: 32)

GSGSGSGSGSGS (SEQ ID NO: 33)

GSGSGSGSGSGSGSGSGS (SEQ ID NO: 34)

| Sequence listing |
|---|
| GGGGSGGGGSGGGGS (SEQ ID NO: 35) |
| GGGGSGGGGSGGGGSGGGGSGGGGS (SEQ ID NO: 80) |
| GGGGSGGGGSGGGSG (SEQ ID NO: 36) |
| AGGGGSG (SEQ ID NO: 37) |
| AGGGGSGG (SEQ ID NO: 38) |
| GPG (SEQ ID NO: 39) |
| GPGPGPG (SEQ ID NO: 40) |
| GPGPGPGPGPG (SEQ ID NO: 41) |
| PAPAPA (SEQ ID NO: 42) |
| PAPAPAPAPAPA (SEQ ID NO: 43) |
| PAPAPAPAPAPAPAPAPA (SEQ ID NO: 44) |
| QPDEPGGS (SEQ ID NO: 45) |
| ELQLEESAAEAQDGELD (SEQ ID NO: 46) |
| TVAAPS (SEQ ID NO: 47) |
| QPDEPGGSG (SEQ ID NO: 48) |
| ELQLEESAAEAQDGELDG (SEQ ID NO: 49) |
| TVAAPSG (SEQ ID NO: 50) |
| SCSVADWQMPPPYVVLDLPQETLEEETPGAN (SEQ ID NO: 51) |
| SCCVADWQMPPPYVVLDLPQETLEEETPGAN (SEQ ID NO: 52) |
| DWQMPPPYVVLDLPQETLEEETPGAN (SEQ ID NO: 53) |
| SCCVADWQMPPPYVVLDLPQETLEEETPGAN (SEQ ID NO: 54) |
| YLAMTPLIPQSKDENSDDYTTFDDVGS (SEQ ID NO: 55) |
| ELDVCVEEAEGEAPW (SEQ ID NO: 56) |
| ELQLEESCAEAQDGELDG (SEQ ID NO: 57) |
| EGEVSADEEGFEN (SEQ ID NO: 58) |
| KPTHVNVSVVMAEVDGTCY (SEQ ID NO: 59) |
| KPTHVNVSVVMAEVDGTCY (SEQ ID NO: 60) |
| YVTDHGPMK (SEQ ID NO: 61) |
| PTLYNVSLVMSDTAGTCY (SEQ ID NO: 62) |
| SXSVADWQMPPPYVVLDLPQETLEEETPGAN, wherein X is serine, alanine or glycine (SEQ ID NO: 63) |
| SXXVADWQMPPPYVVLDLPQETLEEETPGAN, wherein each X is independently selected from serine, alanine or glycine (SEQ ID NO: 64) |
| SXXVADWQMPPPYVVLDLPQETLEEETPGAN, wherein each X is independently selected from serine, alanine or glycine (SEQ ID NO: 65) |
| ELDVXVEEAEGEAPW, wherein X is serine, alanine or glycine (SEQ ID NO: 66) |
| ELQLEESXAEAQDGELDG, wherein X is serine, alanine or glycine (SEQ ID NO: 67) |

-continued

Sequence listing

KPTHVNVSVVMAEVDGTXY,
wherein X is serine, alanine or glycine
(SEQ ID NO: 68)

KPTHVNVSVVMAEVDGTXY,
wherein X is serine, alanine or glycine
(SEQ ID NO: 69)

PTLYNVSLVMSDTAGTXY,
wherein X is serine, alanine or glycine
(SEQ ID NO: 70)

PSTSTST (SEQ ID NO: 71)

ATI-1174 Amino Acid Sequence
MGVSDVPRDLEVVAATPTSLLISWVPPSDDYGYYRITYGETGGNSPVQEFTVPIGKGTA
TISGLKPGVDYTITVYAVEFPWPHAGYYHRPISINYRTEIEKPCQ (SEQ ID NO: 72)

ATI-1174 Nucleic Acid Sequence
ATGGGAGTTTCTGATGTGCCGCGCGACCTGGAAGTGGTTGCTGCCACCCCCACCAG
CCTGCTGATCAGCTGGGTCCCGCCTTCAGATGATTACGGTTATTACCGCATCACTTA
CGGCGAAACAGGAGGCAATAGCCCTGTCCAGGAGTTCACTGTGCCTATTGGTAAAG
GAACAGCTACCATCAGCGGCCTTAAACCTGGCGTTGATTATACCATCACTGTGTATG
CTGTCGAGTTTCCGTGGCCACATGCTGGTTACTATCATCGGCCAATTTCCATTAATT
ACCGCACAGAAATTGAGAAACCATGCCAGTG (SEQ ID NO: 73)

ATI-1081 Amino Acid Sequence
MGVSDVPRDLEVVAATPTSLLISWVPPSDDYGYYRITYGETGGNSPVQEFTVPIGKGTA
TISGLKPGVDYTITVYAVEFPWPHAGYYHRPISINYRTEIDKPSQ (SEQ ID NO: 74)

ATI-1081 Nucleic Acid Sequence
ATGGGAGTTTCTGATGTGCCGCGCGACCTGGAAGTGGTTGCTGCCACCCCCACCAG
CCTGCTGATCAGCTGGGTCCCGCCTTCAGATGATTACGGTTATTACCGCATCACTTA
CGGCGAAACAGGAGGCAATAGCCCTGTCCAGGAGTTCACTGTGCCTATTGGTAAAG
GAACAGCTACCATCAGCGGCCTTAAACCTGGCGTTGATTATACCATCACTGTGTATG
CTGTCGAGTTTCCGTGGCCACATGCTGGTTACTATCATCGGCCAATTTCCATTAATT
ACCGCACAGAAATTGACAAACCATCCCAGCACCATCACCACCACCAC (SEQ ID NO: 75)

ATI-1114 Amino Acid Sequence
MGVSDVPRDLEVVAATPTSLLISWVPPSDDYGYYRITYGETGGNSPVQEFTVPIGKGTA
TISGLKPGVDYTITVYAVEFPWPHAGYYHRPISINYRTGSGC (SEQ ID NO: 76)

ATI-1114 Nucleic Acid Sequence
ATGGGAGTTTCTGATGTGCCGCGCGACCTGGAAGTGGTTGCTGCCACCCCCACCAG
CCTGCTGATCAGCTGGGTCCCGCCTTCAGATGATTACGGTTATTACCGCATCACTTA
CGGCGAAACAGGAGGCAATAGCCCTGTCCAGGAGTTCACTGTGCCTATTGGTAAAG
GAACAGCTACCATCAGCGGCCTTAAACCTGGCGTTGATTATACCATCACTGTGTATG
CTGTCGAGTTTCCGTGGCCACATGCTGGTTACTATCATCGGCCAATTTCCATTAATT
ACCGCACAGGTAGCGGTTGCCACCATCACCACCATCAC (SEQ ID NO: 77)

ATI-972 Amino Acid Sequence
MGVSDVPRDLEVVAATPTSLLISWPPPSHGYGYYRITYGETGGNSPVQEFTVPPGKGTA
TISGLKPGVDYTITVYAVEYPYKHSGYYHRPISINYRTEIDKPCQ (SEQ ID NO: 78)

ATI-972 Nucleic Acid Sequence
ATGGGAGTTTCTGATGTGCCGCGCGACCTGGAAGTGGTTGCTGCCACCCCCACCAG
CCTGCTGATCAGCTGGCCGCCGCCGTCTCATGGTTACGGTTATTACCGCATCACTTA
CGGCGAAACAGGAGGCAATAGCCCTGTCCAGGAGTTCACTGTGCCGCCTGGTAAAG
GTACAGCTACCATCAGCGGCCTTAAACCTGGCGTTGATTATACCATCACTGTGTATG
CTGTCGAATACCCGTACAAACATTCTGGTTACTACCATCGTCCAATTTCCATTAATT
ACCGCACAGAAATTGACAAACCATGCCAGCACCATCACCACCACCAC (SEQ ID NO: 79)

QPDEP (SEQ ID NO: 81)

PVPPPPP (SEQ ID NO: 82)

EDEDEDEDEDE (SEQ ID NO: 83)

DLPQETLEEETPGA (SEQ ID NO: 84)

VPSTPPTPSPST (SEQ ID NO: 85)

ELQLEESAAEAQEGELE (SEQ ID NO: 86)

ESPKAQASSVPTAQPQAE (SEQ ID NO: 87)

-continued

| Sequence listing |
|---|

PAVPPP (SEQ ID NO: 88)

EPKSSDKTHTCPPCP (SEQ ID NO: 89)

VPSTPPTPSPSTG (SEQ ID NO: 90)

VPSTPPTPSPSTPPTPSPSG (SEQ ID NO: 91)

GRGGEEKKKEKEKEEG (SEQ ID NO: 92)

GRGGEEKKKEKEKEEQEERETKTPG (SEQ ID NO: 93)

ESPKAQASSG (SEQ ID NO: 94)

ESPKAQASSVPTAQPQAEG (SEQ ID NO: 95)

SVEEKKKEKEKEEQEERETKTPG (SEQ ID NO: 96)

PSVEEKKKEKEKEEQEERETKTPG (SEQ ID NO: 97)

GSVEEKKKEKEKEEQEERETKTPG (SEQ ID NO: 98)

Fc4
EPRSSDKTHTCPPCPAPEAEGAPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPSSI
EKTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK
(SEQ ID NO: 99)

Fc5
EPKSSDKTHTCPPCPAPEAEGAPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPSSI
EKTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK
(SEQ ID NO: 100)

Fc6
EPKSSDKTHTCPPCPAPEAEGAPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPSSI
EKTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPG (SEQ
ID NO: 101)

Fc7
EPKSCDKTHTCPPCPAPELLGGPSVFLFPPKPKDTLMISRTPEVTCVVVDVSHEDPEVKF
NWYVDGVEVHNAKTKPREEQYQSTYRVVSVLTVLHQDWLNGKEYKCKVSNKALPAP
IEKTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK
(SEQ ID NO: 102)

Fc8
EPRSSDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK
(SEQ ID NO: 103)

Fc9
DKTHTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK (SEQ ID
NO: 104)

Fc10
EPKSSDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK
(SEQ ID NO: 105)

Fc11
EPKSSDKTHTCPPCPAPEAEGAPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK
(SEQ ID NO: 106)

Fc12
EPKSSDKTHTSPPSPAPEAEGAPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPSSIE
KTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK (SEQ
ID NO: 107)

Fc13
EPKSSDKTHTSPPSPAPEAEGAPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPSSIE
KTISKAKGQPREPQVYTLPPSRDELTKNQVSLTCLVKGFYPSDIAVEWESNGQPENNYK
TTPPVLDSDGSFFLGSKLTVDKSRWQQGNVFSCSVMHEALHNHYTQKSLSLSPGK (SEQ
ID NO: 108)

Fc14
EPKSSDKTHTSPPSPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYK
TTPPVLDSDGSFFLGSKLTVDKSRWQQGNVFSCSVMHEALHNHYTQKSLSLSPGK (SEQ
ID NO: 109)

Fc15
ESKYGPPCPPCPAPEFLGGPSVFLFPPKPKDTLMISRTPEVTCVVVDVSQEDPEVKFNWY
VDGVEVHNAKTKPREEQFNSTYRVVSVLTVLHQDWLNGKEYKCKVSNKGLPSSIEKTI
SKAKGQPREPQVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLSLGK (SEQ ID
NO: 110)

Fc16
EPKSSDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAP
IEKTISKAKGQPREPQVYTLPPSQEEMTKNQVSLTCLVKGFYPSDIAVEWESNGQPENN
YKTTPPVLDSDGSFFLYSRLTVDKSRWQEGNVFSCSVMHEALHNHYTQKSLSLSLGK
(SEQ ID NO: 111)

Fc17
EPKSSDKTHTCPPCPAPELLGGPSVFLAPPKPKDTLMISRTPEVTCVVVDVSHEDPEVKF
NWYVDGVEVHNAKTKPREEQYNSTYRVVSVLTVLHQDWLNGKEYKCKVSNKALPSSI
EKTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK
(SEQ ID NO: 112)

Fc18
EPKSSDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNAYTQKSLSLSPGK
(SEQ ID NO: 113)

Fc19
EPKSSDKTHTCPPCPAPEAEGAPSVFLFPPKPKDTLMISRTPEVTCVVVDVSHEDPEVKF
NWYVDGVEVHNAKTKPREEQYQSTYRVVSVLTVLHQDWLNGKEYKCKVSNKALPSSI
EKTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK
(SEQ ID NO: 114)

Fc21
EPKSSDKTHTSPPSPAPEAEGAPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPSSIE
KTISKAKGQPREPQVYTLPPSRDELTKNQVSLTCLVKGFYPSDIAVEWESNGQPENNYK
TTPPVLDSDGSFALGSKLTVDKSRWQQGNVFSCSVMHEALHNHYTQKSLSLSPGK
(SEQ ID NO: 115)

Fc22
EPKSSDKTHTSPPSPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYK
TTPPVLDSDGSFALGSKLTVDKSRWQQGNVFSCSVMHEALHNHYTQKSLSLSPGK
(SEQ ID NO: 116)

Fc23
EPKSSDKTHTCPPCPAPEAGGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAS
IEKTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK
(SEQ ID NO: 117)

Sequence listing mFc1
EPRGPTIKPCPPCKCPAPNLLGGPSVFIFPPKIKDVLMISLSPIVTCVVVDVSEDDPDVQIS
WFVNNVEVHTAQTQTHREDYNSTLRVVSALPIQHQDWMSGKEFKCKVNNKDLPAPIE
RTISKPKGSVRAPQVYVLPPPEEEMTKKQVTLTCMVTDFMPEDIYVEWTNNGKTELNY
KNTEPVLDSDGSYFMYSKLRVEKKNWVERNSYSCSVVHEGLHNHHTTKSFSRTPGK
(SEQ ID NO: 118)

mFc3
EPRVPITQNPCPPLKECPPCAAPDLLGGPSVFIFPPKIKDVLMISLSPMVTCVVVDVSEDD
PDVQISWFVNNVEVHTAQTQTHREDYNSTLRVVSALPIQHQDWMSGKEFKCKVNNRA
LPSPIEKTISKPRGPVRAPQVYVLPPPAEEMTKKEFSLTCMITGFLPAEIAVDWTSNGRTE
QNYKNTATVLDSDGSYFMYSKLRVQKSTWERGSLFACSVVHEGLHNHLTTKTISRSLG
K (SEQ ID NO: 119)

mFc2
EPRSPTIKPCPPCKCPAPNLEGGPSVFIFPPKIKDVLMISLSPIVTCVVVDVSEDDPDVQIS
WFVNNVEVHTAQTQTHREDYNSTLRVVSALPIQHQDWMSGKAFACAVNNKDLPAPIE
RTISKPKGSVRAPQVYVLPPPEEEMTKKQVTLTCMVTDFMPEDIYVEWTNNGKTELNY
KNTEPVLDSDGSYFMYSKLRVEKKNWVERNSYSCSVVHEGLHNHHTTKSFSRTPGK
(SEQ ID NO: 120)

mFc4
EPRSPITQNPCPPLKECPPCAAPDLEGGPSVFIFPPKIKDVLMISLSPMVTCVVVDVSEDD
PDVQISWFVNNVEVHTAQTQTHREDYNSTLRVVSALPIQHQDWMSGKAFACAVNNRA
LPSPIEKTISKPRGPVRAPQVYVLPPPAEEMTKKEFSLTCMITGFLPAEIAVDWTSNGRTE
QNYKNTATVLDSDGSYFMYSKLRVQKSTWERGSLFACSVVHEGLHNHLTTKTISRSLG
K (SEQ ID NO: 121)

PRD289
GVSDVPRDLEVVAATPTSLLISWRPPIHAYGYYRITYGETGGNSPVQEFTVPIVEGTATIS
GLKPGVDYTITVYAVEYTFKHSGYYHRPISINYRTEIEPKSSGSTHTCPPCPAPELLGGSS
VFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVDKS
RWQQGNVFSCSVMHEALHNHYTQKSLSLSPG (SEQ ID NO: 122)

PRD292
EPKSSGSTHTCPPCPAPELLGGSSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGAGGG
GSGGGVSDVPRDLEVVAATPTSLLISWRPPIHAYGYYRITYGETGGNSPVQEFTVPIVEGT
ATISGLKPGVDYTITVYAVEYTFKHSGYYHRPISINYRTEI (SEQ ID NO: 123)

PRD290
GVSDVPRDLEVVAATPTSLLISWSPPANGYGYYRITYGETGGNSPVQEFTVPVGRGTATI
SGLKPGVDYTITVYAVEYTYKGSGYYHRPISINYRTEIEPKSSGSTHTCPPCPAPELLGGSS
SVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDK
SRWQQGNVFSCSVMHEALHNHYTQKSLSLSPG (SEQ ID NO: 124)

PRD293
EPKSSGSTHTCPPCPAPELLGGSSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGAGGG
GSGGGVSDVPRDLEVVAATPTSLLISWSPPANGYGYYRITYGETGGNSPVQEFTVPVGRG
TATISGLKPGVDYTITVYAVEYTYKGSGYYHRPISINYRTEI (SEQ ID NO: 125)

PRD713
GVSDVPRDLEVVAATPTSLLISWGHYPLHVRYYRITYGETGGNSPVQEFTVPPRSHTATI
SGLKPGVDYTITVYAVTYYAQENYKEIPISINYRTEIEPKSSGSTHTCPPCPAPELLGGSSV
FLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDE
LTKNQVSLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 126)

PRD239
EPKSSGSTHTCPPCPAPELLGGSSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGAGGG
GSGGGVSDVPRDLEVVAATPTSLLISWGHYPLHVRYYRITYGETGGNSPVQEFTVPPRSH
TATISGLKPGVDYTITVYAVTYYAQENYKEIPISINYRTEAS (SEQ ID NO: 127)

```
                           Sequence listing

C7FL-Fc (PRD1309)
GSVSDVPRDLEVVAATPTSLLISWRHPHFPTRYYRITYGETGGNSPVQEFTVPLQPPTATI
SGLKPGVDYTITVYAVTDGRNGRLLSIPISINYRTEIEPKSSDKTHTCPPCPAPELLGGSSV
FLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDE
LTKNQVSLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 128)

C7FL-Fc (PRD1308)
GSVSDVPRDLEVVAATPTSLLISWRHPHFPTRYYRITYGETGGNSPVQEFTVPLQPPTATI
SGLKPGVDYTITVYAVTDGRNGRLLSIPISINYRTEIEPKSSDKTHTCPPCPAPELLGGPSV
FLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDE
LTKNQVSLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 129)
```

EXAMPLES

The invention now being generally described will be more readily understood by reference to the following examples which are included merely for purposes of illustration of certain aspects and embodiments of the present invention, and are not intended to limit the invention in any way.

Example 1

Anti-PCSK9 Adnectin Clones

[10]Fn3 domains that bound with affinity to PCSK9 were identified using the ProFusion method. See e.g., WO02/032925.

ATI-1174 is a pegylated anti-PCSK9 Adnectin having the following amino acid sequence: MGVSDVPRDLEV-VAATPTSLLISWVPPSDDYGYYRITYGETG-GNSPVQEFTVPIGKGTA TISGLKPGVDYTITVYAVEF-PWPHAGYYHRPISINYRTEIEKPCQ (SEQ ID NO: 72).

ATI-1174 is encoded by the following nucleotide sequence:
ATGGGAGTTTCTGATGTGCCGCGCGACCTG-GAAGTGGTTGCTGCCACCCCA CCAGCCTGCT-GATCAGCTGGGTCCCGCCTTCAGATGATTACGGTT-ATTACCGCATCA
CTTACGGCGAAACAGGAGGCAATAGCCCTGTCCA-GGAGTTCACTGTGCCTATTGGT AAAGGAACAGC-TACCATCAGCGGCCTTAAACCTGGCGTTGAT-TATACCATCACTGT
GTATGCTGTCGAGTTTCCGTGGCCACATGCTGGT-TACTATCATCGGCCAATTTCCAT TAATTACCGCACA-GAAATTGAGAAACCATGCCAGTG (SEQ ID NO: 73).

ATI-1081 is an anti-PCSK9 Adnectin having the following amino acid sequence and a 6×His tag:
MGVSDVPRDLEVVAATPTSLLISWVPPSDDY-GYYRITYGETGGNSPVQEFTVPIG KGTATISGLK-PGVDYTITVYAVEFPWPHAGYYHRPIS-INYRTEIDKPSQ (SEQ ID NO: 74).

ATI-1081 is encoded by the following nucleotide sequence:
ATGGGAGTTTCTGATGTGCCGCGCGACCTG-GAAGTGGTTGCTGCCACCCCA CCAGCCTGCT-GATCAGCTGGGTCCCGCCTTCAGATGATTACGGTT-ATTACCGCATCA
CTTACGGCGAAACAGGAGGCAATAGCCCTGTCCA-GGAGTTCACTGTGCCTATTGGT AAAGGAACAGC-TACCATCAGCGGCCTTAAACCTGGCGTTGAT-TATACCATCACTGT
GTATGCTGTCGAGTTTCCGTGGCCACATGCTGGT-TACTATCATCGGCCAATTTCCAT TAATTACCGCACA-GAAATTGACAAACCATCCCAGCACCATCACCAC-CACCAC (SEQ ID NO: 75).

ATI-1114 is a pegylated anti-PCSK9 adnectin that is a derivative of ATI-1081 having a different C-terminal tail sequence and a 6×His tag:
MGVSDVPRDLEVVAATPTSLLISWVPPSDDY-GYYRITYGETGGNSPVQEFTVPIG KGTATISGLK-PGVDYTITVYAVEFPWPHAGYYHRPISINYRTGSGC (SEQ ID NO: 76).

ATI-1114 is encoded by the following nucleotide sequence:
ATGGGAGTTTCTGATGTGCCGCGCGACCTG-GAAGTGGTTGCTGCCACCCCA CCAGCCTGCT-GATCAGCTGGGTCCCGCCTTCAGATGATTACGGTT-ATTACCGCATCA
CTTACGGCGAAACAGGAGGCAATAGCCCTGTCCA-GGAGTTCACTGTGCCTATTGGT AAAGGAACAGC-TACCATCAGCGGCCTTAAACCTGGCGTTGAT-TATACCATCACTGT
GTATGCTGTCGAGTTTCCGTGGCCACATGCTGGT-TACTATCATCGGCCAATTTCCAT TAATTACCGCACA-GGTAGCGGTTGCCACCATCACCACCATCAC (SEQ ID NO: 77).

ATI-972 is a biotinylated anti-PCSK9 adnectin with 6-histidine c-terminus and biotinylation at cysteine, and having the following sequence:
MGVSDVPRDLEVVAATPTSLLISWPPPSHGY-GYYRITYGETGGNSPVQEFTVPPG KGTATISGLK-PGVDYTITVYAVEYPYKHSGYYHRPISINYRTEIDK-PCQ (SEQ ID NO: 78).

ATI-972 is encoded by the following nucleotide sequence:
ATGGGAGTTTCTGATGTGCCGCGCGACCTG-GAAGTGGTTGCTGCCACCCCA CCAGCCTGCT-GATCAGCTGGCCGCCGCCGTCTCATGGTTACGGTT-ATTACCGCATCA
CTTACGGCGAAACAGGAGGCAATAGCCCTGTCCA-GGAGTTCACTGTGCCGCCTGGT AAAGGTACAGC-TACCATCAGCGGCCTTAAACCTGGCGTTGAT-TATACCATCACTGTG
TATGCTGTCGAATACCCGTACAAACATTCTGGTTAC-TACCATCGTCCAATTTCCATT AATTACCGCACA-GAAATTGACAAACCATGCCAGCACCATCACCAC-CACCAC (SEQ ID NO: 79).

PRD460 is an anti-PCSK9 Adnectin-Fc fusion proteins having the following amino acid sequence: GVSD-VPRDLEVVAATPTSLLISWVPPSDDYGYYRIT-YGETGGNSPVQEFTVPIGKGTATISGLK PGVDYTIT- VYAVEFPWPHAGYYHRPISINYRTEI EPKSSGSTHTCPPCPAPELLGGSSVFLFPP KPKDTLMISRTPEVTCVVVDVSHEDPEVKFN- WYVVDGVEVHNAKTKPREEQYNSTYRV VSVLTVL- HQDWLNGKEYKCKVSNKALPAPIEKTISKAK- GQPREPQVYTLPPSRDELTKN QVSLTCLVKGFYPSDIAVEWESNGQPENNYKTTPPV- LDSDGSFFLYSKLTVDKSRWQQ GNVFSCSVM- HEALHNHYTQKSLSLSPGK (SEQ ID NO: 30). The $^{10}$Fn3 domain that binds PCSK9 is shown in italics; the hinge sequence is underlined; and the CH2 and CH3 regions shown in regular text are derived from IgG1.

The anti-PCSK9 adnectins may be expressed in *E. coli* with an N-terminal methionine, or in mammalian cells with the following leader sequence: METDTLLLWVLLL-WVPGSTG (SEQ ID NO: 29).

Example 2

Protein Production and Purification

Midscale Expression and Purification of Insoluble Fibronectin-Based Scaffold Protein Binders For expression of insoluble clones, the clone(s), followed by the HIS$_6$tag, are cloned into a pET9d (EMD Bioscience, San Diego, Calif.) vector and are expressed in *E. coli* HMS174 cells. Twenty ml of an inoculum culture (generated from a single plated colony) is used to inoculate 1 liter of LB medium containing 50 µg/ml carbenicillin and 34 µg/ml chloromphenicol. The culture is grown at 37° C. until $A_{600}$ 0.6-1.0. After induction with 1 mM isopropyl-β-thiogalactoside (IPTG) the culture is grown for 4 hours at 30° C. and is harvested by centrifugation for 30 minutes at ≥10,000 g at 4° C. Cell pellets are frozen at −80° C. The cell pellet is resuspended in 25 ml of lysis buffer (20 mM NaH$_2$PO$_4$, 0.5 M NaCl, 1× Complete Protease Inhibitor Cocktail-EDTA free (Roche), 1 mM PMSF, pH 7.4) using an Ultra-turrax homogenizer (IKA works) on ice. Cell lysis is achieved by high pressure homogenization (≥18,000 psi) using a Model M-110S MICROFLUIDIZER® (Microfluidics). The insoluble fraction is separated by centrifugation for 30 minutes at 23,300 g at 4° C. The insoluble pellet recovered from centrifugation of the lysate is washed with 20 mM sodiumphosphate/500 mM NaCl, pH7.4. The pellet is resolubilized in 6.0M guanidine hydrochloride in 20 mM sodium phosphate/500M NaCl pH 7.4 with sonication followed by incubation at 37 degrees for 1-2 hours. The resolubilized pellet is filtered to 0.45 µm and loaded onto a Histrap column equilibrated with the 20 mM sodium phosphate/500M NaCl/6.0M guanidine pH 7.4 buffer. After loading, the column is washed for an additional 25 CV with the same buffer. Bound protein is eluted with 50 mM Imidazole in 20 mM sodium phosphate/500 mM NaCl/6.0M guan-HCl pH7.4. The purified protein is refolded by dialysis against 50 mM sodium acetate/150 mM NaCl pH 4.5.

Midscale Expression and Purification of Soluble Fibronectin-Base Scaffold Protein Binders For expression of soluble clones, the clone(s), followed by the HIS$_6$tag, were cloned into a pET9d (EMD Bioscience, San Diego, Calif.) vector and were expressed in *E. coli* HMS174 cells. Twenty ml of an inoculum culture (generated from a single plated colony) was used to inoculate 1 liter of LB medium containing 50 µg/ml carbenicillin and 34 µg/ml chloromphenicol. The culture was grown at 37° C. until $A_{600}$ 0.6-1.0. After induction with 1 mM isopropyl-β-thiogalactoside (IPTG), the culture was grown for 4 hours at 30° C. and was harvested by centrifugation for 30 minutes at ≥10,000 g at 4° C. Cell pellets were frozen at −80° C. The cell pellet was resuspended in 25 ml of lysis buffer (20 mM NaH$_2$PO$_4$, 0.5 M NaCl, 1× Complete Protease Inhibitor Cocktail-EDTA free (Roche), 1 mM PMSF, pH 7.4) using an Ultra-turrax homogenizer (IKA works) on ice. Cell lysis was achieved by high pressure homogenization (18,000 psi) using a Model M-110S MICROFLUIDIZER® (Microfluidics). The soluble fraction was separated by centrifugation for 30 minutes at 23,300 g at 4° C. The supernatant was clarified via 0.45 µm filter. The clarified lysate was loaded onto a Histrap column (GE) pre-equilibrated with the 20 mM sodium phosphate/500M NaCl pH 7.4. The column was then washed with 25 column volumes of the same buffer, followed by 20 column volumes of 20 mM sodium phosphate/500M NaCl/25 mM Imidazole, pH 7.4 and then 35 column volumes of 20 mM sodium phosphate/500M NaCl/40 mM Imidazole, pH 7.4. Protein was eluted with 15 column volumes of 20 mM sodium phosphate/500M NaCl/500 mM Imidazole, pH 7.4, fractions were pooled based on absorbance at $A_{280}$ and were dialyzed against 1×PBS, 50 mM Tris, 150 mM NaCl. pH 8.5 or 50 mM NaOAc; 150 mM NaCl; pH4.5. Any precipitate was removed by filtering at 0.22 µm.

Fc fusions can be made in mammalian cells or in *E. coli*.

Example 3

PRD460 K$_D$ by SPR

A vector encoding PRD460 was transfected into HEK-293 6E cells using polyethylenimine (PEI). The cells were grown at 37° C. for 5 days with 80% humidification and 5% CO$_2$. The cells were then pelleted, the supernatant was passed through a 0.22 um filter and then loaded onto to a ProteinA column. The column was washed with PBS and the protein was eluted with 20 mM Gylcine, 150 mM NaCl pH 2.8. The eluted protein was concentrated and passed over a superdex200 column in 50 mM MES, 100 mM NaCl pH 5.8.

The binding characteristics were characterized by Surface Plasmon Resonance (SPR). Anti-human antibody was immobilized on a Biacore chip, and PRD460 was captured on the chip surface. Varying concentrations of hPCSK9 were placed into the flow solution using MgCl2 (3 M) for chip regeneration between cycles. For comparison, ATI-1081 was captured on an anti-H is antibody immobilized on a Biacore chip. Duplicate experiments for PRD460 were performed on different days. Kinetic determinations were performed at 25° C. Evaluation of the kinetic parameters was performed using the 1:1 Binding algorithm on the Biacore Evaluation software.

Under these conditions, ATI-1081 bound to human PCSK9 with a dissociation constant (K$_D$) of 6.7 nM at 25° C. and PRD460 bound to human PCSK9 with a dissociation constant (K$_D$) of 3.29+/−0.55 nM at 25° C., indicating equivalent binding affinity of the Fc and non-Fc formatted versions of ATI1081 (Table 1). The off-rate determinations using this assay format may be artificially limited by the off-rate of the captured ligand from the immobilized capture antibody, thus the assay format using direct immobilization of PCSK9 is a more accurate reflection of dissociation constant (K$_D$) for ATI-1081.

TABLE 1

Kinetic parameters for PRD460 and ATI-1081 against captured human PCSK9

|  | ka (1/Ms) | kd (1/s) | KD (nM) |
|---|---|---|---|
| PRD460 | 3.75 +/− 0.7E+04 | 1.21 +/− 0.05E−04 | 3.29 +/− 0.55 |
| ATI-1081 | 3.65E+04 | 2.45E−04 | 6.7 |

Example 4

PCSK9 Binding FRET Assays

Two fluorescence resonance energy transfer (FRET) based assays were used to determine the competitive binding potency of PRD460 and other adnectins to hPCSK9. The PCSK9:EGFA FRET assay measures the binding of PCSK9 to the LDLR, using a soluble epidermal growth factor precursor homology domain-A (EGFA) peptide and recombinant human PCSK9. The PCSK9:ATI972 FRET assay measures competitive displacement by adnectins of the biotinylated adnectin, ATI-972, from PCSK9.

In the PCSK9:EGFA FRET assay (at 5 nM PCSK9), PRD460 completely and potently displaced EGFA from the PCSK9 binding site with EC50=0.7 nM (FIG. 1, left panel). PRD460 was more potent in this assay than either ATI-1174 (EC50=1.9 nM) or ATI-1081 (EC50=3.7 nM) (FIG. 1). The greater apparent potency of PRD460 in this assay may be explained by bivalent (2:1) binding of adnectin PRD460 to PCSK9 (theoretically) compared to monovalent (1:1) binding by ATI-1081 and ATI-1174.

Using the PCSK9:ATI-972 FRET assay (at 5 nM human PCSK9), PRD460 inhibited with EC50=0.3 nM, compared to 0.8 nM for ATI-1114 and 2.8 nm for ATI-1081 (FIG. 2). These findings indicate that PRD460 potently displaced the biotinylated adnectin ATI-972 from its binding site on PCSK9. The higher potency of PRD460 relative to ATI-1081 and ATI-1174 is consistent with bivalent binding by PRD460.

Example 5

Inhibition of PCSK9-Induced LDLR Depletion in HepG2 Cells

Human PCSK9 promotes the depletion of LDLR from the surface of HepG2 cells. Pre-incubation of PCSK9 with PCSK9 adnectins inhibits PCSK9 binding to LDLR and prevents the depletion of LDLR from the cell surface. This assay was used to measure the potency of ATI-1081, ATI-1174 and PRD460 to inhibit PCSK9 induced depletion of LDLR from the cell surface.

A dilution series of PCSK9 adnectins were pre-incubated with 10 nM human PCSK9 for 1 hr at 37 degrees, the pre-incubated mixture was added to HepG2 cells, and the cells were incubated for 24 hours. Following this incubation, the level of LDLR on HepG2 cells was measured using FACS analysis. The percentage of inhibition of PCSK9-induced LDLR depletion was calculated and graphed (FIG. 2). In this assay ATI-1081, ATI-1174, and PRD460 inhibited PCSK9 with comparable EC50's (9 nM, 8 nM and 6 nM respectively) although a leftward-shift of the response curve was consistently observed for PRD460. These EC50's represent the limit of the assay.

This assay was also used to determine the importance of Fc orientation on the biological activity of Fc-$^{10}$Fn3 fusion proteins. To this end, the ability of 1784F03 (no Fc), 1784F03-Fc (X-Fc orientation, wherein X is the $^{10}$Fn3 domain) and Fc-1784F03 (Fc-X orientation) to inhibit PCSK9 induced depletion of LDLR from the cell surface was assessed. The ability of 1813E02 (no Fc), 1813E02-Fc (X-Fc orientation) and Fc-1813E02 (Fc-X orientation) to inhibit PCSK9 induced depletion of LDLR from the cell surface was also assessed.

Figure 16:
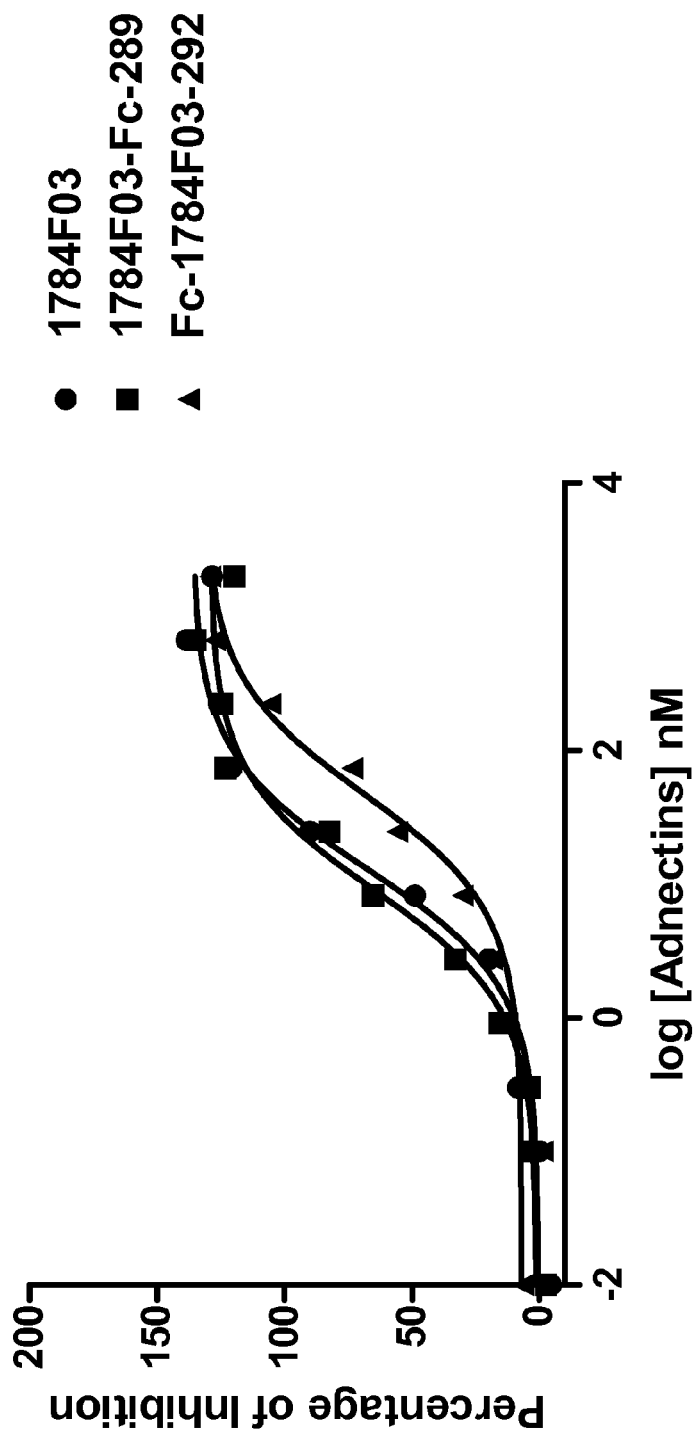
FIG. 16. Inhibition of PCSK9-induced LDLR depletion from HepG2 cell surface by anti-PCSK9 Fc-$^{10}$Fn3 fusion proteins.
Figure 17:
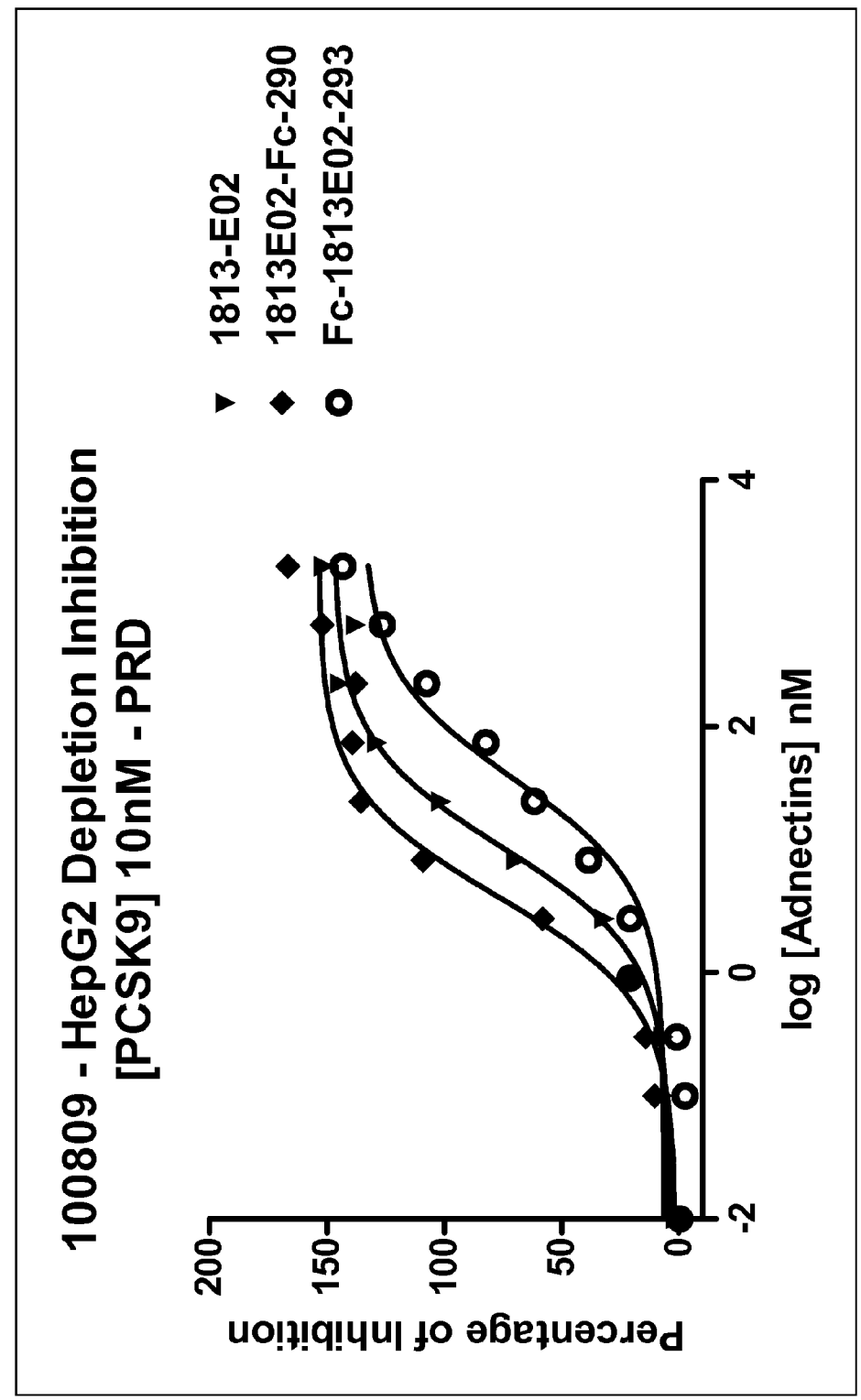
FIG. 17. Inhibition of PCSK9-induced LDLR depletion from HepG2 cell surface by anti-PCSK9 Fc-$^{10}$Fn3 fusion proteins.

A dilution series was prepared and pre-incubated as above with 10 nM human PCSK9 for 1 hr at 37 degrees, then added to HepG2 cells, and the cells were incubated for 24 hours. Following this incubation, the level of LDLR on HepG2 cells was measured using FACS analysis. The percentage of inhibition of PCSK9-induced LDLR depletion was calculated and graphed (FIGS. 16-17, and Tables 17-18). In this assay, 1784F03, 1784F03-Fc, 1813E02 and 1813E02-Fc inhibited PCSK9 with comparable IC50's (13 nM, 9 nM, 10 nM and 4 nM, respectively), whereas Fc-1784F03 and Fc-1813E02 had significantly higher IC50's (47 nM and 37 nM, respectively). Therefore, these results indicate that the X-Fc orientation may be important for PCSK9 $^{10}$Fn3 domains to retain their biological activity when fused to an Fc moiety.

TABLE 17

Summary of HepG2 depletion inhibition by 1784F03, 1784F03-Fc and Fc-1784F03

|  | 1784F03 | 1784F03-Fc (PRD 289) | Fc-1784F03 (PRD 292) |
|---|---|---|---|
| IC50 | 13.24 | 9.150 | 47.77 |
| $R^2$ | 0.9934 | 0.9871 | 0.9879 |

TABLE 18

Summary of HepG2 depletion inhibition by 1813E02, 1813E02-Fc and Fc-1813E02

|  | 1813-E02 | 1813E02-Fc PRD 290 | Fc-1813E02 PRD 293 |
|---|---|---|---|
| IC50 | 10.55 | 4.201 | 37.78 |
| $R^2$ | 0.9961 | 0.9871 | 0.9745 |

Example 6

PCSK9 Cell Entry Assay in HepG2 Cells

Figure 3:
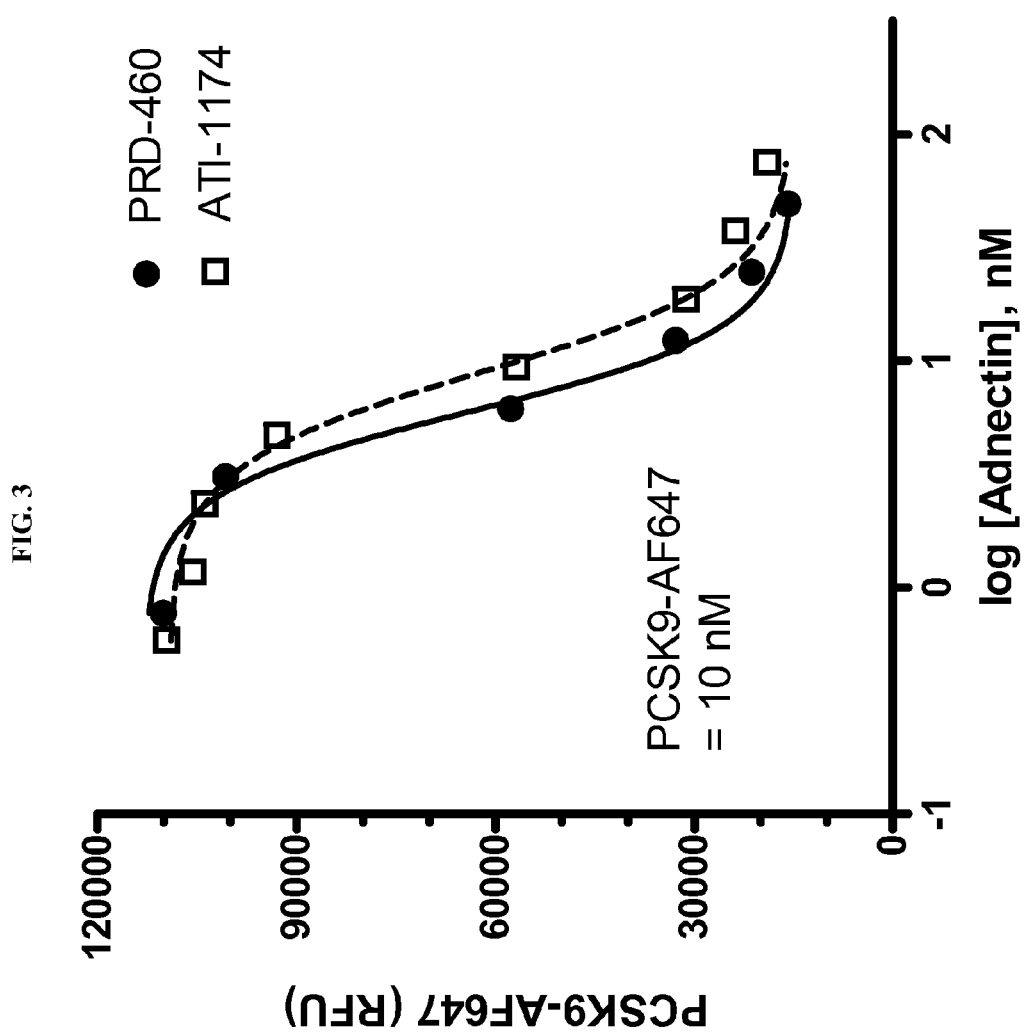
FIG. 3. Inhibition of PCSK9-AF647 cell entry in HepG2 cells by anti-PCSK9 Adnectins.

PCSK9 binding to the LDLR on the surface of hepatocytes results in co-internalization of the LDLR-PCSK9 complex during LDLR endocytosis, leading to enhanced degradation of the LDLR. A cell-based assay was developed to measure LDLR-dependent cellular entry of fluorescent PCSK9. Human PCSK9 was covalently labeled using the fluorophore Alexa Fluor-647(AF647). PCSK9-AF647 was incubated with HepG2 cells with or without PCSK9-adnectins and the intracellular fluorescence was quantified by high content fluorescent microscopy and image analysis (Cellomics). Dependence of PCSK9-AF647 cell entry on LDLR endocytosis was established in preliminary experiments. HepG2 cells were incubated with 10 nM PCSK9-AF647 and varying levels of adnectins for 4 hrs at 37 degrees. In this assay, potent inhibition of PCSK9-AF647 intracellular fluorescence was observed for PRD460 (EC50=6 nM) as well as for ATI-1174 (EC50=10 nM) (FIG. 3). These findings indicate that adnectin PRD460 and ATI-1174 effectively and equivalently blocked the binding of PCSK9 to cell surface LDLR in a human hepatic-derived cell line in culture, thereby reducing the internalization of PCSK9-AF647 during LDLR endocytosis.

Example 7

In Vivo Transgenic Mouse Study

Figure 4:
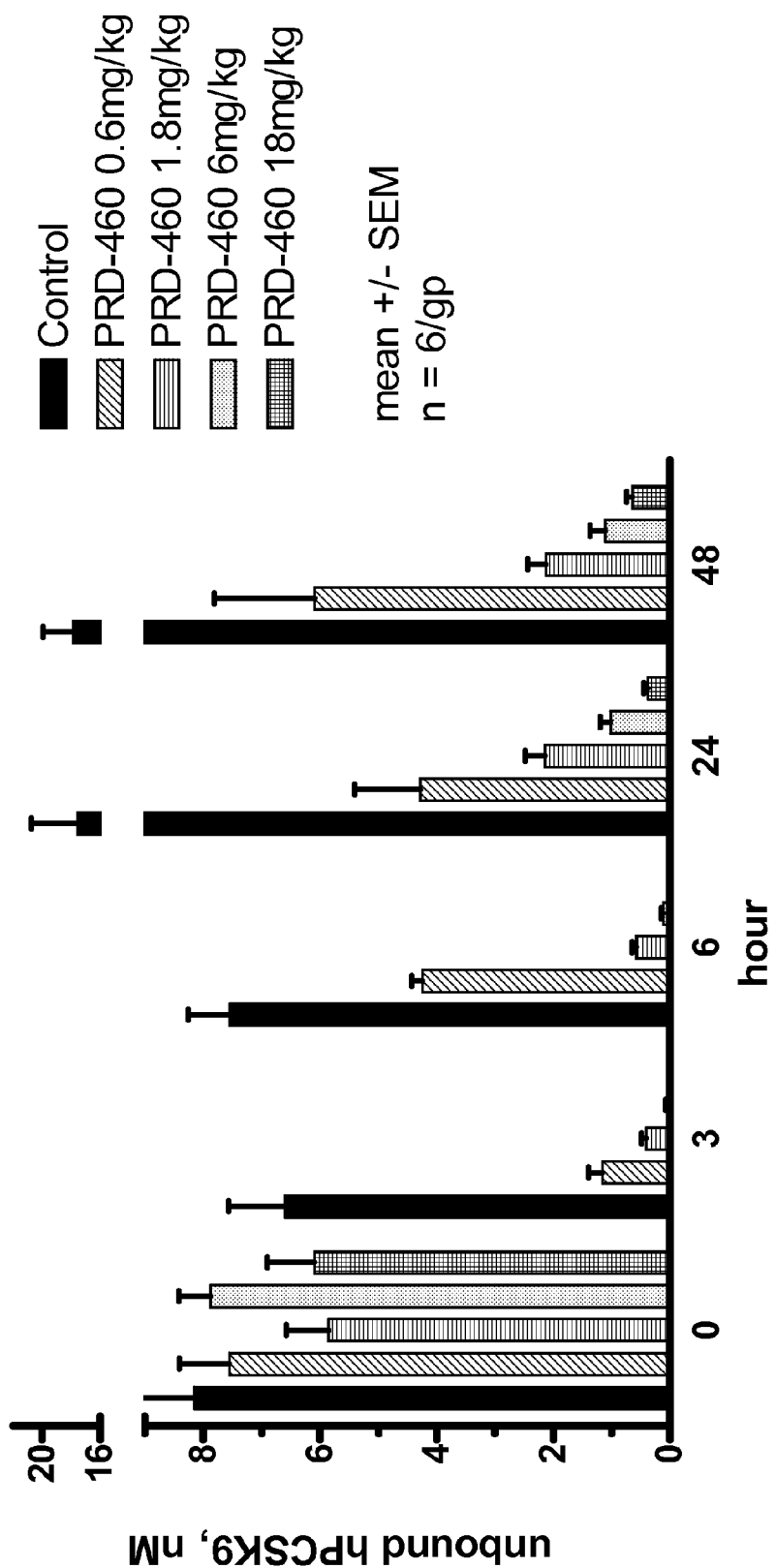
FIG. 4. Plasma unbound hPCSK9 levels in transgenic mice treated with PRD460 (dosed i.p.).

In vivo studies were conducted in the line 66 genomic hPCSK9 transgenic mouse model developed at BMS. This line expresses physiological levels of hPCSK9 (~1-5 nM). Binding of adnectins to PCSK9 in the plasma is predicted to result in a decrease in the measured amount of unbound (free) circulating PCSK9. The decrease in unbound PCSK9 is the initial pharmacodynamic event which results in inhibition of the PCSK9-LDLR interaction and in LDL cholesterol lowering. Administration of single doses of PRD460 (i.p. doses from 0.6 to 18 mg/kg) to the transgenic mice resulted in rapid, strong decreases in plasma unbound hPCSK9 levels (FIG. 4). Dose-dependent decreases in unbound PCSK9 were observed with ED50<0.6 mg/kg at the 3 hr time point. These findings in the normal expresser human PCSK9 transgenic mouse model show that PRD460 binds strongly and potently to circulating hPCSK9 in vivo.

Example 8

In Vivo Pharmacodynamics in Cynomolgus Monkeys

Figure 5:
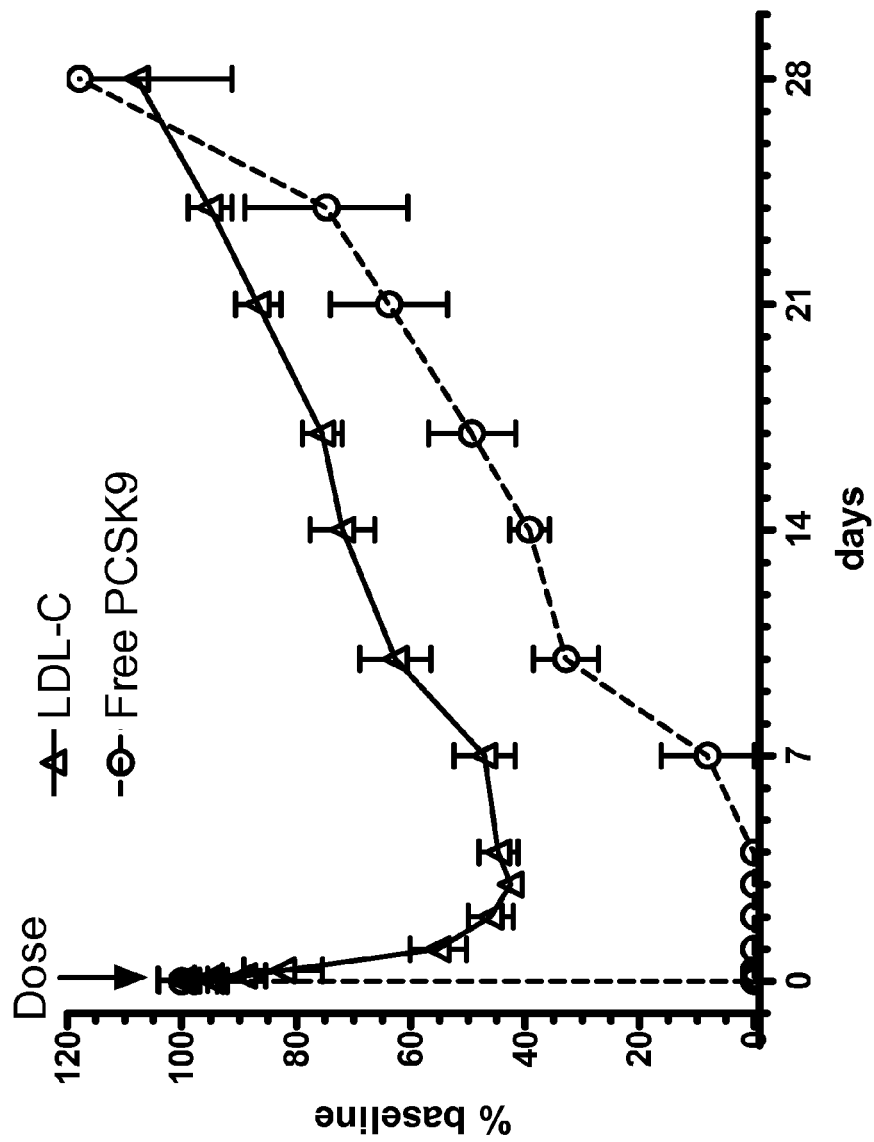
FIG. 5. Effect of PRD460 (15 mg/kg i.v.) on LDL-C and free PCSK9 in cynomolgus monkeys (mean+/−SEM, n=3).

The pharmacodynamic effects of PCSK9 adnectin PRD460 were evaluated in normal lean cynomolgus monkeys. PRD460 was administered to monkeys by i.v. dosing at 15 mg/kg, and plasma samples were collected at time intervals over 4 wks for the assay of LDL-C and free PCSK9 levels. A single dose of PRD460 rapidly lowered plasma LDL-C levels in the monkeys, reaching an average maximum effect of 42% of baseline LDL-C (58% reduction; n=3 monkeys) by day 3 after dosing (FIG. 5). LDL-C levels were reduced by 50% or more for a week at this dose, remaining significantly below baseline for 3 wks and returning to baseline by 4 wks. Total cholesterol showed a similar pattern but no effect on HDL was observed (not shown). Treatment with PRD460 caused an immediate drop to near zero (below the lower limit of quantitation) in the unbound, free form of plasma PCSK9 (FIG. 5). The free PCSK9 levels remained near the lower limits of detection for several days then gradually returned to baseline levels by the end of 4 wks, consistent with a cause/effect relationship with plasma LDL-C. The data indicate that plasma LDL lowering mirrored the drop in free PCSK9 levels, consistent with PCSK9 inhibition regulating LDLR function following treatment with PRD460 in vivo. Pharmacokinetic analysis revealed that the plasma half-life of adnectin PRD460 was approximately 70 hrs in this cynomolgus monkey study. These findings indicate that a PCSK9 adnectin-Fc fusion protein is highly efficacious and fast-acting with robust, specific, and long-lasting effects on LDL-C lowering in the cynomolgus monkey model.

Example 9

Pharmacokinetic Properties of Fc-$^{10}$Fn3 Fusion Proteins

Pharmacokinetic properties of Fc-$^{10}$Fn3 fusion proteins were evaluated in mice and cynomolgus monkeys. The results of these experiments are summarized in Table 2.

TABLE 2

Summary of Pharmacokinetics properties of various $^{10}$Fn3-Fc fusion to several different proteins in mice and cynomolgus monkeys

| ID | mouse $t_{1/2}$ (hours) | cyno $t_{1/2}$ (hours) |
| --- | --- | --- |
| PRD460 | 96 | 74-78 |
| PRD461 | 67 | nd |
| PRD239 | 61 | nd |
| PRD713 | 66 | nd |
| Adn-1 | 68 (IV) | 188 (IV) |
|  | 57 (SC) | 335 (SC)* |
| Adn-4 | 30 (IV) | ND |
|  | 25 (SC) | ND |
| Adn-5 | 65 (IV) | ND |
|  | 65 (SC) | ND |
| Adn-8 | 64 | ND |
| Adn-2 | ND | 51-67 |
| Adn-3 | 73 | 84-90 |
| Adn-9 | 28-30 | ND |
| Adn-6 | 83 | ND |
| Adn-7 | 126 | ND |
| C7FLFc | 23 | 47 |

*$t_{1/2}$ could not accurately be determined.

Monkey In Vivo Study Designs

To determine the PK of various Fc-$^{10}$Fn3 fusion proteins in monkeys, monkeys were dosed from 0.5-15 mg/kg either IV or SC with the fusion protein of interest and serum or plasma samples were collected at specific time points over the course of 4 weeks. Samples were collected and processed in $K_2$EDTA or SST for plasma or serum, respectively, and stored at −80° C. until analysis.

ELISA/ECLA Method

In most instances, ELISA or ECLA assays were developed to determine the plasma concentration of Fc-$^{10}$Fn3 fusions in mouse or monkey plasma. In general, either biotinylated target, target-Fc fusion, or anti-idiotypic antibodies were used to capture the Fc-$^{10}$Fn3 fusions in plasma or serum. Detection was achieved via either an anti-hu-Fc antibody coupled to HRP or sulfo-tag, or antibodies that is binds the constant regions of the $^{10}$Fn3 domain in combination with anti-rabbit-HRP or sulfo-tagged polyclonal antibodies. In one instance, both capture and detection were achieved via anti-hu-Fc polyclonals in which the detection antibody was coupled to HRP. The read-out was either colorimetric via TMB or electrochemiluminescent using the Mesoscale Discovery platform. Plasma concentrations were typically calculated based on a 4 or 5-parameter fit of an 8-point standard curve.

LC/MS/MS Method

In some instances, LC/MS/MS methods were developed to determine the plasma concentration of Fc-$^{10}$Fn3 fusions in mouse or monkey plasma or serum. The analysis utilizes trypsin digestion of the target proteins to generate a surrogate peptide from the Adnectin portion of the molecules and a surrogate peptide from the Fc region. The surrogate peptides were detected by tandem mass spectrometry. The basis of quantification is the stoichiometric relationship between Adnectin proteins and the surrogates.

Standard curves were prepared in the same matrix as the study samples. The standard curves and study samples were subjected to thermal denaturation followed by tryptic digestion prior to protein precipitation, followed by LC-MS/MS analysis. Plasma concentrations were typically calculated based on quadratic fit of a standard curve.

Pharmacokinetic Analysis

Pharmacokinetic (PK) parameters for Fc-$^{10}$Fn3 fusions were calculated using Phoenix WinNonlin version 6.2 (Pharsight Corp, Mountain View, Calif.) non-compartmental analysis or comparable software. The peak concentration (Cmax) was recorded directly from experimental observations. The area under the curve (AUC) values were calculated using a combination of linear and log trapezoidal summations. The total plasma clearance (CL_F_obs), volume of distribution (Vz_F_obs or Vss), terminal half-life (T-HALF) and mean residence time (MRT) were estimated. Pharmacokinetic Properties of Fc-$^{10}$Fn3 Fusion Proteins in Cynomolgus Monkeys.

Figure 6:
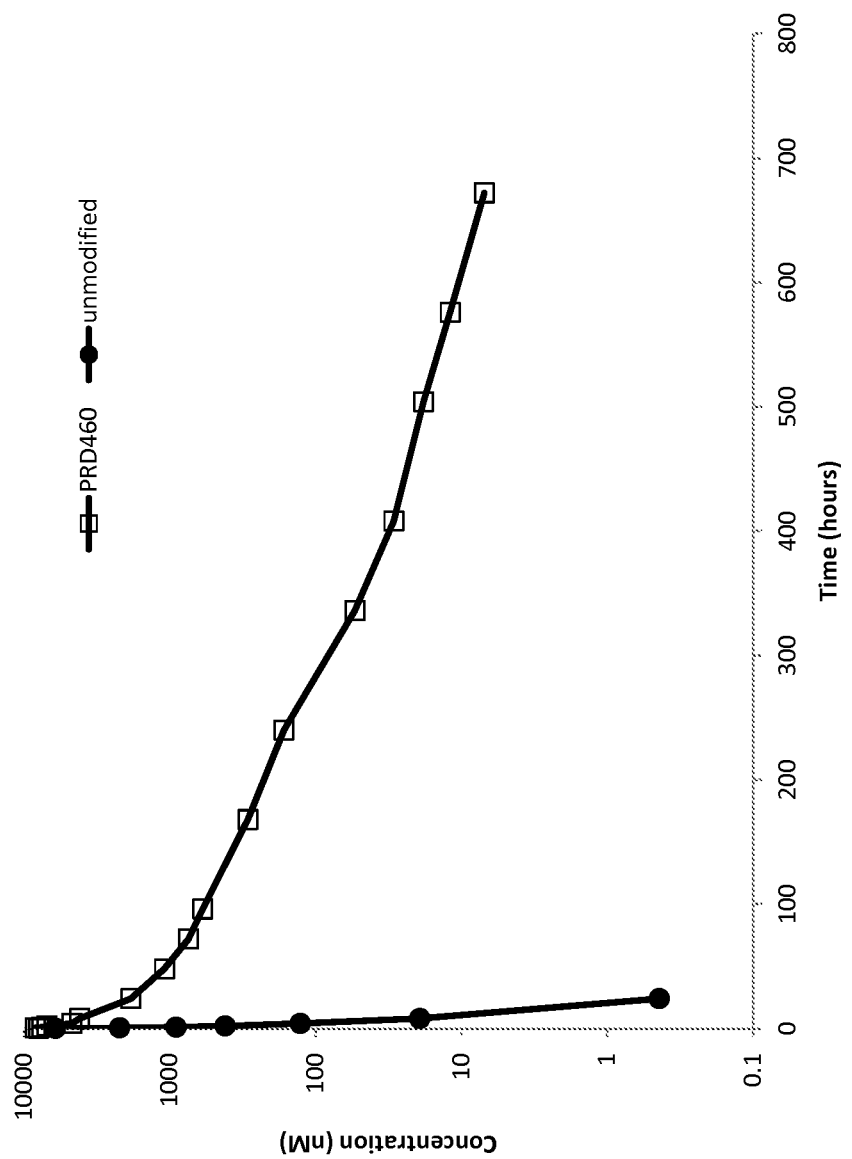
FIG. 6. Pharmacokinetics of PRD460 and ATI-1081 following intravenous administration into cynomolgus monkeys.

The half-life ($t_{1/2}$) of PCSK9 Adnectin PRD460 (Fc-$^{10}$Fn3) and that of PCSK9 Adnectin ATI-1081 (no Fc) was determined following administration into cynomolgus monkeys. Results show that Fc moiety enhances the half-life of $^{10}$Fn3 proteins (FIG. 6 and Tables 2 and 3).

TABLE 3

Pharmacokinetic properties of PRD460 vs. ATI-1081

| Format | T-HALF (h) | $V_D$ (mL/kg) | CL (mL/h/kg) | AUCall (h * µmol/L) | MRT (h) |
|---|---|---|---|---|---|
| ATI-1081 | 1.27 | 385 | 214 | 4.32 | 1.31 |
| PRD460 | 78 | 104 | 0.92 | 230 | 74 |

Figure 7:
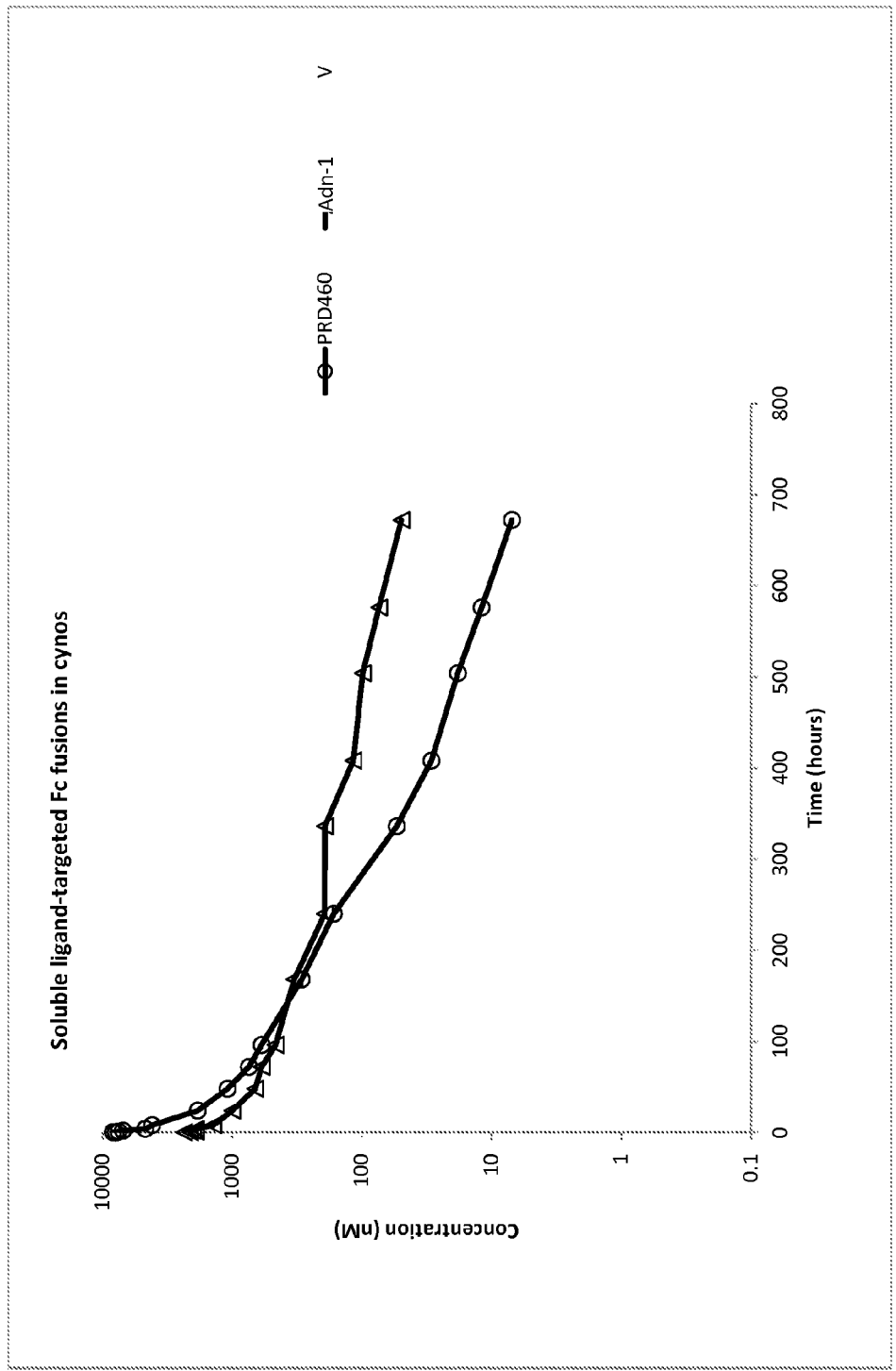
FIG. 7. Pharmacokinetics of PRD460 and Adn-1 following intravenous administration into cynomolgus monkeys.

An experiment was performed to compare the half-life ($t_{1/2}$) of Fc-$^{10}$Fn3 fusion proteins targeting soluble ligands. The pharmacokinetics of PCSK9 PRD460 and another Fc-$^{10}$Fn3 fusion protein to a different soluble ligand target (Adn-1) were evaluated following IV administration into cynomolgus monkeys. Adn-1 exhibited a significantly longer $t_{1/2}$ than PRD460 indicating that the target or $^{10}$Fn3 component can influence the PK properties of Fc-$^{10}$Fn3 fusion proteins. The results are summarized in FIG. 7 and Tables 2 and 4.

TABLE 4

Pharmacokinetic properties of Adn-1 and PRD460

| ID | T-HALF (h) | $V_D$ (mL/kg) | CL (mL/h/kg) | AUCall (h * µM) | MRT (h) |
|---|---|---|---|---|---|
| Adn-1 | 188 | 81 | 0.35 | 194 | 234 |
| PRD460 | 78 | 104 | 0.92 | 230 | 74 |

Figure 8:
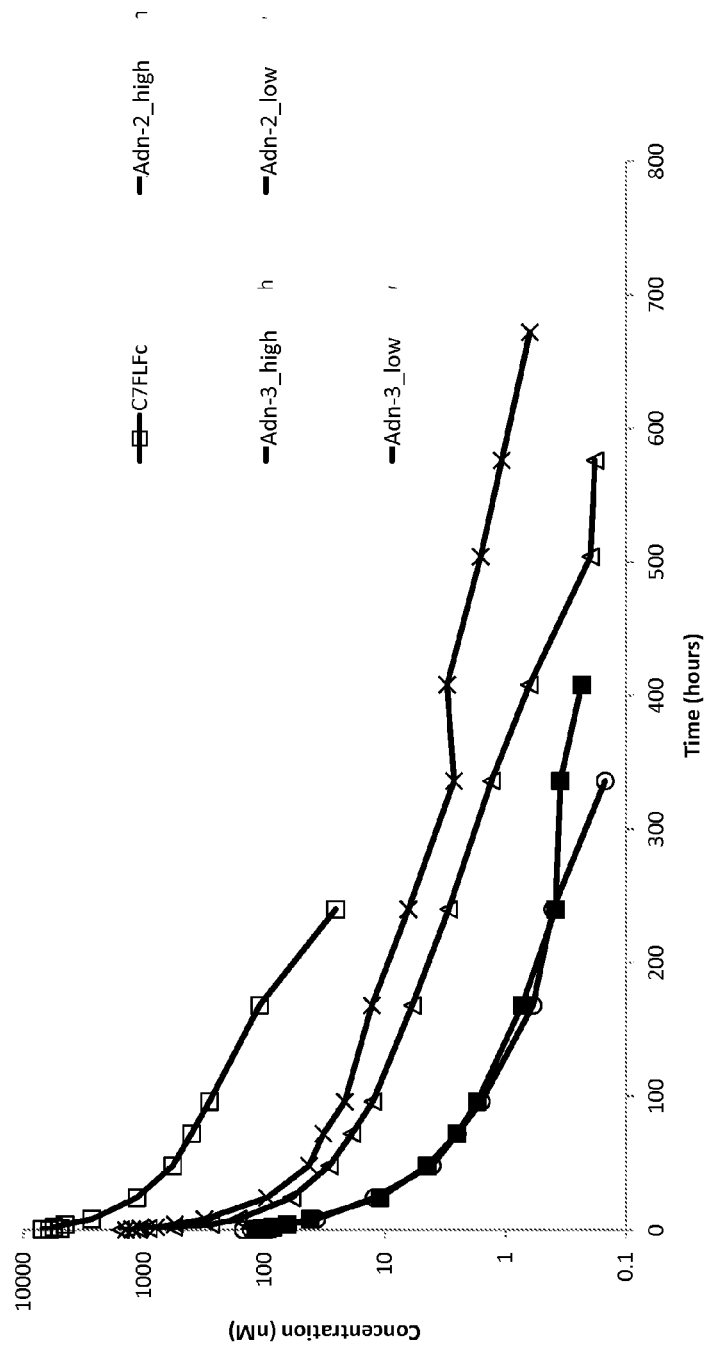
FIG. 8. Pharmacokinetics of C7FLFc, Adn-2 and Adn-3 following intravenous administration into cynomolgus monkeys.

Another experiment was performed to compare the half-life ($t_{1/2}$) of Fc-$^{10}$Fn3 fusion proteins targeting cell-surface receptors. The pharmacokinetics of an anti-VEGFR2 $^{10}$Fn3-Fc fusion protein (C7FLFc) and two other Fc-$^{10}$Fn3 fusion proteins to a different cell-surface receptor target (Adn-2 and Adn-3) were evaluated following IV administration into cynomolgus monkeys. The $V_D$ and CL of Adn-2 & Adn-3 were similar to each other but greater than observed for C7FLFc, suggesting an influence of the target on the PK properties of Fc-$^{10}$Fn3 fusion proteins. The results are summarized in FIG. 8 and Tables 2 and 5.

TABLE 5

Pharmacokinetic properties of C7FLFc, Adn-2 and Adn-3

| ID | Dose (mg/kg) | T-HALF (h) | $V_D$ (mL/kg) | CL (mL/h/kg) | AUC (h * µM) | MRT (h) |
|---|---|---|---|---|---|---|
| C7FLFc | 10 | 47 | 73 | 1 | 127 | 43 |
| Adn-2 | 0.5 | 51 | 120 | 4.5 | 1.3 | 29 |
|  | 5 | 67 | 300 | 6.4 | 8.4 | 46 |
| Adn-3 | 0.5 | 84 | 150 | 4.2 | 1.4 | 40 |
|  | 5 | 90 | 210 | 4.3 | 13.9 | 54 |

Figure 9:
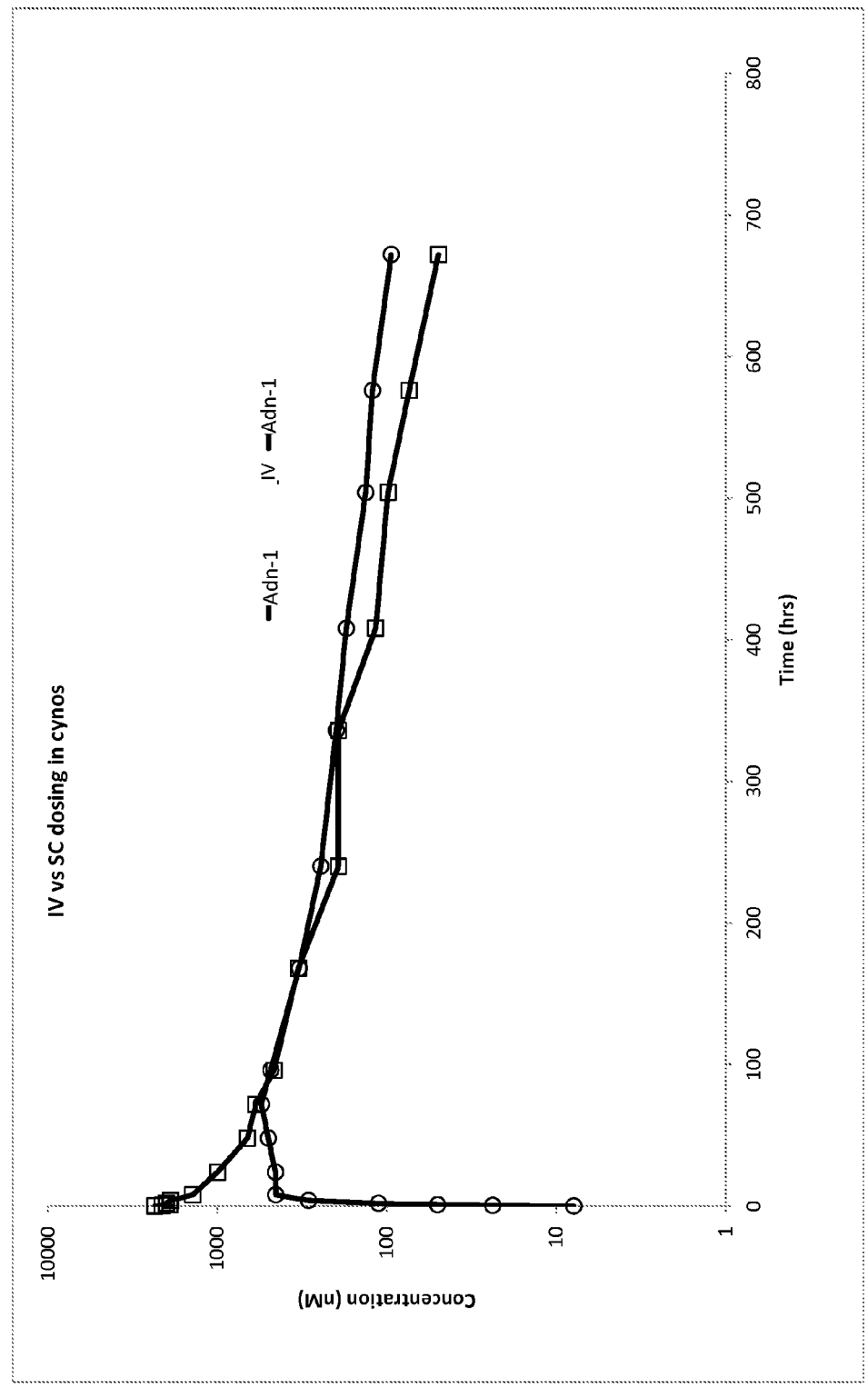
FIG. 9. Pharmacokinetics of Adn-1 in cynomolgus monkeys following intravenous and subcutaneous administration.

Another experiment was performed to determine the bioavailability of an Fc-$^{10}$Fn3 fusion protein, Adn-1, in cynomolgus monkeys. Following intravenous (IV) administration, the volume of distribution ($V_D$) of Adn-1 was 81 mL/kg. Total body plasma clearance of Adn-1 was low (0.31 mL/h/kg) and the half-life ($t_{1/2}$) was 188 h (FIG. 9 and Table 6). Adn-1 demonstrated subcutaneous (SC) bioavailability of 92% (FIG. 9 and Table 6).

TABLE 6

Single-dose Pharmacokinetic Parameters (mean ± SD) of Adn-1 in Monkeys.

| Dose Route | T-HALF (h) | $V_D$ (mL/kg) | CL (mL/h/kg) | AUCall (h * µM) | MRT (h) | SC Bioavailability (%) |
|---|---|---|---|---|---|---|
| IV | 188 | 81 | 0.35 | 194 | 234 | n/a |
| SC | 335* | — | — | 164 | 451 | 92 |

*$t_{1/2}$ cannot accurately be determined.

Pharmacokinetic Properties of Fc-$^{10}$Fn3 Fusion Proteins in Mice.
Materials and Methods
Mouse In Vivo Study Designs To determine the pharmacokinetic properties of various Fc-$^{10}$Fn3 fusion proteins in mice, mice were dosed either IV or SC with the fusion protein of interest and serum or plasma samples were collected at specific time points over the course of 2-3 weeks. Samples were collected via tail vein or retro-orbital sinus in either CPD or $K_2$EDTA for plasma or in SST for serum and stored at −80° C. until analysis. The details of various study designs are listed in Table 7 below.

TABLE 7

Mouse in vivo Study Designs

| ID | Mouse strain | Dose (mg/kg) | Dose route | Study Duration |
|---|---|---|---|---|
| PRD460 | NCr nu C57Bl/6 | 10 | IV | 2 weeks |
| PRD461 | NCr nu C57Bl/6 | 10 | IV | 2 weeks |
| PRD239 | NCr nu | 10 | IV | 2 weeks |
| PRD713 | NCr nu | 10 | IV | 2 weeks |
| Adn-1 | SCID | 2 | IV | 2 weeks |
|  |  |  | SC |  |
| Adn-4 | SCID | 0.74 | IV | 2 weeks |
|  |  |  | SC |  |
| Adn-5 | SCID | 2 | IV | 2 weeks |
|  |  |  | SC |  |
| Adn-8 | Balb/c | 8 | IV | 2 weeks |
| Adn-3 | Balb/c | 1 | IV | 2 weeks |
| Adn-9 | Balb/c | 1 | IV | 2 weeks |
|  |  | 8 | IV |  |
| Adn-6 | C57Bl/6 | 2 | IV | 3 weeks |
|  |  |  | SC |  |
| Adn-7 | C57Bl/6 | 2 | IV | 3 weeks |
|  |  |  | SC |  |
| C7FLFc | NCr nu | 10 | IV | 2 weeks |

Pharmacokinetic Properties of Fc-$^{10}$Fn3 Fusion Proteins in Mice.

Figure 10:
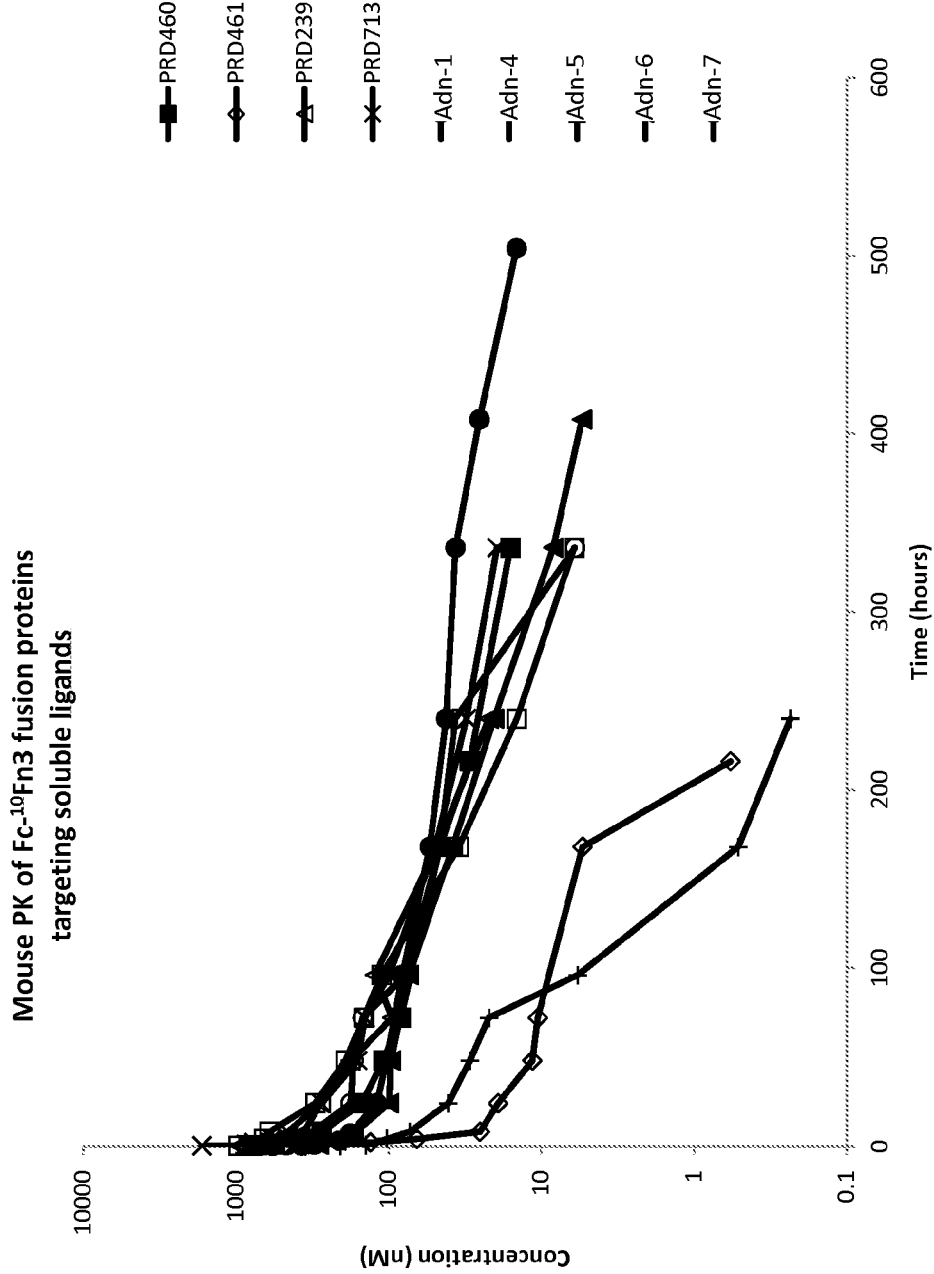
FIG. 10. Pharmacokinetics of PRD460, PRD461, PRD239, PRD713, Adn-1, Adn-4, Adn-5, Adn-6 and Adn-7 following intravenous administration into mice.

A series of experiments were performed in mice to evaluate the PK properties and half-life ($t_{1/2}$) of various Fc-$^{10}$FN3 fusion proteins. Results are summarized in FIGS. 10-14, and Tables 2, 8-10. The PK profiles of Fc-$^{10}$FN3 fusion proteins targeting soluble ligands are shown in FIG. 10 and half-lives ($t_{1/2}$s) are summarized in Table 2. The results indicate similar PK profiles for the majority of Fc-$^{10}$FN3 fusion proteins examined. The half-lives ranged from 25-126 hours in mice. Two Fc-$^{10}$FN3 fusion proteins exhibited a different profile from the majority of the group and these results suggest an influence of the $^{10}$FN3 component on PK.

Figure 11:
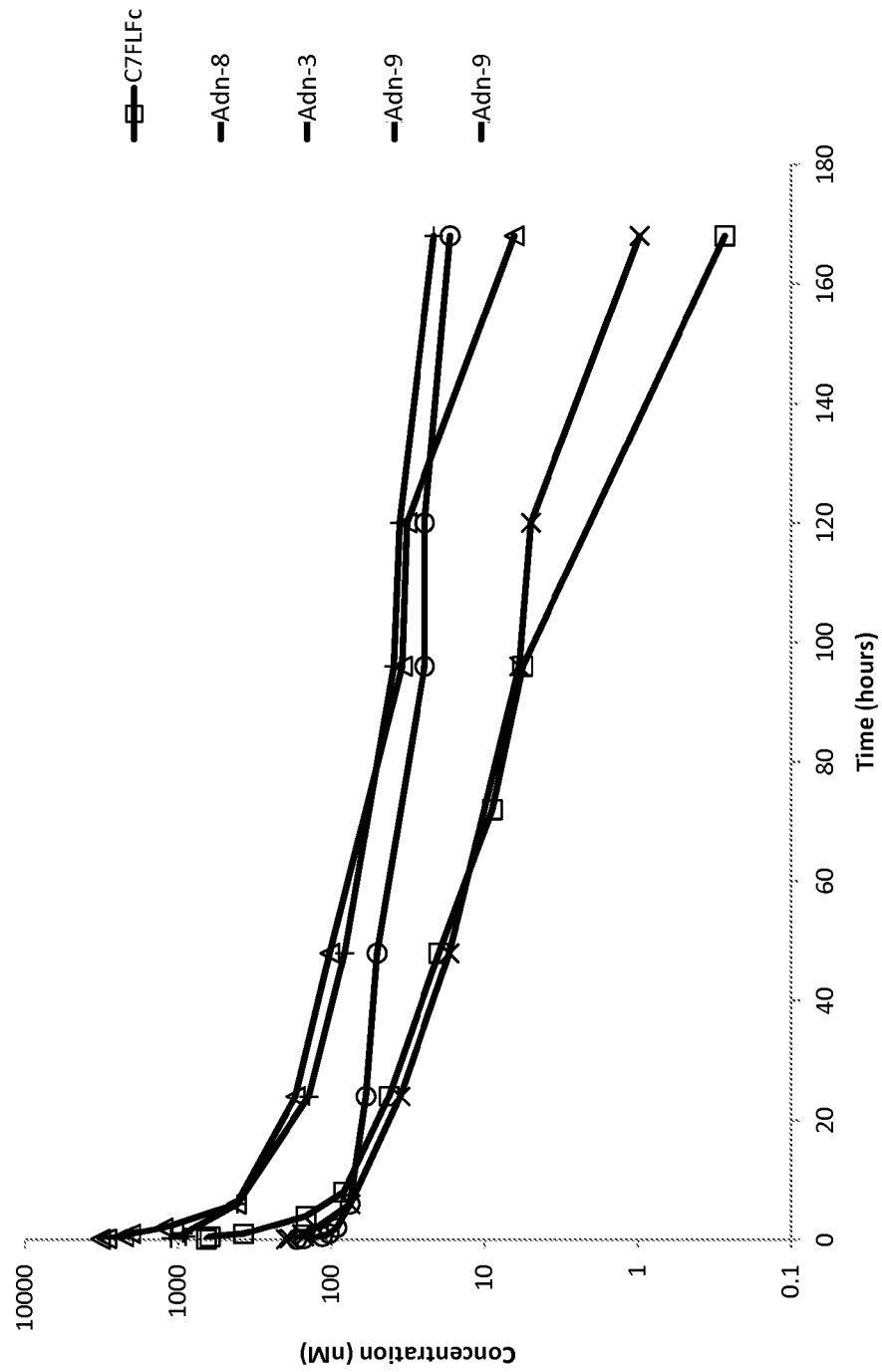
FIG. 11. Pharmacokinetics of C7FLFc, Adn-8, Adn-3 and Adn-9 following intravenous administration into mice.

The PK profiles of Fc-$^{10}$FN3 fusion proteins targeting cell-surface receptors are shown in FIG. 11 and half-lives ($t_{1/2}$s) are summarized in Table 2. The results indicate similar PK profiles for the majority of Fc-$^{10}$FN3 fusion proteins examined. The half-lives ranged from 23-73 hours in mice. Two Fc-$^{10}$FN3 fusion proteins exhibited a different profile from the majority of the group and these results suggest an influence of the $^{10}$FN3 component and/or target on PK.

Figure 12:
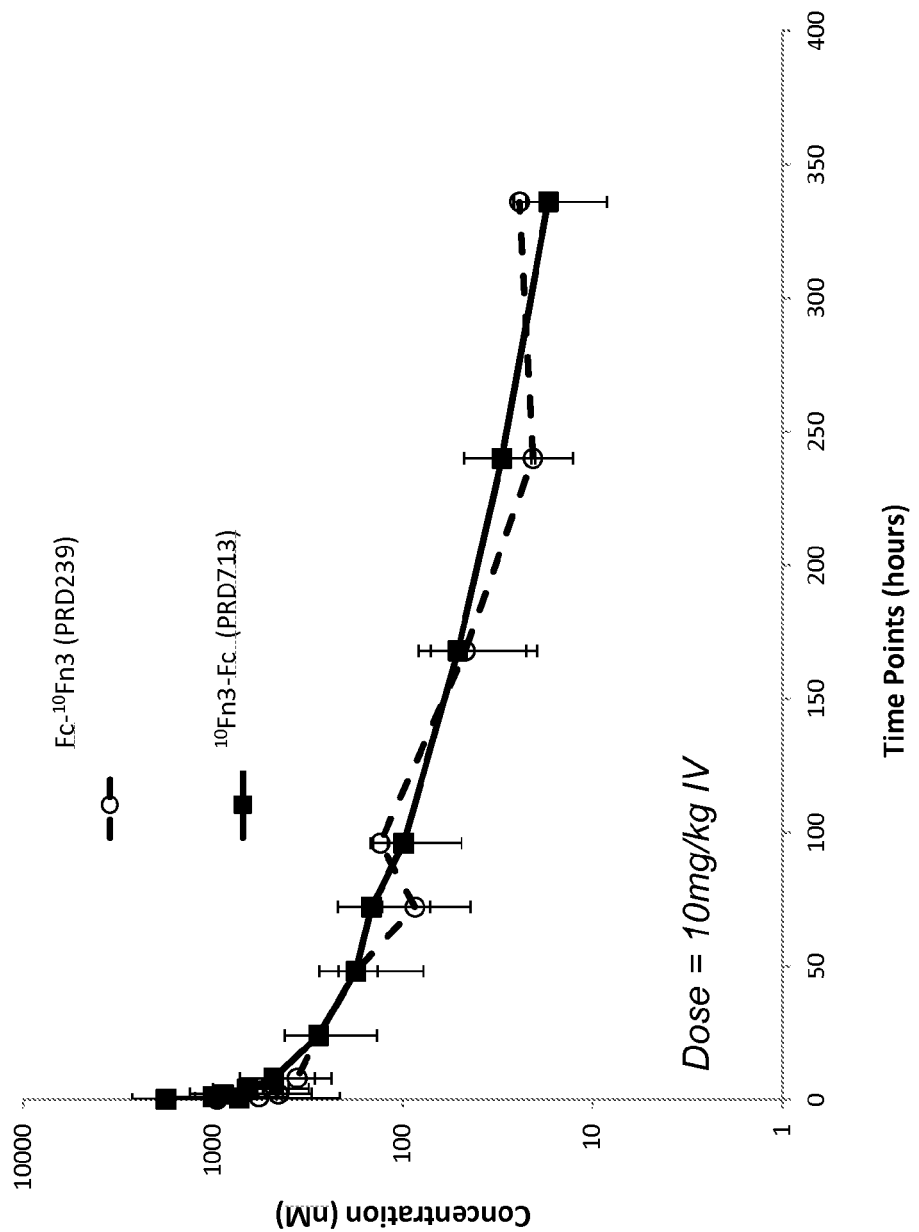
FIG. 12. Pharmacokinetics of PRD239 and PRD713 following intravenous administration into mice.

An experiment was performed to determine whether the X-Fc or Fc-X orientation influences Fc-$^{10}$FN3 fusion protein pharmacokinetics (PK). The PK properties of PRD239 and PRD713, two Fc-$^{10}$FN3 fusion proteins created with the same $^{10}$FN3 component were evaluated following IV administration in nude mice. As shown in FIG. 12 and Tables 2 and 8, the orientation does not affect the PK properties in mice.

Example 10

Binding Affinity of Fc-$^{10}$Fn3 Fusions Vs. Non-Fc $^{10}$Fn3 Proteins

The binding properties of Fc-$^{10}$Fn3 fusion proteins and non-Fc $^{10}$Fn3 proteins were characterized by Surface Plasmon Resonance (SPR). Anti-human or anti-Histidine antibody was immobilized on a Biacore chip, and $^{10}$Fn3 proteins and Fc-$^{10}$Fn3 fusions were captured on the chip surface. Varying concentrations of target were placed into the flow solution using MgCl2 (3 M) for chip regeneration between cycles. Kinetic determinations were performed at 25° C. Evaluation of the kinetic parameters was performed using

TABLE 8

Pharmacokinetic properties of two IL-23 Adnectins, PRD239 and PRD713

| ID | Orientation | T-HALF (h) | $V_D$ (mL/kg) | CL (mL/h/kg) | AUCall (h * μM) | MRT (h) |
|---|---|---|---|---|---|---|
| PRD239 | Fc-X | 60.7 ± 2.9 | 382.5 ± 53.4 | 4.36 ± 0.41 | 29.1 ± 2.9 | 81.8 ± 3.7 |
| PRD713 | X-Fc | 65.6 ± 11.8 | 359.1 ± 5 | 3.89 ± 0.8 | 34.2 ± 6.4 | 81.4 ± 17.1 |

Figure 13:
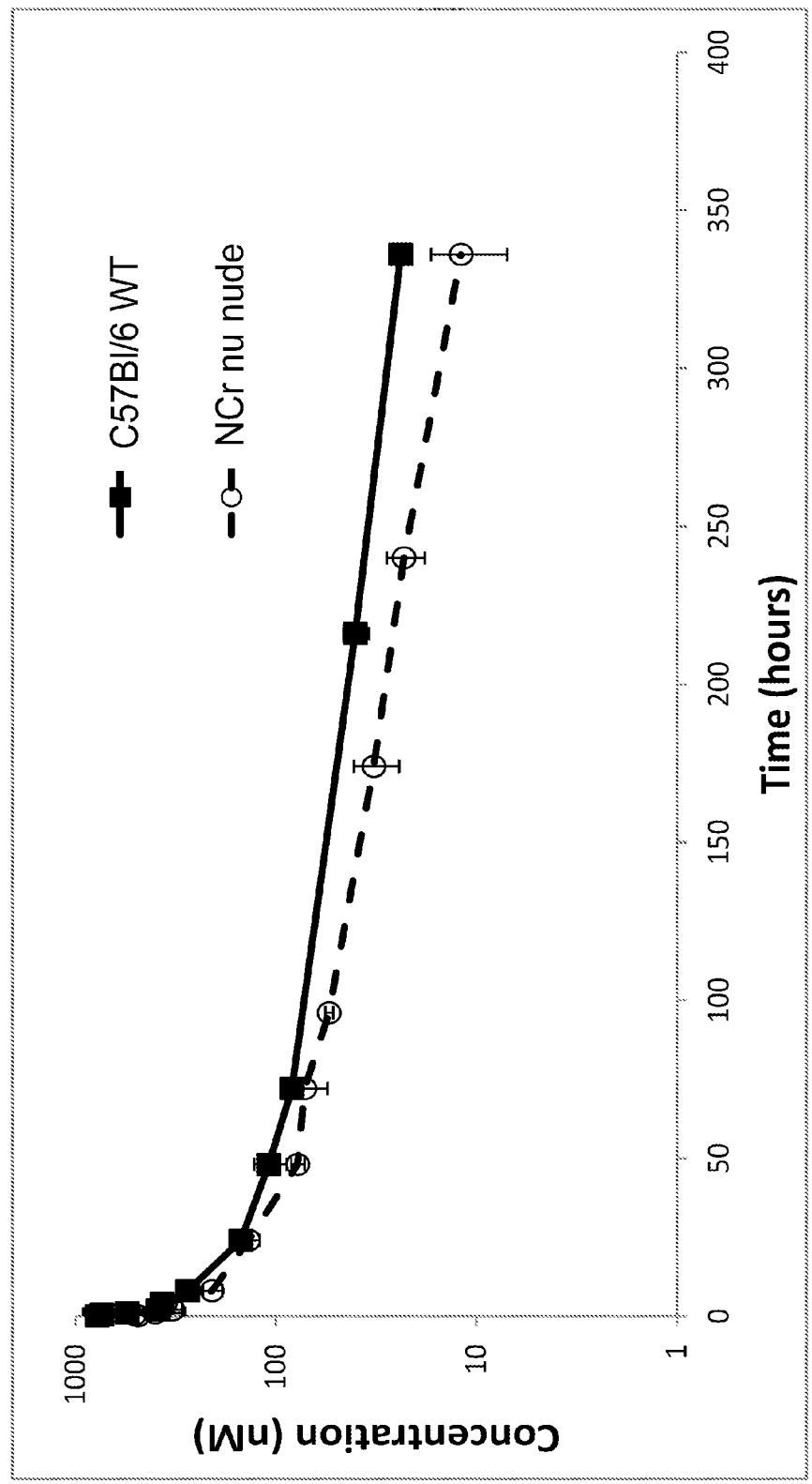
FIG. 13. Pharmacokinetics of PRD460 following intravenous administration into C57B1/6 and nude mice.

An experiment was performed to determine whether the strain of mice influences Fc-$^{10}$FN3 fusion protein pharmacokinetics (PK). The PK properties of PRD460 were evaluated following IV administration in nude or C57B1/6 mice. As shown in FIG. 13 and Tables 2 and 9, the mouse strain does not affect the PK properties of Fc-$^{10}$FN3 fusion proteins.

the 1:1 binding algorithm on the Biacore Evaluation software.

The results are shown in Table 11 below. In some instances, the orientation of the $^{10}$Fn3 to the Fc did not affect binding whereas in others it did. Overall, these results show that the presence of Fc does not negatively affect binding affinity.

TABLE 9

Pharmacokinetic properties of PRD460 in C57Bl/6 and nude mice

| ID | Mouse Strain | T-HALF (h) | $V_D$ (mL/kg) | CL (mL/h/kg) | AUCall (h * μM) | MRT (h) |
|---|---|---|---|---|---|---|
| PRD460 | C57Bl/6 | 120.1 ± 3.5 | 951.3 ± 254.9 | 5.48 ± 1.41 | 23.09 ± 3.48 | 143.1 ± 7.6 |
| PRD460 | nude | 95.6 ± 12.4 | 941.4 ± 95.4 | 6.84 ± 0.25 | 18.22 ± 0.63 | 121.9 ± 17.5 |

Figure 14:
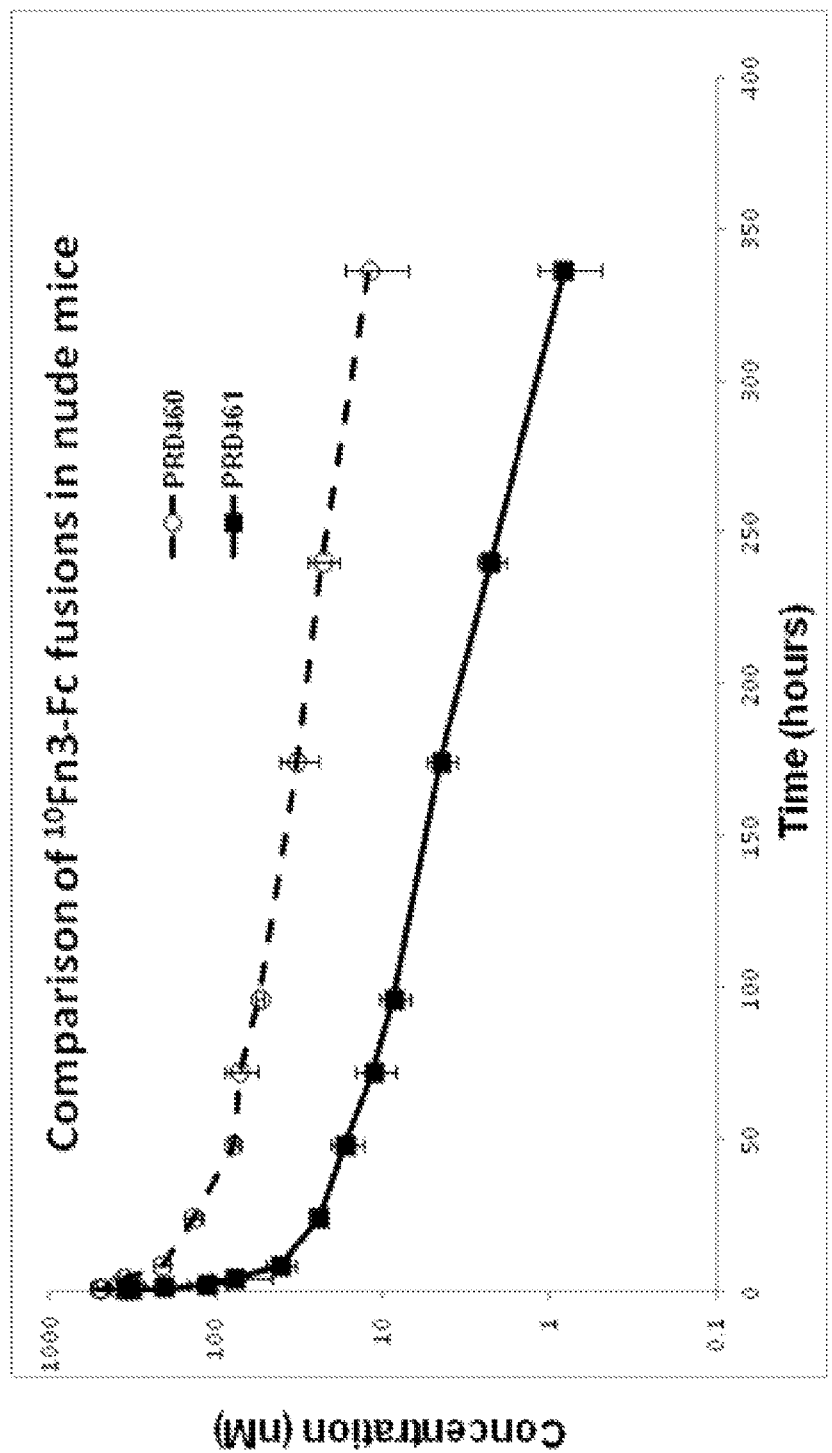
FIG. 14. Pharmacokinetics of PRD460 and PRD461 following intravenous administration into mice.

An experiment was performed to determine whether the $^{10}$Fn3 component affects Fc-$^{10}$FN3 fusion protein pharmacokinetics (PK). The PK properties of two Fc-$^{10}$FN3 fusion proteins that target PCSK9, PRD460 and PRD461, were evaluated following IV administration in nude mice. As shown in FIG. 14 and Tables 2 and 10, the PCSK9 $^{10}$Fn3 component can affect the PK properties of Fc-$^{10}$FN3 fusion proteins.

TABLE 11

Kinetic parameters for $^{10}$Fn3-Fc fusion proteins and unmodified $^{10}$Fn3 proteins against captured targets.

| ID | Target | Orientation | ka (1/Ms) | kd (1/s) | KD (nM) |
|---|---|---|---|---|---|
| 1784F03 | PCSK9 | No Fc | 1.15E+04 | 3.96E−04 | 34.46 |
| PRD289 | PCSK9 | X-Fc | 1.20E+04 | 1.03E−04 | 8.60 |
| PRD292 | PCSK9 | Fc-X | 4.68E+03 | 1.49E−04 | 31.82 |

TABLE 10

Pharmacokinetic properties of PRD460 and PRD461 (both PCSK9 binders)

| ID | Orientation | T-HALF (hr) | $V_D$ (mL/kg) | CL (mL/hr/kg) | AUCall (hr * μM) | MRT (hr) |
|---|---|---|---|---|---|---|
| PRD460 | X-Fc | 95.6 ± 12.4 | 941.4 ± 95.4 | 6.84 ± 0.25 | 18.22 ± 0.63 | 121.9 ± 17.5 |
| PRD461 | X-Fc | 67.1 ± 11.7 | 3930.4 ± 1052.3 | 40.28 ± 5.1 | 3.33 ± 0.42 | 72.76 ± 8.9 |

TABLE 11-continued

Kinetic parameters for $^{10}$Fn3-Fc fusion proteins and unmodified $^{10}$Fn3 proteins against captured targets.

| ID | Target | Orientation | ka (1/Ms) | kd (1/s) | KD (nM) |
|---|---|---|---|---|---|
| 1813E02 | PCSK9 | No Fc | 1.75E+04 | 3.88E-04 | 22.22 |
| PRD290 | PCSK9 | X-Fc | 1.95E+04 | 2.04E-04 | 10.47 |
| PRD293 | PCSK9 | Fc-X | 6.38E+03 | 1.72E-04 | 26.87 |
| 1922G04 | PCSK9 | No Fc | 3.23E+04 | 2.10E-04 | 6.502 |
| PRD 461 | PCSK9 | X-Fc | 3.23E+04 | 1.08E-04 | 3.353 |
| PRD 463 | PCSK9 | Fc-X | 2.04E+04 | 8.63E-05 | 4.237 |
| 1459D05 | PCSK9 | No Fc | 5.56E+03 | 5.30E-04 | 95.26 |
| PRD288 | PCSK9 | X-Fc | 5.63E+03 | 3.37E-04 | 59.89 |
| PRD291 | PCSK9 | Fc-X | 4.28E+03 | 8.23E-04 | 192.20 |
| ATI-1081 | PCSK9 | No Fc | 3.65E+04 | 2.45E-04 | 6.7 |
| PRD460 | PCSK9 | X-Fc | 3.75E+04 | 1.21E-04 | 3.29 |
| PRD462 | PCSK9 | Fc-X | 7.33E+03 | 3.27E-04 | 44.58 |
| C7FL | VEGFR2 | No Fc | 2.05E+4 | 2.36e-4 | 11.5 |
| C7FL-Fc | VEGFR2 | X-Fc | 1.07E+04 | 1.69E-04 | 15.80 |

Example 11

Ba/F3 Proliferation Assay

Figure 15:
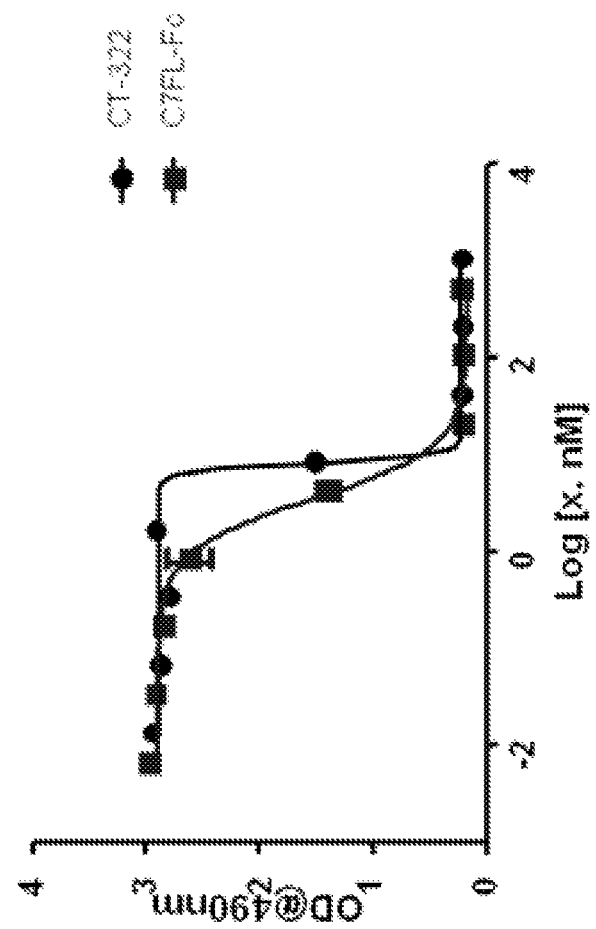
FIG. 15. Inhibition of BaF3 proliferation by C7FL-Fc.

The ability of C7FL-Fc (anti-VEGFR2Fc-$^{10}$Fn3) to inhibit proliferation of Ba/F3 cells was compared to inhibition by CT322 (anti-VEGFR2 $^{10}$Fn3). Ba/F3 cells stably expressing a VEGFR2 fusion protein (comprising the extracellular domain of hVEGFR2 and the intracellular domain of hEpoR) were plated in 96-well plates at 25,000 cells/well in 90 µl growth media containing 15 ng/ml of VEGF-A, VEGF-C, or VEGF-D. Serial dilution of CT322 or C7FL-Fc were prepared at 10× final concentration, and 10 µl of CT322 or C7FL-Fc was added to each well. Plates were incubated at 37° C./5% CO2 for 48-72 hours. 20 µl of CellTiter 96® Aqueous One Solution Reagent (Promega) was added to each well, and the plates were further incubated for 3-4 hours at 37° C. At the end of the incubation period, absorbance was read at 490 nm using a microtiter plate reader. FIG. 15 shows that C7FL-Fc can inhibit Ba/F3 proliferation equivalently to CT322. The results are summarized in Table 12.

TABLE 12

Summary of Ba/F3 proliferation assay

| ID | IC50 (nM) | Relative Potency |
|---|---|---|
| CT-322 | 7.961 | 1 |
| C7FL-Fc | 3.374 | 2.36 |

Example 12

Evaluation of Linkers for the Generation of Fc-$^{10}$Fn3 Fusion Proteins

Experiments were performed to evaluate the performance of 8 different linkers for the generation of Fc-$^{10}$Fn3 fusion proteins. The fusion proteins were evaluated on four criteria: (i) protein concentration, (ii) monomer content, (iii) melting temperature, and (iv) binding affinity for target. Table 13 lists the different linkers chosen for this study.

Four different $^{10}$Fn3 molecules, each specific for a different target, were fused to each linker, in the Fc-X orientation. The four different $^{10}$Fn3 molecules are Adn-1, C7FL, Adn-10 and 2013. In total, 32 different Fc fusion molecules were generated and analyzed.

TABLE 13

Linkers

| Number | Linker | Length | Description | SEQ ID NO. |
|---|---|---|---|---|
| 1 | QPDEP | 5 | Derived from human CH2-CH3 link; R→D | 81 |
| 2 | AGGGGSG | 7 | Standard linker in Fc-X Adnectin fusions. | 37 |
| 3 | PVPPPPP | 7 | IgA2 hinge, rigid | 82 |
| 4 | (ED)$_5$E | 11 | Synthetic, solubilizing, flexible | 83 |
| 5 | DLPQETLEEETPGA | 14 | Derived from membrane IgA tail sequence | 84 |
| 6 | VPSTPPTPSPST | 12 | IgA1 hinge short | 85 |
| 7 | ELQLEESAAEAQEGELE | 17 | Derived from membrane IgG1 tail sequence (D→E) | 86 |
| 8 | ESPKAQASSVPTAQPQAE | 18 | IgD hinge 1st exon long | 87 |

High-Throughput Mammalian Expressed Protein (HMEP) Analysis

Expression constructs encoding the 32 Fc-$^{10}$Fn3 fusion proteins were transfected into 4 ml of HEK-293-6E culture using 24 deep-well plates and incubated and incubated at 37° C. Five days post-transfection, the cells were lysed and protein was purified using Protein A HP Multitrap. The resulting protein preparation was evaluated for protein yield using a BCA Protein assay with SGE (control Adnectin™) as the protein standard.

Figure 18:
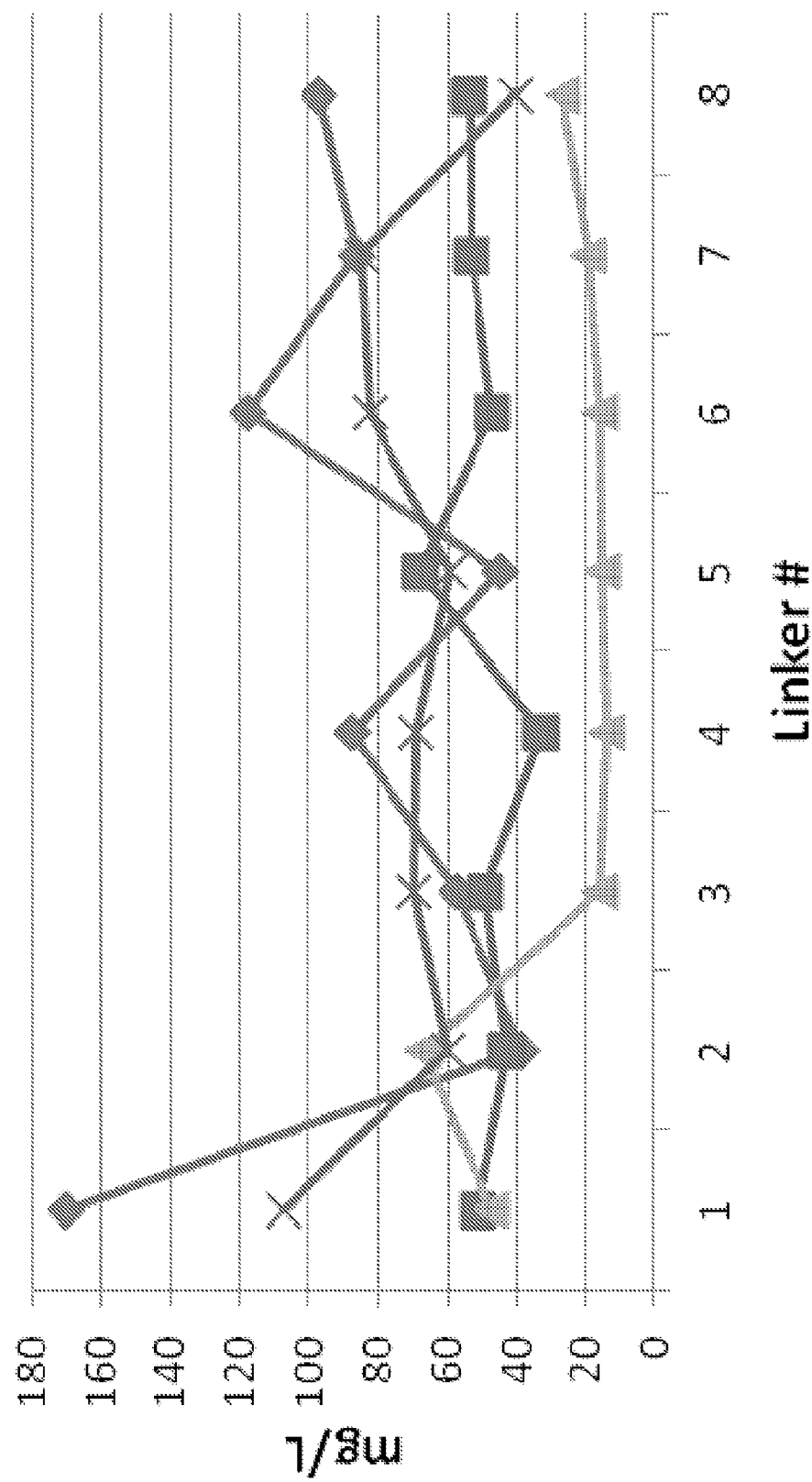
FIG. 18. Average yield of high-throughput mammalian expressed Fc-$^{10}$Fn3 proteins.

FIG. 18 is a graph summarizing the average yield per transfection volume of each Fc-$^{10}$Fn3 fusion series. Diamonds represent the And-1 series, squares represent the Fc-C7FL series, triangles represent the Adn-10 series, and crosses represent the Fc-2013 series. Overall, the Adn-1 series had the highest average yield per transfection volume.

Size exclusion chromatography (SEC) was performed on the Fc-$^{10}$Fn3 fusion proteins resulting from the HMEP. SEC was performed using a Superdex 200 5/150 or Superdex 75 5/150 column (GE Healthcare) on an Agilent 1100 or 1200 HPLC system with UV detection at $A_{214}$ nm and $A_{280}$ nm and with fluorescence detection (excitation=280 nm, emission=350 nm). A buffer of 100 mM sodium sulfate, 100 mM sodium phosphate, 150 mM sodium chloride, pH 6.8 at appropriate flow rate of the SEC column employed. Gel filtration standards (Bio-Rad Laboratories, Hercules, Calif.) were used for molecular weight calibration.

Figure 19:
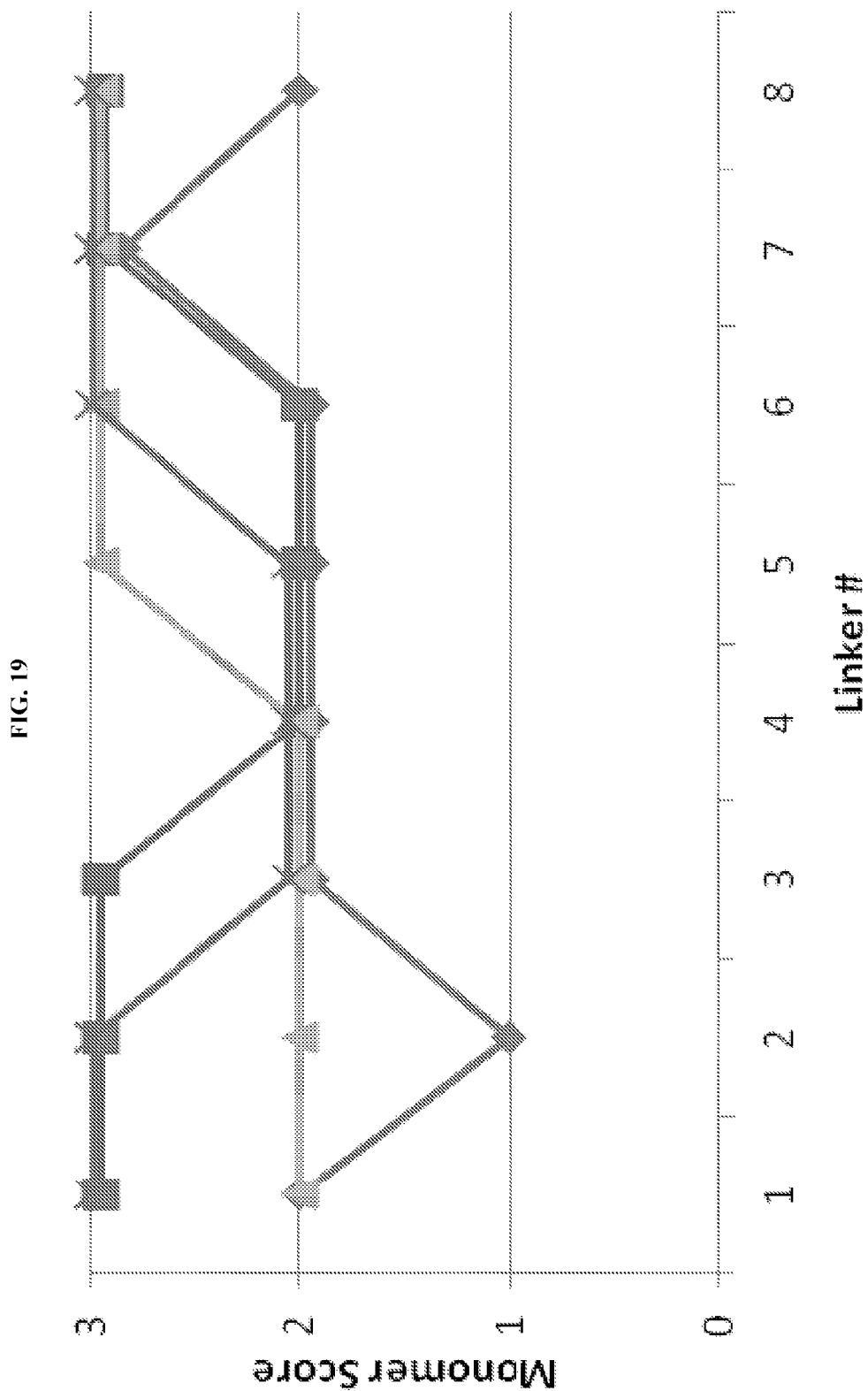
FIG. 19. Monomer score of high-throughput mammalian expressed Fc-$^{10}$Fn3 proteins.

FIG. 19 is a graph summarizing the monomer score of each Fc-$^{10}$Fn3 fusion series. Labels are the same as in FIG. 18. Results show that Fc-$^{10}$Fn3 fusions with linker 7 have high percent monomer score.

Midscale Expressed Protein Analysis

The Adn-1 linker series was chosen for midscale analysis. Expression constructs encoding the Adn-1 linker series were transfected into 175 ml of HEK-293-6E. Five days post-transfection, the cells were lysed and protein was purified using Protein A purification on an AKTA 100. The resulting protein preparation was evaluated for protein yield using a BCA Protein assay with SGE (control Adnectin™) as the protein standard.

Figure 20:
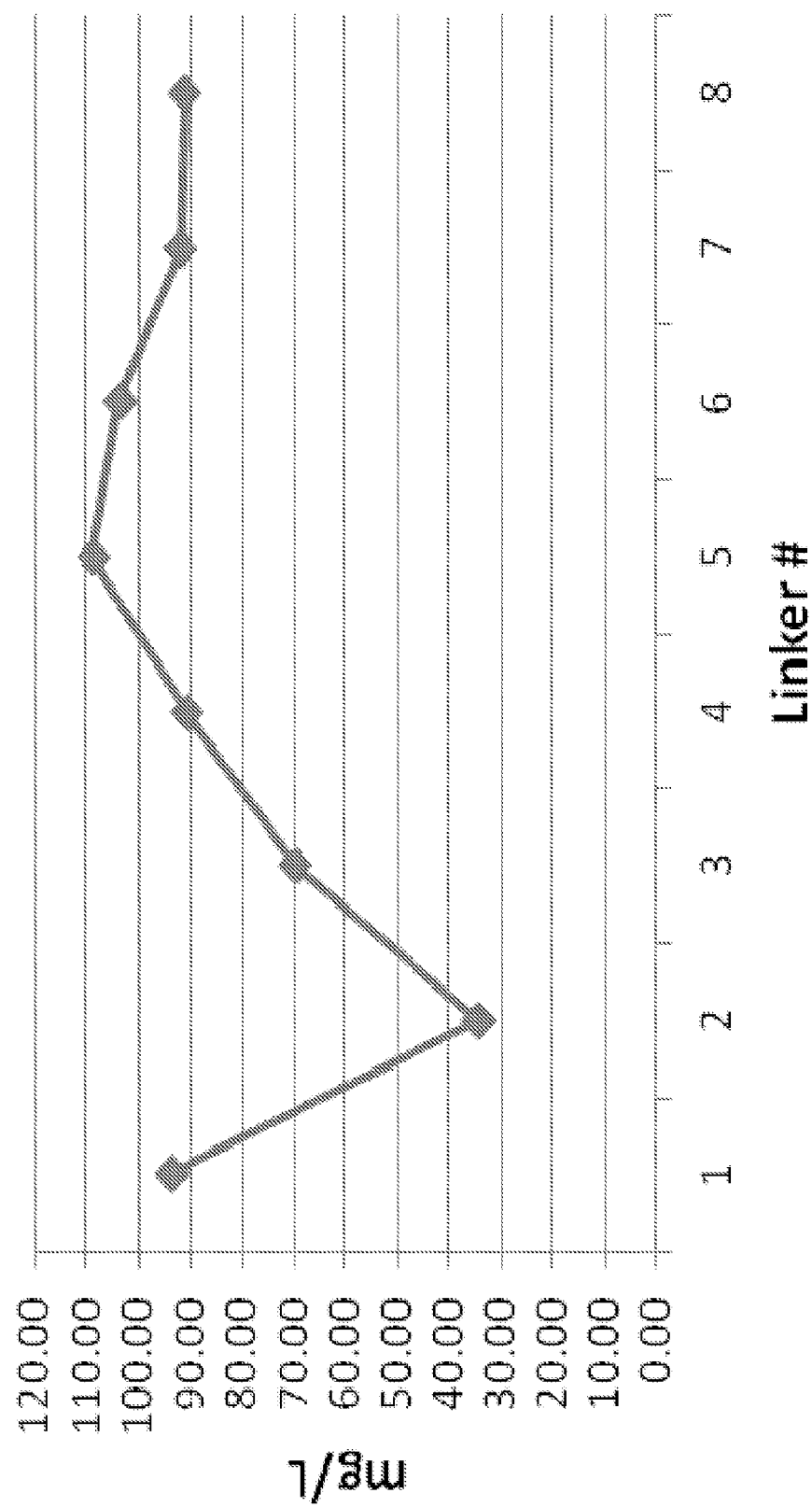
FIG. 20. Average yield of mid-scale expressed Fc-$^{10}$Fn3 proteins.

FIG. 20 is a graph summarizing the average yield for the Adn-1 linker series. Results show that yield is high for most Adn-1 fusions.

Figure 21:
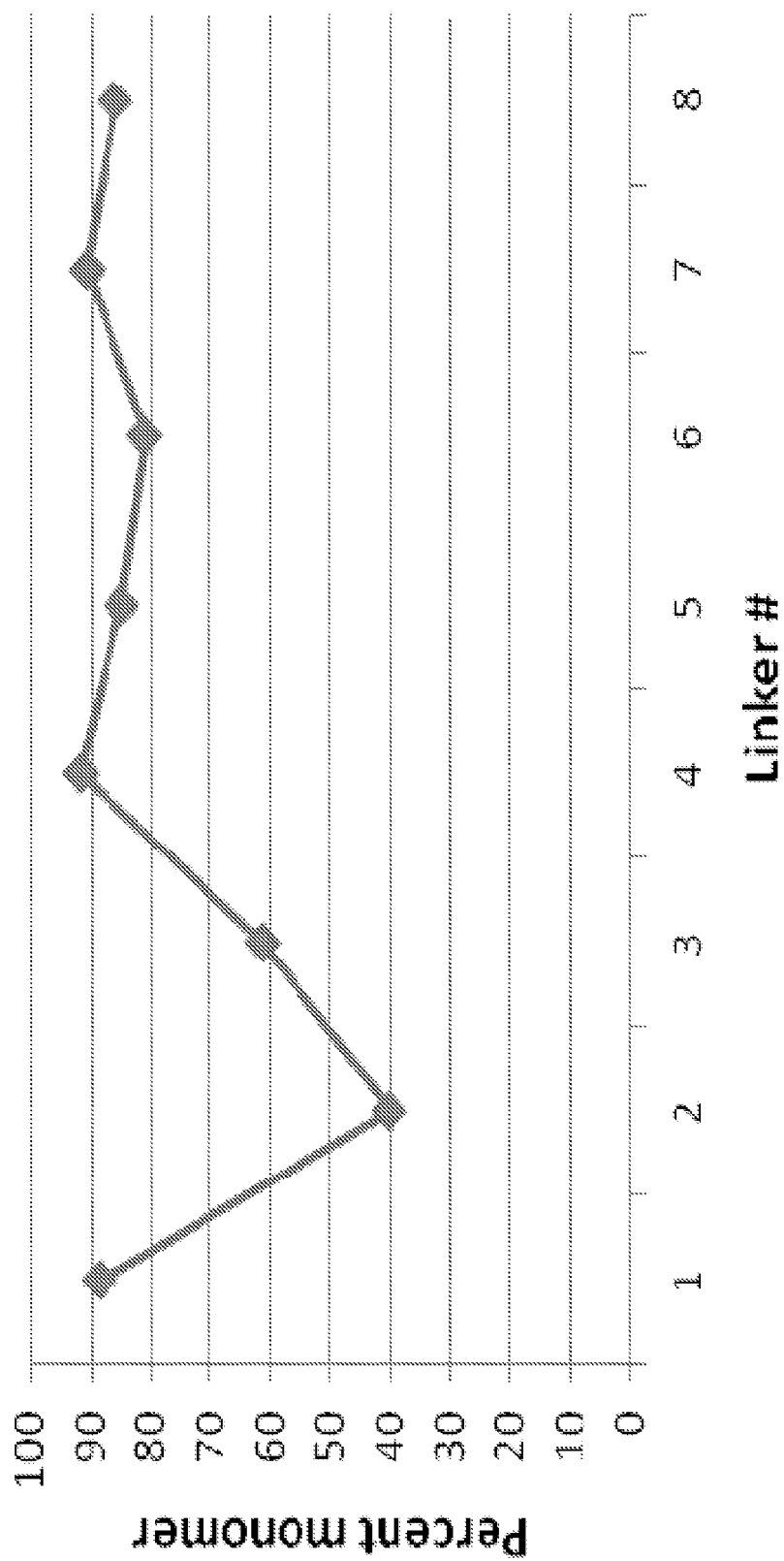
FIG. 21. Monomer score of mid-scale expressed Fc-$^{10}$Fn3 proteins.

SEC analysis of the midscale purified Adn-1 fusions demonstrated that most Adn-1 fusions have high monomer content. FIG. 21 is a graph summarizing the monomer score for each of the Adn-1 fusions.

Figure 22:
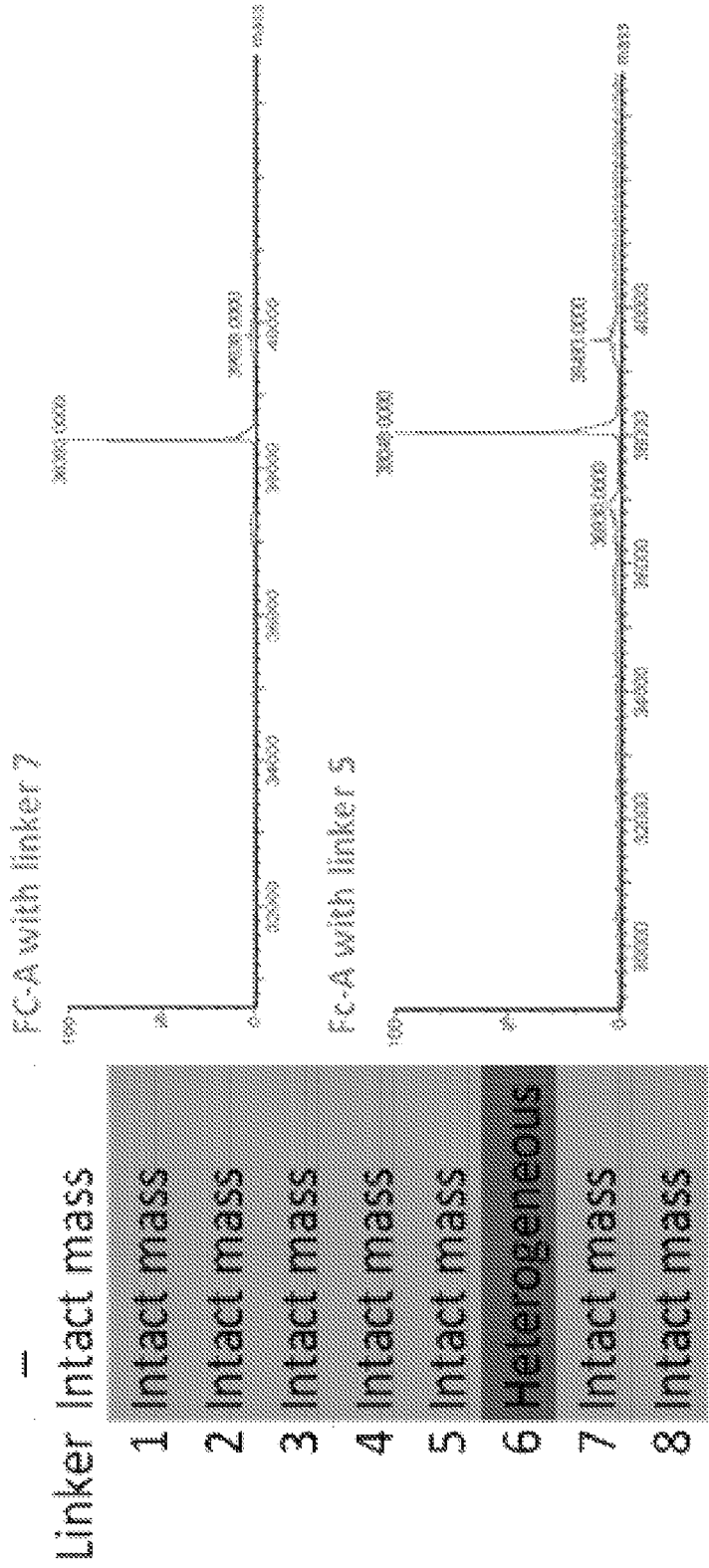
FIG. 22. LC-MS data of mid-scale expressed Fc-$^{10}$Fn3 proteins.

Liquid chromatography-mass spectrometry (LC-MS) was performed on the midscale purified Fc-$^{10}$Fn3 fusion proteins. FIG. 22 summarizes the LC-MS results, which confirms the identities of seven of the tested Adn-1 fusions. Representative LC-MS plots for fusions with linkers 5 and 7 are shown.

Figure 23:
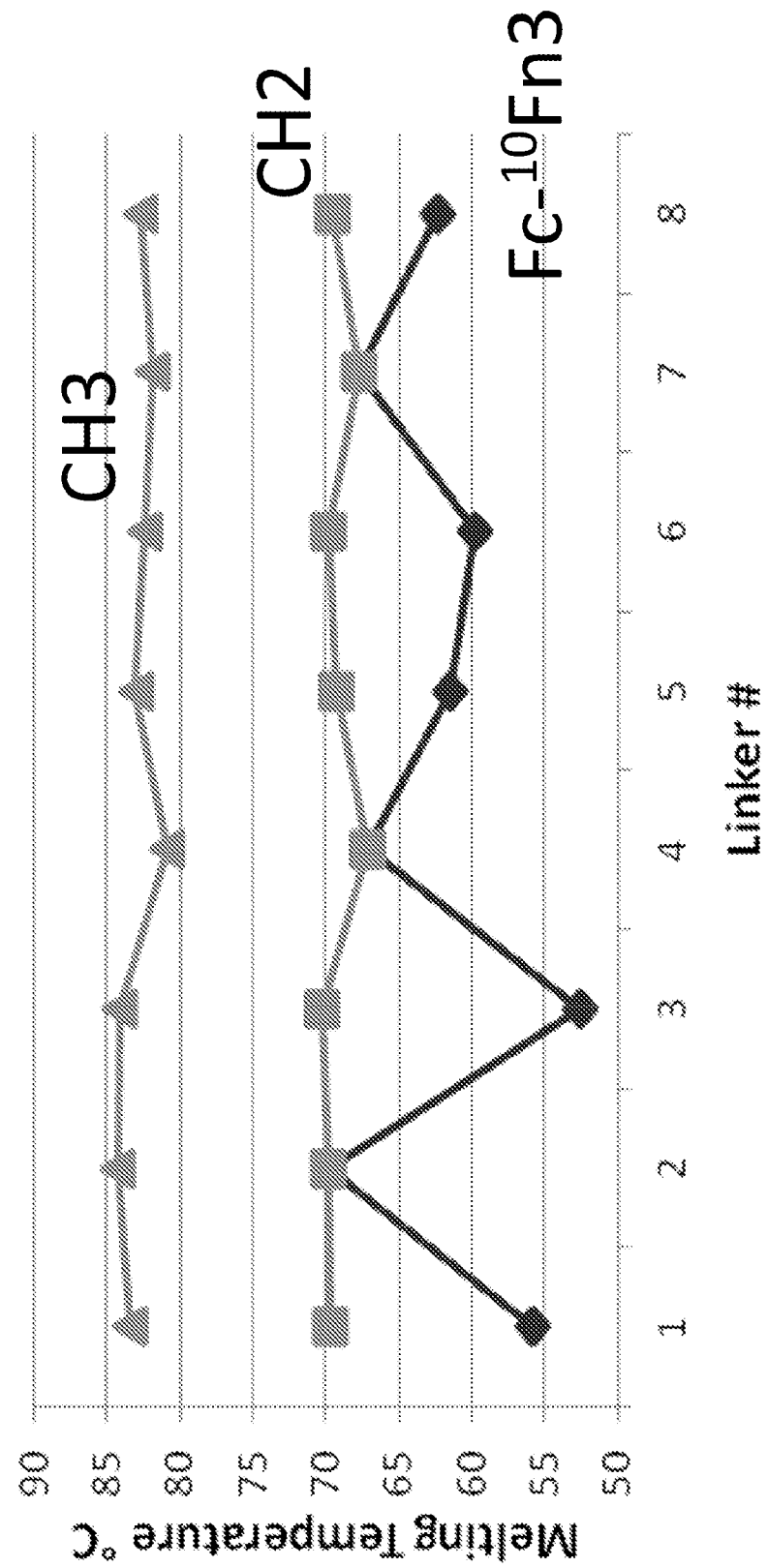
FIG. 23. DSC data of mid-scale expressed Fc-$^{10}$Fn3 proteins.

The melting temperatures of the midscale purified Fc-$^{10}$Fn3 fusion proteins were measured by differential scanning calorimetry (DSC). A 1 mg/ml solution of each of the Fc-$^{10}$Fn3 fusion protein preparation was scanned in a N-DSC II calorimeter (calorimetry Sciences Corp) by ramping the temperature from 5° C. to 95° C. at a rate of 1 degree per minute under 3 atm pressure. The data was analyzed vs. a control run of the appropriate buffer using a best fit using Orgin Software (OrginLab Corp). FIG. 23 shows the melting temperatures for each of the Adn-1 fusions compared to control, which in this experiment are the CH2 and CH3 domains of Fc. Overall, the Adn-1 fusions have melting temperatures comparable to that of unmodified Adn-1 (no-Fc), which was previously determined to be 57° C.

Figure 24:
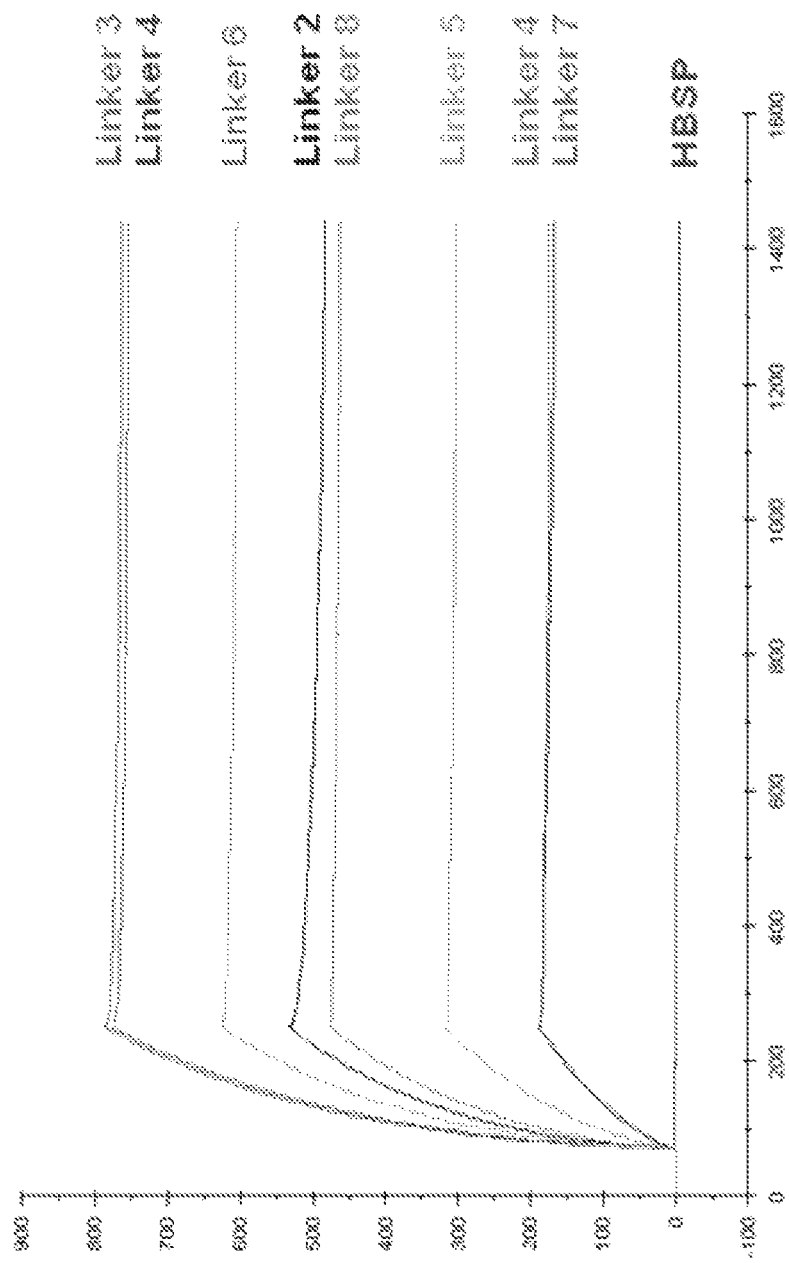
FIG. 24. SPR sensogram data for the binding of mid-scale expressed Fc-$^{10}$Fn3 proteins to target.

The binding characteristics of each of the midscale purified Fc-$^{10}$Fn3 fusion proteins to target were characterized by Surface Plasmon Resonance (SPR). FIG. 24 summarizes the binding properties of the Adn-1 series to immobilized target. Results show that all Adn-1 fusions retain binding affinity to target.

Example 13

Immunogenicity Characterization of Linkers Used for the Generation of Fc-$^{10}$Fn3 Fusion Proteins The adaptive immune response is initiated by the processing and digestion of an internalized protein by an antigen-presenting cell (APC), such as a dendritic cell. The APC clips the internalized protein into short peptides and then displays the peptides on its surface MHC Class II molecules. The peptide binding site of the MHC Class II molecule is long and narrow, like a hot-dog bun, and holds its peptide in an extended format, with room for nine amino acids in the primary binding site (and generally allows for short tails on either side of the peptide). Certain pockets in the MHC binding site are dominant in determining peptide binding. These pockets correspond to amino acid positions 1, 4, 6, and 9 in the anchored portion of the 9-mer peptide. A peptide that has favorable side chains at each of these four positions will in general bind to HLA (an MHC Class II molecule) well.

Position 1 is thought to be the most important 'anchor residue' involved in binding between the peptide and the HLA molecule. Position 1 generally favors a hydrophobic side chain—thus, 9-mers that often bind HLA are initiated with V, I, L, M, F, Y, or W. The other positions are much more variable, with different HLA alleles favoring different sets of amino acids at each site.

HLA binding may be predicted in silico, for example, using EpiMatrix. EpiMatrix is a proprietary computer algorithm developed by EpiVax, which is used to screen protein sequences for the presence of putative HLA binding motifs. Input sequences are parsed into overlapping 9-mer frames where each frame overlaps the last by 8 amino acids. Each of the resulting frames is then scored for predicted binding affinity with respect to a panel of eight common Class II HLA alleles (DRB1*0101, DRB1*0301, DRB1*0401, DRB1*0701, DRB1*0801, DRB1*1101, DRB1*1301, and DRB1*1501). Raw scores are normalized against the scores of a large sample of randomly generated peptides. The resulting "Z" score is reported. Any 9-mer peptide with an EpiMatrix Z-score in excess of 1.64 is considered a putative HLA binding motif.

The immunogenicity of linkers used to generate Fc-$^{10}$Fn3 fusion proteins was predicted using the above described in silico method. Table 14 lists the amino acid sequences of the linkers analyzed (highlighted in gray) plus flanking regions, in this case the C-terminus of IgG1 Fc and the N-terminus of the $^{10}$Fn3 domain.

Table 15 shows the EpiMatrix score for each of the linkers analyzed. All scores are very low (negative numbers in the "EpiMatrix CLUSTER SCORE" column"), indicating that the linkers are predicted to have very low immunogenicity.

TABLE 14

Linker sequences analyzed for immunogenicity

| Linker | SEQ ID NO | Sequence | SEQ ID NO. (highlighted portion) |
|---|---|---|---|
| Fc_linker_1 | 133 | QKSLSLSPQPDEPGVSDVPRD | 81 |
| Fc_linker_2 | 134 | QKSLSLSPAGGGGSGGVSDVPRD | 37 |
| Fc_linker_3 | 135 | QKSLSLSPPVPPPPPGVSDVPRD | 82 |
| Fc_linker_4 | 136 | QKSLSLSPEDEDEDEDEGVSDVPRD | 83 |
| Fc_linker_5 | 137 | QKSLSLSPDLPQETLEEETPGAGVSDVPRD | 84 |

TABLE 14-continued

Linker sequences analyzed for immunogenicity

| Linker | SEQ ID NO | Sequence | SEQ ID NO. (highlighted portion) |
|---|---|---|---|
| Fc_linker_6 | 138 | QKSLSLSPVPSTPPTPSPSTGVSDVPRD | 85 |
| Fc_linker_7 | 139 | QKSLSLSPELQLEESAAEAQEGELEGVSDVPRD | 86 |
| Fc_linker_8 | 140 | QKSLSLSPESPKAQASSVPTAQPQAEGVSDVPRD | 87 |
| Fc_linker_9 | 141 | QKSLSLSPPAVPPPGVSDVPRD | 88 |
| Fc_linker_10 | 142 | QKSLSLSPELQLEESGVSDVPRD | 132 |
| Fc_linker_11 | 143 | QKSLSLSPELQLEESAAEAQEGELEGVSDVPRD | 86 |
| Fc_linker_12 | 144 | QKSLSLSPVPSTPPTPSPSTGGVSDVPRD | 90 |
| Fc_linker_13 | 145 | QKSLSLSPVPSTPPTPSPSTPPTPSPSGGVSDVPRD | 91 |
| Fc_linker_14 | 146 | QKSLSLSPGRGGEEKKKEKEKEEGGVSDVPRD | 92 |
| Fc_linker_15 | 147 | QKSLSLSPGRGGEEKKKEKEKEEQEERETKTPGGVSDVPRD | 93 |
| Fc_linker_16 | 148 | QKSLSLSPESPKAQASSGGVSDVPRD | 94 |
| Fc_linker_17 | 149 | QKSLSLSPESPKAQASSVPTAQAPAEGGVSDVPRD | 95 |
| Fc_linker_18 | 150 | QKSLSLSPSVEEKKKEKEKEEQEERETKTPGGVSDVPRD | 96 |
| Fc_linker_19 | 151 | QKSLSLSPPSVEEKKKEKEKEEQEERETKTPGGVSDVPRD | 97 |
| Fc_linker_20 | 152 | QKSLSLSPGSVEEKKKEKEKEEQEERETKTPGGVSDVPRD | 98 |

TABLE 15

Linker EpiMatrix results

| Input Sequence | Cluster Address (w/ FLANKS) | Cluster Sequence (SEQ ID NO) |
|---|---|---|
| FC_LINKER_1 | 1-21 | QKSLSLSPQPDEPGVSGVPRD (133) |
| FC_LINKER_10 | 1-23 | QKSLSLSPELQLEESGVSDVPRD (142) |
| FC_LINKER_11 | 1-33 | QKSLSLSPELQLEESAAEAQEGELEGVSDVPRD (143) |
| FC_LINKER_12 | 1-29 | QKSLSLSPVPSTPPTPSPSTGGVSDVPRD (144) |
| FC_LINKER_13 | 1-36 | QKSLSLSPVPSTPPTPSPSTPPTPSPSGGVSDVPRD (145) |
| FC_LINKER_14 | 1-32 | QKSLSLSPGRGGEEKKKEKEKEEGGVSDVPRD (146) |
| FC_LINKER_15 | 1-41 | QKSLSLSPGRGGEEKKKEKEKEEQEERETKTPGGVSDVPRD (147) |
| FC_LINKER_16 | 1-26 | QKSLSLSPESPKAQASSGGVSDVPRD (148) |
| FC_LINKER_17 | 1-35 | QKSLSLSPESPKAQASSVPTAQPQAEGGVSDVPRD (149) |
| FC_LINKER_18 | 1-39 | QKSLSLSPSVEEKKKEKEKEEQEERETKTPGGVSDVPRD (150) |
| FC_LINKER_19 | 1-40 | QKSLSLSPPSVEEKKKEKEKEEQEERETKTPGGVSDVPRD (151) |

TABLE 15-continued

Linker EpiMatrix results

| | | |
|---|---|---|
| FC_LINKER_2 | 1-23 | QKSLSLSPAGGGGSGGVSDVPRD (134) |
| FC_LINKER_20 | 1-40 | QKSLSLSPGSVEEKKKEKEKEEQEERETKTPGGVSDVPRD (152) |
| FC_LINKER_3 | 1-23 | QKSLSLSPPVPPPPPGVSDVPRD (135) |
| FC_LINKER_4 | 1-27 | QKSLSLSPEDEDEDEDEDEGVSDVPRD (136) |
| FC_LINKER_5 | 1-30 | QKSLSLSPDLPQETLEEETPGAGVSDVPRD (137) |
| FC_LINKER_6 | 1-28 | QKSLSLSPVPSTPPTPSPSTGVSDVPRD (138) |
| FC_LINKER_7 | 1-33 | QKSLSLSPEPQLEESAAEAQEGELEGVSDVPRD (139) |
| FC_LINKER_8 | 1-34 | QKSLSLSPESPKAQASSVPTAQPQAEGVSDVPRD (140) |
| FC_LINKER_9 | 1-22 | QKSLSLSPPAVPPPGVSDVPRD (141) |

| Input Sequence | Hydro-phobicity | EpiMatrix HITS (w/o FLANKS) | EpiMatrix CLUSTER SCORE (w/o FLANKS) | tReg Adjusted CLUSTER Score (w/o FLANKS) |
|---|---|---|---|---|
| FC_LINKER_1 | -1.11 | 1 | -9.02 | -9.02 |
| FC_LINKER_10 | -0.73 | 4 | -4.53 | -4.53 |
| FC_LINKER_11 | -0.78 | 4 | -13.79 | -13.79 |
| FC_LINKER_12 | -0.63 | 1 | -15.57 | -15.57 |
| FC_LINKER_13 | -0.75 | 1 | -21.33 | -21.33 |
| FC_LINKER_14 | -1.76 | 1 | -17.88 | -17.88 |
| FC_LINKER_15 | -1.99 | 1 | -25.30 | -25.30 |
| FC_LINKER_16 | -0.82 | 0 | -14.83 | -14.83 |
| FC_LINKER_17 | -0.80 | 0 | -22.25 | -22.25 |
| FC_LINKER_18 | -1.86 | 4 | -18.19 | -18.19 |
| FC_LINKER_19 | -1.86 | 2 | -22.40 | -22.40 |
| FC_LINKER_2 | -0.47 | 1 | -10.68 | -10.68 |
| FC_LINKER_20 | -1.83 | 3 | -20.68 | -20.68 |
| FC_LINKER_3 | -0.66 | 0 | -12.36 | -12.36 |
| FC_LINKER_4 | -1.79 | 0 | -15.66 | -15.66 |
| FC_LINKER_5 | -0.88 | 1 | -14.60 | -14.60 |
| FC_LINKER_6 | -0.64 | 1 | -14.74 | -14.74 |
| FC_LINKER_7 | -0.78 | 4 | -13.79 | -13.79 |
| FC_LINKER_8 | -0.81 | 0 | -21.42 | -21.42 |
| FC_LINKER_9 | -0.46 | 0 | -11.54 | -11.54 |

Example 14

Immunogenicity of Fc-$^{10}$Fn3 Fusion Protein in Cynomolgus Monkeys

Experiments were performed to examine whether fusion to a cynomolgus Fc could decrease the immunogenicity of $^{10}$Fn3 proteins. In these experiments, the immunogenicity response in cynomolgus monkeys induced by anti-IL23 $^{10}$Fn3-Fc (1571G04-Fc) was compared to the immunogenicity response induced by anti-IL23 $^{10}$Fn3-PEG (1571G04-PEG). These two molecules share the same $^{10}$Fn3 portion.

Three cynomolgus monkeys were injected i.v. with 3 mg/kg of 1571G04-PEG or 1571G04-Fc on Days 1, 8 and 15. Plasma samples were collected on Days 1, 8, 15 prior to each injection as well as at 168, 240, 336, 408 and 504 hours after the 3$^{rd}$ dose. Plasma was analyzed for anti-adnectin antibodies in a typical ELISA assay. In short, 1571G04-PEG or 1571G04-Fc was adsorbed to microtiter plates and anti-drug antibodies in plasma samples are captured and detected with rabbit anti-human IgG-HRP conjugated antibodies. A positive response is defined as greater than twice the background level observed at the predose 1 time point for each animal.

Figure 28:
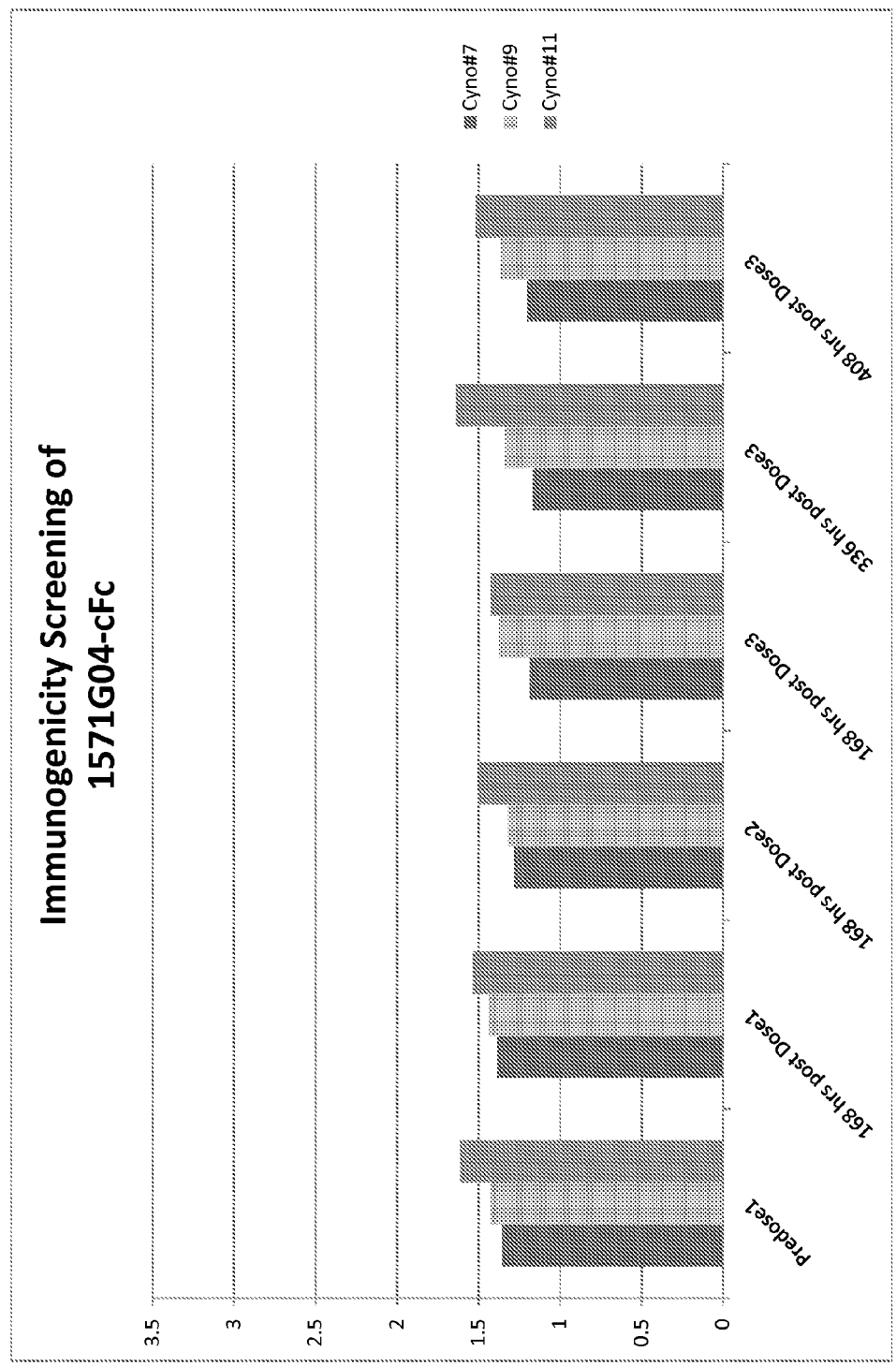
FIG. 28. Immunogenicity of 1571G04-Fc in cynomolgus monkeys.

As shown in FIG. 27, 1571G04-PEG induced a significant anti-$^{10}$Fn3 IgG response after three weekly i.v. injections of 3 mg/kg. In contrast and shown in FIG. 28, the 1571G04-Fc molecule induced very little anti-$^{10}$Fn3 IgG response, such that we did not see an increase in antibodies at any timepoint analyzed.

These results suggest that fusion of $^{10}$Fn3 proteins to a cynomolgus Fc can decrease the inherent immunogenicity of $^{10}$Fn3 proteins in cynomolgus monkeys, suggesting that a human Fc fused to $^{10}$Fn3 proteins may decrease the immunogenicity of $^{10}$Fn3 proteins in humans.

Example 15

STAT3 Phosphorylation on Kit225 Cells Method

Parham et al. (A receptor for the heterodimeric cytokine IL-23 is composed of IL-12Rbeta1 and a novel cytokine receptor subunit, IL-23R. J. Immunol. 2002 Jun. 1; 168(11): 5699-708) cloned the IL-23R from the human IL-2 dependent T-cell line, Kit225. These cells have been characterized for expression of both IL-12RB1 and 1L-23R by FACS analysis and responded to IL-23 by stimulation of pSTAT3 and to IL-12 by stimulation of pSTAT4. Kit225 cells were seeded into 96 well plates and quiesced in the absence of FBS and IL-2 for 3 hrs at 37° C. Following this incubation, 10 pM human recombinant IL-23 (or IL-23 preincubated with antagonist for 1 hr) was applied and the cells returned to the incubator for 15 minutes at 37° C. to stimulate the phosphorylation of STAT3 (abbreviated as p-STAT3). Each condition was assayed in duplicate in 96-well plates. Stimulation was stopped by placing the cells on ice and addition of ice-cold PBS. Finally, the cells were pelleted and lysed following standard protocols and pSTAT3 production detected by ELISA.

Results

Stimulation of IL23R by IL23 in Kit225 cells was assessed by measuring pSTAT3. This stimulation was effectively inhibited by the base anti-IL23 Adnectin clone 1571 G04 resulting in an $IC_{50}$ of 86.1±8.1 pM. IL23 inhibition by the 1571G04-Fc fusion protein was comparable to the unformatted Adnectin, yielding an $IC_{50}$ of 153±19 μM. The alternative orientation of Fc-1571G04 resulted in a significant loss of activity in this assay ($IC_{50}$=692±159 pM). These results are summarized in Table 16.

TABLE 16

Stat3 phosphorylation in Kit225 cells.

| Clone | pSTAT3 IC50 (pM) |
|---|---|
| 1571G04 | 86.1 ± 8.1 (n = 2) |
| PRD239 (Fc-1571G04) | 692 ± 159 (n = 2) |
| PRD713 (1571G04-Fc) | 153 ± 19 (n = 2) |

Example 16

Amino Acid Sequences of Fusion Proteins Used in the Examples

```
PRD289:
                                         (SEQ ID NO: 122)
GVSDVPRDLEVVAATPTSLLISWRPPIHAYGYYRITYGETGGNSPVQEFTVPIVEGTATIS

GLKPGVDYTITVYAVEYTFKHSGYYHRPISINYRTEIEPKSSGSTHTCPPCPAPELLGGSS

VFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLYSKLTVDKS

RWQQGNVFSCSVMHEALHNHYTQKSLSLSPG.

PRD289 has the following hinge: EPKSSGSTHTCPPCPAPELLGGSS (SEQ ID NO: 26) and a human IgG1 Fc.

PRD292:
                                         (SEQ ID NO: 123)
EPKSSGSTHTCPPCPAPELLGGSSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGAGGG

GSGGVSDVPRDLEVVAATPTSLLISWRPPIHAYGYYRITYGETGGNSPVQEFTVPIVEGT

ATISGLKPGVDYTITVYAVEYTFKHSGYYHRPISINYRTEI

PRD292 has the following hinge: EPKSSGSTHTCPPCPAPELLGGSS and the following linker: AGGGGSG, and a human IgG1 Fc.
```

PRD290:

(SEQ ID NO: 124)
GVSDVPRDLEVVAATPTSLLISWSPPANGYGYYRITYGETGGNSPVQEFTVPVGRGTATI

SGLKPGVDYTITVYAVEYTYKGSGYYHRPISINYRTEIEPKSSGSTHTCPPCPAPELLGGS

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFFLYSKLTVDK

SRWQQGNVFSCSVMHEALHNHYTQKSLSLSPG

PRD290 has the following hinge: EPKSSGSTHTCPPCPAPELLGGSS and a human IgG1 Fc.

PRD293:

(SEQ ID NO: 125)
EPKSSGSTHTCPPCPAPELLGGSSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGAGGG

GSGGVSDVPRDLEVVAATPTSLLISWSPPANGYGYYRITYGETGGNSPVQEFTVPVGRG

TATISGLKPGVDYTITVYAVEYTYKGSGYYHRPISINYRTEI

PRD293 has the following hinge: EPKSSGSTHTCPPCPAPELLGGSS and the following linker: AGGGGSG and a human IgG1 Fc.

PRD713:

(SEQ ID NO: 126)
GVSDVPRDLEVVAATPTSLLISWGHYPLHVRYYRITYGETGGNSPVQEFTVPPRSHTATI

SGLKPGVDYTITVYAVTYYAQENYKEIPISINYRTEIEPKSSGSTHTCPPCPAPELLGGSSV

FLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSR

WQQGNVFSCSVMHEALHNHYTQKSLSLSPGK

PRD713 has the following hinge: EPKSSGSTHTCPPCPAPELLGGSS and a human IgG1 Fc.

PRD239:

(SEQ ID NO: 127)
EPKSSGSTHTCPPCPAPELLGGSSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGAGGG

GSGGVSDVPRDLEVVAATPTSLLISWGHYPLHVRYYRITYGETGGNSPVQEFTVPPRSH

TATISGLKPGVDYTITVYAVTYYAQENYKEIPISINYRTEAS

PRD239 has the following hinge: EPKSSGSTHTCPPCPAPELLGGSS and the following linker AGGGGSG and a human IgG1 Fc.

-continued

C7FL-Fc (PRD1309):
(SEQ ID NO: 128)
GSVSDVPRDLEVVAATPTSLLISWRHPHFPTRYYRITYGETGGNSPVQEFTVPLQPPTATI

SGLKPGVDYTITVYAVTDGRNGRLLSIPISINYRTEIEPKSSDKTHTCPPCPAPELLGGSSV

FLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSR

WQQGNVFSCSVMHEALHNHYTQKSLSLSPGK

C7FL-Fc (PRD1309) has the following hinge:

EPKSSDKTHTCPPCPAPELLGGSS and a human IgG1 Fc.

C7FL-Fc (PRD1308):
(SEQ ID NO: 129)
GSVSDVPRDLEVVAATPTSLLISWRHPHFPTRYYRITYGETGGNSPVQEFTVPLQPPTATI

SGLKPGVDYTITVYAVTDGRNGRLLSIPISINYRTEIEPKSSDKTHTCPPCPAPELLGGPSV

FLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSR

WQQGNVFSCSVMHEALHNHYTQKSLSLSPGK

C7FL-Fc (PRD1308) has the following hinge:

EPKSSDKTHTCPPCPAPELLGGPS and a human IgG1 Fc.

PRD461 is a fusion protein comprising an Fc linked to the anti-PCSK9 Adnectin 2013E01, whose sequence is provided in WO2011/130354. The amino acid sequence for the anti anti-PCSK9 adnectins 1784F03 and 1813E02 are provided in WO2011/130354. The amino acid sequence of the anti-IL-23 adnectin 1571G04 is provided in WO2011/103105.

INCORPORATION BY REFERENCE

All documents and references described herein are individually incorporated by reference to into this document to the same extent as if there were written in this document in full or in part.

The invention claimed is:

1. A polypeptide comprising an immunoglobulin IgG Fc domain and a heterologous polypeptide, wherein the heterologous polypeptide is fused to the N-terminus or the C-terminus of the Fc domain by a polypeptide linker, wherein the polypeptide linker comprises an amino acid sequence selected from the group consisting of SEQ ID NOs: 51-54, 63-65 and 84.

2. The polypeptide of claim 1, wherein the polypeptide linker comprises SEQ ID NO: 84.

3. The polypeptide of claim 1, wherein the heterologous polypeptide is fused to the C-terminus of the Fc domain.

4. The polypeptide of claim 1, wherein the heterologous polypeptide is fused to the N-terminus of the Fc domain.

5. The polypeptide of claim 1, wherein the heterologous polypeptide comprises a $^{10}$Fn3 domain.

6. The polypeptide of claim 1, wherein the immunoglobulin Fc domain comprises a hinge or a portion thereof.

7. The polypeptide of claim 1, wherein the polypeptide linker consists of an amino acid sequence selected from the group consisting of SEQ ID NOs: 51-54, 63-65 and 84.

* * * * *

SEQUENCE LISTING

```
<160> NUMBER OF SEQ ID NOS: 177

<210> SEQ ID NO 1
<211> LENGTH: 94
<212> TYPE: PRT
<213> ORGANISM: Homo sapiens

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 2
<211> LENGTH: 137
```

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: /note="see specification as filed for detailed
      description of substitutions and preferred embodiments"
<220> FEATURE:
<221> NAME/KEY: MOD_RES
<222> LOCATION: (7)..(21)
<223> OTHER INFORMATION: Any amino acid
<220> FEATURE:
<221> NAME/KEY: misc_feature
<222> LOCATION: (7)..(21)
<223> OTHER INFORMATION: /note="This region may encompass 1 to 15
      residues"
<220> FEATURE:
<221> NAME/KEY: MOD_RES
<222> LOCATION: (26)..(45)
<223> OTHER INFORMATION: Any amino acid
<220> FEATURE:
<221> NAME/KEY: misc_feature
<222> LOCATION: (26)..(45)
<223> OTHER INFORMATION: /note="This region may encompass 2 to 20
      residues"
<220> FEATURE:
<221> NAME/KEY: MOD_RES
<222> LOCATION: (54)..(73)
<223> OTHER INFORMATION: Any amino acid
<220> FEATURE:
<221> NAME/KEY: misc_feature
<222> LOCATION: (54)..(73)
<223> OTHER INFORMATION: /note="This region may encompass 2 to 20
      residues"
<220> FEATURE:
<221> NAME/KEY: MOD_RES
<222> LOCATION: (79)..(88)
<223> OTHER INFORMATION: Any amino acid
<220> FEATURE:
<221> NAME/KEY: misc_feature
<222> LOCATION: (79)..(88)
<223> OTHER INFORMATION: /note="This region may encompass 2 to 20
      residues"
<220> FEATURE:
<221> NAME/KEY: MOD_RES
<222> LOCATION: (92)..(101)
<223> OTHER INFORMATION: Any amino acid
<220> FEATURE:
<221> NAME/KEY: misc_feature
<222> LOCATION: (92)..(101)
<223> OTHER INFORMATION: /note="This region may encompass 2 to 20
      residues"
<220> FEATURE:
<221> NAME/KEY: MOD_RES
<222> LOCATION: (111)..(130)
<223> OTHER INFORMATION: Any amino acid
<220> FEATURE:
<221> NAME/KEY: misc_feature
<222> LOCATION: (111)..(130)
<223> OTHER INFORMATION: /note="This region may encompass 2 to 20
      residues"

<400> SEQUENCE: 2

Glu Val Val Ala Ala Thr Xaa Xaa Xaa Xaa Xaa Xaa Xaa Xaa Xaa
1               5                   10                  15

Xaa Xaa Xaa Xaa Xaa Ser Leu Leu Ile Xaa Xaa Xaa Xaa Xaa Xaa
                20                  25                  30

Xaa Xaa Xaa Xaa Xaa Xaa Xaa Xaa Xaa Xaa Xaa Xaa Tyr Tyr Arg
            35                  40                  45

Ile Thr Tyr Gly Glu Xaa Xaa Xaa Xaa Xaa Xaa Xaa Xaa Xaa Xaa
    50                  55                  60

Xaa Xaa Xaa Xaa Xaa Xaa Xaa Xaa Xaa Gln Glu Phe Thr Val Xaa Xaa
65                  70                  75                  80
```

Xaa Xaa Xaa Xaa Xaa Xaa Xaa Xaa Ala Thr Ile Xaa Xaa Xaa Xaa
                85                  90                  95

Xaa Xaa Xaa Xaa Xaa Asp Tyr Thr Ile Thr Val Tyr Ala Val Xaa Xaa
                100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Ile Ser Ile Asn Tyr Arg Thr
    130                 135

<210> SEQ ID NO 3
<211> LENGTH: 98
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: /note="see specification as filed for detailed
      description of substitutions and preferred embodiments"
<220> FEATURE:
<221> NAME/KEY: MOD_RES
<222> LOCATION: (13)..(22)
<223> OTHER INFORMATION: Any amino acid
<220> FEATURE:
<221> NAME/KEY: misc_feature
<222> LOCATION: (13)..(22)
<223> OTHER INFORMATION: /note="This region may encompass 2 to 20
      residues"
<220> FEATURE:
<221> NAME/KEY: MOD_RES
<222> LOCATION: (43)..(52)
<223> OTHER INFORMATION: Any amino acid
<220> FEATURE:
<221> NAME/KEY: misc_feature
<222> LOCATION: (43)..(52)
<223> OTHER INFORMATION: /note="This region may encompass 2 to 20
      residues"
<220> FEATURE:
<221> NAME/KEY: MOD_RES
<222> LOCATION: (72)..(91)
<223> OTHER INFORMATION: Any amino acid
<220> FEATURE:
<221> NAME/KEY: misc_feature
<222> LOCATION: (72)..(91)
<223> OTHER INFORMATION: /note="This region may encompass 2 to 20
      residues"

<400> SEQUENCE: 3

Glu Val Val Ala Ala Thr Pro Thr Ser Leu Leu Ile Xaa Xaa Xaa Xaa
1               5                   10                  15

Xaa Xaa Xaa Xaa Xaa Xaa Tyr Tyr Arg Ile Thr Tyr Gly Glu Thr Gly
                20                  25                  30

Gly Asn Ser Pro Val Gln Glu Phe Thr Val Xaa Xaa Xaa Xaa Xaa Xaa
            35                  40                  45

Xaa Xaa Xaa Xaa Ala Thr Ile Ser Gly Leu Lys Pro Gly Val Asp Tyr
    50                  55                  60

Thr Ile Thr Val Tyr Ala Val Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Ile Ser Ile Asn Tyr
                85                  90                  95

Arg Thr

<210> SEQ ID NO 4
<211> LENGTH: 10
<212> TYPE: PRT
<213> ORGANISM: Artificial Sequence -continued

```
<220> FEATURE:
<223> OTHER INFORMATION: Synthetic peptide

<400> SEQUENCE: 4

Met Gly Val Ser Asp Val Pro Arg Asp Leu
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5

Val Ser Asp Val Pro Arg Asp Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Gly Val Ser Asp Val Pro Arg Asp Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: /replace=" "
<220> FEATURE:
<221> NAME/KEY: misc_feature
<222> LOCATION: (1)..(2)
<223> OTHER INFORMATION: /note="Residues given in the sequence have no
      preference with respect to those in the annotations for said
      positions"
<220> FEATURE:
<221> NAME/KEY: VARIANT
<222> LOCATION: (2)..(2)
<223> OTHER INFORMATION: /replace=" "

<400> SEQUENCE: 7

Met Gly Ser Asp Val Pro Arg Asp Leu
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: /replace=" "
<220> FEATURE:
<221> NAME/KEY: misc_feature
<222> LOCATION: (1)..(2)
<223> OTHER INFORMATION: /note="Residues given in the sequence have no
      preference with respect to those in the annotations for said
      positions"
<220> FEATURE:
```

```
<221> NAME/KEY: VARIANT
<222> LOCATION: (2)..(2)
<223> OTHER INFORMATION: /replace=" "

<400> SEQUENCE: 8

Met Gly Asp Val Pro Arg Asp Leu
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: /replace=" "
<220> FEATURE:
<221> NAME/KEY: misc_feature
<222> LOCATION: (1)..(2)
<223> OTHER INFORMATION: /note="Residues given in the sequence have no
     preference with respect to those in the annotations for said
     positions"
<220> FEATURE:
<221> NAME/KEY: VARIANT
<222> LOCATION: (2)..(2)
<223> OTHER INFORMATION: /replace=" "

<400> SEQUENCE: 9

Met Gly Val Pro Arg Asp Leu
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: /replace=" "
<220> FEATURE:
<221> NAME/KEY: misc_feature
<222> LOCATION: (1)..(2)
<223> OTHER INFORMATION: /note="Residues given in the sequence have no
     preference with respect to those in the annotations for said
     positions"
<220> FEATURE:
<221> NAME/KEY: VARIANT
<222> LOCATION: (2)..(2)
<223> OTHER INFORMATION: /replace=" "

<400> SEQUENCE: 10

Met Gly Pro Arg Asp Leu
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: /replace=" "
<220> FEATURE:
<221> NAME/KEY: misc_feature
<222> LOCATION: (1)..(2)
<223> OTHER INFORMATION: /note="Residues given in the sequence have no
     preference with respect to those in the annotations for said
```

```
                      positions"
<220> FEATURE:
<221> NAME/KEY: VARIANT
<222> LOCATION: (2)..(2)
<223> OTHER INFORMATION: /replace=" "

<400> SEQUENCE: 11

Met Gly Arg Asp Leu
1               5

<210> SEQ ID NO 12
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: /replace=" "
<220> FEATURE:
<221> NAME/KEY: misc_feature
<222> LOCATION: (1)..(2)
<223> OTHER INFORMATION: /note="Residues given in the sequence have no
      preference with respect to those in the annotations for said
      positions"
<220> FEATURE:
<221> NAME/KEY: VARIANT
<222> LOCATION: (2)..(2)
<223> OTHER INFORMATION: /replace=" "

<400> SEQUENCE: 12

Met Gly Asp Leu
1

<210> SEQ ID NO 13
<211> LENGTH: 4
<212> TYPE: PRT
<213> ORGANISM: Artificial Sequence
<220> FEATURE:
<223> OTHER INFORMATION: Synthetic peptide

<400> SEQUENCE: 13

Glu Ile Glu Lys
1

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide

<400> SEQUENCE: 14

Glu Gly Ser Gly Cys
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Glu Ile Glu Lys Pro Cys Gln
1               5

<210> SEQ ID NO 16
```

<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Glu Ile Glu Lys Pro Ser Gln
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic peptide

<400> SEQUENCE: 17

Glu Ile Glu Lys Pro
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic peptide

<400> SEQUENCE: 18

Glu Ile Glu Lys Pro Ser
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide

<400> SEQUENCE: 19

Glu Ile Glu Lys Pro Cys
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide

<400> SEQUENCE: 20

Glu Ile Asp Lys Pro Ser Gln
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide

<400> SEQUENCE: 21

Glu Ile Asp Lys Pro Ser Gln Leu Glu
1               5

<210> SEQ ID NO 22
<211> LENGTH: 330

<212> TYPE: PRT
<213> ORGANISM: Homo sapiens

<400> SEQUENCE: 22

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 23
<211> LENGTH: 16
<212> TYPE: PRT
<213> ORGANISM: Homo sapiens

<400> SEQUENCE: 23

```
Asp Lys Thr His Thr Cys Pro Pro Cys Pro Ala Pro Glu Leu Leu Gly
1               5                   10                  15
```

```
<210> SEQ ID NO 24
<211> LENGTH: 24
<212> TYPE: PRT
<213> ORGANISM: Artificial Sequence
<220> FEATURE:
<223> OTHER INFORMATION: Synthetic peptide

<400> SEQUENCE: 24

Glu Pro Lys Ser Ser Asp Lys Thr His Thr Cys Pro Pro Cys Pro Ala
1               5                   10                  15

Pro Glu Leu Leu Gly Gly Pro Ser
            20

<210> SEQ ID NO 25
<211> LENGTH: 24
<212> TYPE: PRT
<213> ORGANISM: Artificial Sequence
<220> FEATURE:
<223> OTHER INFORMATION: Synthetic peptide

<400> SEQUENCE: 25

Glu Pro Lys Ser Ser Asp Lys Thr His Thr Cys Pro Pro Cys Pro Ala
1               5                   10                  15

Pro Glu Leu Leu Gly Gly Ser Ser
            20

<210> SEQ ID NO 26
<211> LENGTH: 24
<212> TYPE: PRT
<213> ORGANISM: Artificial Sequence
<220> FEATURE:
<223> OTHER INFORMATION: Synthetic peptide

<400> SEQUENCE: 26

Glu Pro Lys Ser Ser Gly Ser Thr His Thr Cys Pro Pro Cys Pro Ala
1               5                   10                  15

Pro Glu Leu Leu Gly Gly Ser Ser
            20

<210> SEQ ID NO 27
<211> LENGTH: 19
<212> TYPE: PRT
<213> ORGANISM: Artificial Sequence
<220> FEATURE:
<223> OTHER INFORMATION: Synthetic peptide

<400> SEQUENCE: 27

Asp Lys Thr His Thr Cys Pro Pro Cys Pro Ala Pro Glu Leu Leu Gly
1               5                   10                  15

Gly Pro Ser

<210> SEQ ID NO 28
<211> LENGTH: 19
<212> TYPE: PRT
<213> ORGANISM: Artificial Sequence
<220> FEATURE:
<223> OTHER INFORMATION: Synthetic peptide

<400> SEQUENCE: 28

Asp Lys Thr His Thr Cys Pro Pro Cys Pro Ala Pro Glu Leu Leu Gly
1               5                   10                  15

Gly Ser Ser
```

-continued

```
<210> SEQ ID NO 29
<211> LENGTH: 20
<212> TYPE: PRT
<213> ORGANISM: Artificial Sequence
<220> FEATURE:
<223> OTHER INFORMATION: Synthetic peptide

<400> SEQUENCE: 29

Met Glu Thr Asp Thr Leu Leu Leu Trp Val Leu Leu Leu Trp Val Pro
 1               5                  10                  15

Gly Ser Thr Gly
            20

<210> SEQ ID NO 30
<211> LENGTH: 330
<212> TYPE: PRT
<213> ORGANISM: Artificial Sequence
<220> FEATURE:
<223> OTHER INFORMATION: Synthetic polypeptide

<400> SEQUENCE: 30

Gly Val Ser Asp Val Pro Arg Asp Leu Glu Val Val Ala Ala Thr Pro
 1               5                  10                  15

Thr Ser Leu Leu Ile Ser Trp Val Pro Pro Ser Asp Asp Tyr Gly Tyr
            20                  25                  30

Tyr Arg Ile Thr Tyr Gly Glu Thr Gly Gly Asn Ser Pro Val Gln Glu
        35                  40                  45

Phe Thr Val Pro Ile Gly Lys Gly Thr Ala Thr Ile Ser Gly Leu Lys
    50                  55                  60

Pro Gly Val Asp Tyr Thr Ile Thr Val Tyr Ala Val Glu Phe Pro Trp
65                  70                  75                  80

Pro His Ala Gly Tyr Tyr His Arg Pro Ile Ser Ile Asn Tyr Arg Thr
                85                  90                  95

Glu Ile Glu Pro Lys Ser Ser Gly Ser Thr His Thr Cys Pro Pro Cys
            100                 105                 110

Pro Ala Pro Glu Leu Leu Gly Gly Ser Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 31
<211> LENGTH: 208
<212> TYPE: PRT
<213> ORGANISM: Homo sapiens

<400> SEQUENCE: 31

Val Phe Leu Phe Pro Pro Lys Pro Lys Asp Thr Leu Met Ile Ser Arg
1               5                   10                  15

Thr Pro Glu Val Thr Cys Val Val Val Asp Val Ser His Glu Asp Pro
            20                  25                  30

Glu Val Lys Phe Asn Trp Tyr Val Asp Gly Val Glu Val His Asn Ala
        35                  40                  45

Lys Thr Lys Pro Arg Glu Glu Gln Tyr Asn Ser Thr Tyr Arg Val Val
    50                  55                  60

Ser Val Leu Thr Val Leu His Gln Asp Trp Leu Asn Gly Lys Glu Tyr
65                  70                  75                  80

Lys Cys Lys Val Ser Asn Lys Ala Leu Pro Ala Pro Ile Glu Lys Thr
                85                  90                  95

Ile Ser Lys Ala Lys Gly Gln Pro Arg Glu Pro Gln Val Tyr Thr Leu
            100                 105                 110

Pro Pro Ser Arg Asp Glu Leu Thr Lys Asn Gln Val Ser Leu Thr Cys
        115                 120                 125

Leu Val Lys Gly Phe Tyr Pro Ser Asp Ile Ala Val Glu Trp Glu Ser
    130                 135                 140

Asn Gly Gln Pro Glu Asn Asn Tyr Lys Thr Thr Pro Pro Val Leu Asp
145                 150                 155                 160

Ser Asp Gly Ser Phe Phe Leu Tyr Ser Lys Leu Thr Val Asp Lys Ser
                165                 170                 175

Arg Trp Gln Gln Gly Asn Val Phe Ser Cys Ser Val Met His Glu Ala
            180                 185                 190

Leu His Asn His Tyr Thr Gln Lys Ser Leu Ser Leu Ser Pro Gly Lys
        195                 200                 205

<210> SEQ ID NO 32
<211> LENGTH: 10
<212> TYPE: PRT
<213> ORGANISM: Artificial Sequence
<220> FEATURE:
<223> OTHER INFORMATION: Synthetic peptide

<400> SEQUENCE: 32

Gly Ser Gly Ser Gly Ser Gly Ser Gly Ser
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic peptide

<400> SEQUENCE: 33
```

```
Gly Ser Gly Ser Gly Ser Gly Ser Gly Ser Gly Ser
1               5                   10
```

<210> SEQ ID NO 34
<211> LENGTH: 20
<212> TYPE: PRT
<213> ORGANISM: Artificial Sequence
<220> FEATURE:
<223> OTHER INFORMATION: Synthetic peptide

<400> SEQUENCE: 34

```
Gly Ser Gly Ser Gly Ser Gly Ser Gly Ser Gly Ser Gly Ser Gly Ser
1               5                   10                  15

Gly Ser Gly Ser
            20
```

<210> SEQ ID NO 35
<211> LENGTH: 15
<212> TYPE: PRT
<213> ORGANISM: Artificial Sequence
<220> FEATURE:
<223> OTHER INFORMATION: Synthetic peptide

<400> SEQUENCE: 35

```
Gly Gly Gly Gly Ser Gly Gly Gly Gly Ser Gly Gly Gly Gly Ser
1               5                   10                  15
```

<210> SEQ ID NO 36
<211> LENGTH: 15
<212> TYPE: PRT
<213> ORGANISM: Artificial Sequence
<220> FEATURE:
<223> OTHER INFORMATION: Synthetic peptide

<400> SEQUENCE: 36

```
Gly Gly Gly Gly Ser Gly Gly Gly Ser Gly Gly Gly Ser Gly
1               5                   10                  15
```

<210> SEQ ID NO 37
<211> LENGTH: 7
<212> TYPE: PRT
<213> ORGANISM: Artificial Sequence
<220> FEATURE:
<223> OTHER INFORMATION: Synthetic peptide

<400> SEQUENCE: 37

```
Ala Gly Gly Gly Gly Ser Gly
1               5
```

<210> SEQ ID NO 38
<211> LENGTH: 8
<212> TYPE: PRT
<213> ORGANISM: Artificial Sequence
<220> FEATURE:
<223> OTHER INFORMATION: Synthetic peptide

<400> SEQUENCE: 38

```
Ala Gly Gly Gly Gly Ser Gly Gly
1               5
```

<210> SEQ ID NO 39
<211> LENGTH: 3
<212> TYPE: PRT
<213> ORGANISM: Artificial Sequence
<220> FEATURE:
<223> OTHER INFORMATION: Synthetic peptide

<400> SEQUENCE: 39

Gly Pro Gly
1

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide

<400> SEQUENCE: 40

Gly Pro Gly Pro Gly Pro Gly
1               5

<210> SEQ ID NO 41
<211> LENGTH: 11
<212> TYPE: PRT
<213> ORGANISM: Artificial Sequence
<220> FEATURE:
<223> OTHER INFORMATION: Synthetic peptide

<400> SEQUENCE: 41

Gly Pro Gly Pro Gly Pro Gly Pro Gly Pro Gly
1               5                   10

<210> SEQ ID NO 42
<211> LENGTH: 6
<212> TYPE: PRT
<213> ORGANISM: Artificial Sequence
<220> FEATURE:
<223> OTHER INFORMATION: Synthetic peptide

<400> SEQUENCE: 42

Pro Ala Pro Ala Pro Ala
1               5

<210> SEQ ID NO 43
<211> LENGTH: 12
<212> TYPE: PRT
<213> ORGANISM: Artificial Sequence
<220> FEATURE:
<223> OTHER INFORMATION: Synthetic peptide

<400> SEQUENCE: 43

Pro Ala Pro Ala Pro Ala Pro Ala Pro Ala Pro Ala
1               5                   10

<210> SEQ ID NO 44
<211> LENGTH: 18
<212> TYPE: PRT
<213> ORGANISM: Artificial Sequence
<220> FEATURE:
<223> OTHER INFORMATION: Synthetic peptide

<400> SEQUENCE: 44

Pro Ala Pro Ala Pro Ala Pro Ala Pro Ala Pro Ala Pro Ala Pro Ala
1               5                   10                  15

Pro Ala

<210> SEQ ID NO 45
<211> LENGTH: 8
<212> TYPE: PRT
<213> ORGANISM: Artificial Sequence
<220> FEATURE:
<223> OTHER INFORMATION: Synthetic peptide

```
<400> SEQUENCE: 45

Gln Pro Asp Glu Pro Gly Gly Ser
1               5

<210> SEQ ID NO 46
<211> LENGTH: 17
<212> TYPE: PRT
<213> ORGANISM: Artificial Sequence
<220> FEATURE:
<223> OTHER INFORMATION: Synthetic peptide

<400> SEQUENCE: 46

Glu Leu Gln Leu Glu Glu Ser Ala Ala Glu Ala Gln Asp Gly Glu Leu
1               5                   10                  15

Asp

<210> SEQ ID NO 47
<211> LENGTH: 6
<212> TYPE: PRT
<213> ORGANISM: Artificial Sequence
<220> FEATURE:
<223> OTHER INFORMATION: Synthetic peptide

<400> SEQUENCE: 47

Thr Val Ala Ala Pro Ser
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide

<400> SEQUENCE: 48

Gln Pro Asp Glu Pro Gly Gly Ser Gly
1               5

<210> SEQ ID NO 49
<211> LENGTH: 18
<212> TYPE: PRT
<213> ORGANISM: Artificial Sequence
<220> FEATURE:
<223> OTHER INFORMATION: Synthetic peptide

<400> SEQUENCE: 49

Glu Leu Gln Leu Glu Glu Ser Ala Ala Glu Ala Gln Asp Gly Glu Leu
1               5                   10                  15

Asp Gly

<210> SEQ ID NO 50
<211> LENGTH: 7
<212> TYPE: PRT
<213> ORGANISM: Artificial Sequence
<220> FEATURE:
<223> OTHER INFORMATION: Synthetic peptide

<400> SEQUENCE: 50

Thr Val Ala Ala Pro Ser Gly
1               5

<210> SEQ ID NO 51
<211> LENGTH: 31
<212> TYPE: PRT
```

```
<213> ORGANISM: Artificial Sequence
<220> FEATURE:
<223> OTHER INFORMATION: Synthetic polypeptide

<400> SEQUENCE: 51

Ser Cys Ser Val Ala Asp Trp Gln Met Pro Pro Tyr Val Val Leu
1               5                   10                  15

Asp Leu Pro Gln Glu Thr Leu Glu Glu Glu Thr Pro Gly Ala Asn
            20                  25                  30

<210> SEQ ID NO 52
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 52

Ser Cys Cys Val Ala Asp Trp Gln Met Pro Pro Tyr Val Val Leu
1               5                   10                  15

Asp Leu Pro Gln Glu Thr Leu Glu Glu Glu Thr Pro Gly Ala Asn
            20                  25                  30

<210> SEQ ID NO 53
<211> LENGTH: 26
<212> TYPE: PRT
<213> ORGANISM: Artificial Sequence
<220> FEATURE:
<223> OTHER INFORMATION: Synthetic peptide

<400> SEQUENCE: 53

Asp Trp Gln Met Pro Pro Pro Tyr Val Val Leu Asp Leu Pro Gln Glu
1               5                   10                  15

Thr Leu Glu Glu Glu Thr Pro Gly Ala Asn
            20                  25

<210> SEQ ID NO 54
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 54

Ser Cys Cys Val Ala Asp Trp Gln Met Pro Pro Pro Tyr Val Val Leu
1               5                   10                  15

Asp Leu Pro Gln Glu Thr Leu Glu Glu Glu Thr Pro Gly Ala Asn
            20                  25                  30

<210> SEQ ID NO 55
<211> LENGTH: 27
<212> TYPE: PRT
<213> ORGANISM: Artificial Sequence
<220> FEATURE:
<223> OTHER INFORMATION: Synthetic peptide

<400> SEQUENCE: 55

Tyr Leu Ala Met Thr Pro Leu Ile Pro Gln Ser Lys Asp Glu Asn Ser
1               5                   10                  15

Asp Asp Tyr Thr Thr Phe Asp Asp Val Gly Ser
            20                  25

<210> SEQ ID NO 56
<211> LENGTH: 15
```

```
<212> TYPE: PRT
<213> ORGANISM: Artificial Sequence
<220> FEATURE:
<223> OTHER INFORMATION: Synthetic peptide

<400> SEQUENCE: 56

Glu Leu Asp Val Cys Val Glu Glu Ala Glu Gly Glu Ala Pro Trp
1               5                   10                  15

<210> SEQ ID NO 57
<211> LENGTH: 18
<212> TYPE: PRT
<213> ORGANISM: Artificial Sequence
<220> FEATURE:
<223> OTHER INFORMATION: Synthetic peptide

<400> SEQUENCE: 57

Glu Leu Gln Leu Glu Glu Ser Cys Ala Glu Ala Gln Asp Gly Glu Leu
1               5                   10                  15

Asp Gly

<210> SEQ ID NO 58
<211> LENGTH: 13
<212> TYPE: PRT
<213> ORGANISM: Artificial Sequence
<220> FEATURE:
<223> OTHER INFORMATION: Synthetic peptide

<400> SEQUENCE: 58

Glu Gly Glu Val Ser Ala Asp Glu Gly Phe Glu Asn
1               5                   10

<210> SEQ ID NO 59
<211> LENGTH: 19
<212> TYPE: PRT
<213> ORGANISM: Artificial Sequence
<220> FEATURE:
<223> OTHER INFORMATION: Synthetic peptide

<400> SEQUENCE: 59

Lys Pro Thr His Val Asn Val Ser Val Val Met Ala Glu Val Asp Gly
1               5                   10                  15

Thr Cys Tyr

<210> SEQ ID NO 60
<211> LENGTH: 19
<212> TYPE: PRT
<213> ORGANISM: Artificial Sequence
<220> FEATURE:
<223> OTHER INFORMATION: Synthetic peptide

<400> SEQUENCE: 60

Lys Pro Thr His Val Asn Val Ser Val Val Met Ala Glu Val Asp Gly
1               5                   10                  15

Thr Cys Tyr

<210> SEQ ID NO 61
<211> LENGTH: 9
<212> TYPE: PRT
<213> ORGANISM: Artificial Sequence
<220> FEATURE:
<223> OTHER INFORMATION: Synthetic peptide

<400> SEQUENCE: 61

Tyr Val Thr Asp His Gly Pro Met Lys
```

-continued

```
<210> SEQ ID NO 62
<211> LENGTH: 18
<212> TYPE: PRT
<213> ORGANISM: Artificial Sequence
<220> FEATURE:
<223> OTHER INFORMATION: Synthetic peptide

<400> SEQUENCE: 62

Pro Thr Leu Tyr Asn Val Ser Leu Val Met Ser Asp Thr Ala Gly Thr
1               5                   10                  15

Cys Tyr

<210> SEQ ID NO 63
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: (2)..(2)
<223> OTHER INFORMATION: /replace="Ala" or "Gly"
<220> FEATURE:
<221> NAME/KEY: misc_feature
<222> LOCATION: (2)..(2)
<223> OTHER INFORMATION: /note="Residue given in the sequence has no
      preference with respect to those in the annotation for said
      position"

<400> SEQUENCE: 63

Ser Ser Ser Val Ala Asp Trp Gln Met Pro Pro Pro Tyr Val Val Leu
1               5                   10                  15

Asp Leu Pro Gln Glu Thr Leu Glu Glu Glu Thr Pro Gly Ala Asn
            20                  25                  30

<210> SEQ ID NO 64
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: (2)..(3)
<223> OTHER INFORMATION: /replace="Ala" or "Gly"
<220> FEATURE:
<221> NAME/KEY: misc_feature
<222> LOCATION: (2)..(3)
<223> OTHER INFORMATION: /note="Residues given in the sequence have no
      preference with respect to those in the annotations for said
      positions"

<400> SEQUENCE: 64

Ser Ser Ser Val Ala Asp Trp Gln Met Pro Pro Pro Tyr Val Val Leu
1               5                   10                  15

Asp Leu Pro Gln Glu Thr Leu Glu Glu Glu Thr Pro Gly Ala Asn
            20                  25                  30

<210> SEQ ID NO 65
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: (2)..(3)
```

```
<223> OTHER INFORMATION: /replace="Ala" or "Gly"
<220> FEATURE:
<221> NAME/KEY: misc_feature
<222> LOCATION: (2)..(3)
<223> OTHER INFORMATION: /note="Residues given in the sequence have no
      preference with respect to those in the annotations for said
      positions"

<400> SEQUENCE: 65

Ser Ser Ser Val Ala Asp Trp Gln Met Pro Pro Pro Tyr Val Val Leu
1               5                   10                  15

Asp Leu Pro Gln Glu Thr Leu Glu Glu Glu Thr Pro Gly Ala Asn
            20                  25                  30

<210> SEQ ID NO 66
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (5)..(5)
<223> OTHER INFORMATION: /replace="Ala" or "Gly"
<220> FEATURE:
<221> NAME/KEY: misc_feature
<222> LOCATION: (5)..(5)
<223> OTHER INFORMATION: /note="Residue given in the sequence has no
      preference with respect to those in the annotation for said
      position"

<400> SEQUENCE: 66

Glu Leu Asp Val Ser Val Glu Glu Ala Glu Gly Glu Ala Pro Trp
1               5                   10                  15

<210> SEQ ID NO 67
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (8)..(8)
<223> OTHER INFORMATION: /replace="Ala" or "Gly"
<220> FEATURE:
<221> NAME/KEY: misc_feature
<222> LOCATION: (8)..(8)
<223> OTHER INFORMATION: /note="Residue given in the sequence has no
      preference with respect to those in the annotation for said
      position"

<400> SEQUENCE: 67

Glu Leu Gln Leu Glu Glu Ser Ser Ala Glu Ala Gln Asp Gly Glu Leu
1               5                   10                  15

Asp Gly

<210> SEQ ID NO 68
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (18)..(18)
<223> OTHER INFORMATION: /replace="Ala" or "Gly"
<220> FEATURE:
<221> NAME/KEY: misc_feature
<222> LOCATION: (18)..(18)
<223> OTHER INFORMATION: /note="Residue given in the sequence has no
``` preference with respect to those in the annotation for said
      position"

<400> SEQUENCE: 68

Lys Pro Thr His Val Asn Val Ser Val Val Met Ala Glu Val Asp Gly
1               5                   10                  15

Thr Ser Tyr

<210> SEQ ID NO 69
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (18)..(18)
<223> OTHER INFORMATION: /replace="Ala" or "Gly"
<220> FEATURE:
<221> NAME/KEY: misc_feature
<222> LOCATION: (18)..(18)
<223> OTHER INFORMATION: /note="Residue given in the sequence has no
      preference with respect to those in the annotation for said
      position"

<400> SEQUENCE: 69

Lys Pro Thr His Val Asn Val Ser Val Val Met Ala Glu Val Asp Gly
1               5                   10                  15

Thr Ser Tyr

<210> SEQ ID NO 70
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (17)..(17)
<223> OTHER INFORMATION: /replace="Ala" or "Gly"
<220> FEATURE:
<221> NAME/KEY: misc_feature
<222> LOCATION: (17)..(17)
<223> OTHER INFORMATION: /note="Residue given in the sequence has no
      preference with respect to those in the annotation for said
      position"

<400> SEQUENCE: 70

Pro Thr Leu Tyr Asn Val Ser Leu Val Met Ser Asp Thr Ala Gly Thr
1               5                   10                  15

Ser Tyr

<210> SEQ ID NO 71
<211> LENGTH: 7
<212> TYPE: PRT
<213> ORGANISM: Artificial Sequence
<220> FEATURE:
<223> OTHER INFORMATION: Synthetic peptide

<400> SEQUENCE: 71

Pro Ser Thr Ser Thr Ser Thr
1               5

<210> SEQ ID NO 72
<211> LENGTH: 104
<212> TYPE: PRT
<213> ORGANISM: Artificial Sequence
<220> FEATURE:

<223> OTHER INFORMATION: Synthetic polypeptide

<400> SEQUENCE: 72

Met Gly Val Ser Asp Val Pro Arg Asp Leu Glu Val Val Ala Ala Thr
1               5                   10                  15

Pro Thr Ser Leu Leu Ile Ser Trp Val Pro Pro Ser Asp Asp Tyr Gly
            20                  25                  30

Tyr Tyr Arg Ile Thr Tyr Gly Glu Thr Gly Gly Asn Ser Pro Val Gln
        35                  40                  45

Glu Phe Thr Val Pro Ile Gly Lys Gly Thr Ala Thr Ile Ser Gly Leu
    50                  55                  60

Lys Pro Gly Val Asp Tyr Thr Ile Thr Val Tyr Ala Val Glu Phe Pro
65                  70                  75                  80

Trp Pro His Ala Gly Tyr Tyr His Arg Pro Ile Ser Ile Asn Tyr Arg
                85                  90                  95

Thr Glu Ile Glu Lys Pro Cys Gln
            100

<210> SEQ ID NO 73
<211> LENGTH: 314
<212> TYPE: DNA
<213> ORGANISM: Artificial Sequence
<220> FEATURE:
<223> OTHER INFORMATION: Synthetic polynucleotide

<400> SEQUENCE: 73
atgggagttt ctgatgtgcc gcgcgacctg gaagtggttg ctgccacccc caccagcctg      60
ctgatcagct gggtcccgcc ttcagatgat tacggttatt accgcatcac ttacggcgaa     120
acaggaggca atagccctgt ccaggagttc actgtgccta ttggtaaagg aacagctacc     180
atcagcggcc ttaaacctgg cgttgattat accatcactg tgtatgctgt cgagtttccg     240
tggccacatg ctggttacta tcatcggcca atttccatta attaccgcac agaaattgag     300
aaaccatgcc agtg                                                      314

<210> SEQ ID NO 74
<211> LENGTH: 104
<212> TYPE: PRT
<213> ORGANISM: Artificial Sequence
<220> FEATURE:
<223> OTHER INFORMATION: Synthetic polypeptide

<400> SEQUENCE: 74

Met Gly Val Ser Asp Val Pro Arg Asp Leu Glu Val Val Ala Ala Thr
1               5                   10                  15

Pro Thr Ser Leu Leu Ile Ser Trp Val Pro Pro Ser Asp Asp Tyr Gly
            20                  25                  30

Tyr Tyr Arg Ile Thr Tyr Gly Glu Thr Gly Gly Asn Ser Pro Val Gln
        35                  40                  45

Glu Phe Thr Val Pro Ile Gly Lys Gly Thr Ala Thr Ile Ser Gly Leu
    50                  55                  60

Lys Pro Gly Val Asp Tyr Thr Ile Thr Val Tyr Ala Val Glu Phe Pro
65                  70                  75                  80

Trp Pro His Ala Gly Tyr Tyr His Arg Pro Ile Ser Ile Asn Tyr Arg
                85                  90                  95

Thr Glu Ile Asp Lys Pro Ser Gln
            100

<210> SEQ ID NO 75
<211> LENGTH: 330
<212> TYPE: DNA
<213> ORGANISM: Artificial Sequence
<220> FEATURE:
<223> OTHER INFORMATION: Synthetic polynucleotide

<400> SEQUENCE: 75

```
atgggagttt ctgatgtgcc gcgcgacctg gaagtggttg ctgccacccc caccagcctg      60
ctgatcagct gggtcccgcc ttcagatgat tacggttatt accgcatcac ttacggcgaa     120
acaggaggca atagccctgt ccaggagttc actgtgccta ttggtaaagg aacagctacc     180
atcagcggcc ttaaacctgg cgttgattat accatcactg tgtatgctgt cgagtttccg     240
tggccacatg ctggttacta tcatcggcca atttccatta attaccgcac agaaattgac     300
aaaccatccc agcaccatca ccaccaccac                                      330
```

<210> SEQ ID NO 76
<211> LENGTH: 101
<212> TYPE: PRT
<213> ORGANISM: Artificial Sequence
<220> FEATURE:
<223> OTHER INFORMATION: Synthetic polypeptide

<400> SEQUENCE: 76

```
Met Gly Val Ser Asp Val Pro Arg Asp Leu Glu Val Val Ala Ala Thr
1               5                  10                  15
Pro Thr Ser Leu Leu Ile Ser Trp Val Pro Pro Ser Asp Asp Tyr Gly
            20                  25                  30
Tyr Tyr Arg Ile Thr Tyr Gly Glu Thr Gly Gly Asn Ser Pro Val Gln
        35                  40                  45
Glu Phe Thr Val Pro Ile Gly Lys Gly Thr Ala Thr Ile Ser Gly Leu
    50                  55                  60
Lys Pro Gly Val Asp Tyr Thr Ile Thr Val Tyr Ala Val Glu Phe Pro
65                  70                  75                  80
Trp Pro His Ala Gly Tyr Tyr His Arg Pro Ile Ser Ile Asn Tyr Arg
                85                  90                  95
Thr Gly Ser Gly Cys
            100
```

<210> SEQ ID NO 77
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 77

```
atgggagttt ctgatgtgcc gcgcgacctg gaagtggttg ctgccacccc caccagcctg      60
ctgatcagct gggtcccgcc ttcagatgat tacggttatt accgcatcac ttacggcgaa     120
acaggaggca atagccctgt ccaggagttc actgtgccta ttggtaaagg aacagctacc     180
atcagcggcc ttaaacctgg cgttgattat accatcactg tgtatgctgt cgagtttccg     240
tggccacatg ctggttacta tcatcggcca atttccatta attaccgcac aggtagcggt     300
tgccaccatc accaccatca c                                               321
```

<210> SEQ ID NO 78
<211> LENGTH: 104
<212> TYPE: PRT
<213> ORGANISM: Artificial Sequence
<220> FEATURE:
<223> OTHER INFORMATION: Synthetic polypeptide

<400> SEQUENCE: 78

Met Gly Val Ser Asp Val Pro Arg Asp Leu Glu Val Val Ala Ala Thr
1               5                   10                  15

Pro Thr Ser Leu Leu Ile Ser Trp Pro Pro Ser His Gly Tyr Gly
            20                  25                  30

Tyr Tyr Arg Ile Thr Tyr Gly Glu Thr Gly Asn Ser Pro Val Gln
        35                  40                  45

Glu Phe Thr Val Pro Pro Gly Lys Gly Thr Ala Thr Ile Ser Gly Leu
50                  55                  60

Lys Pro Gly Val Asp Tyr Thr Ile Thr Val Tyr Ala Val Glu Tyr Pro
65                  70                  75                  80

Tyr Lys His Ser Gly Tyr Tyr His Arg Pro Ile Ser Ile Asn Tyr Arg
                85                  90                  95

Thr Glu Ile Asp Lys Pro Cys Gln
            100

<210> SEQ ID NO 79
<211> LENGTH: 330
<212> TYPE: DNA
<213> ORGANISM: Artificial Sequence
<220> FEATURE:
<223> OTHER INFORMATION: Synthetic polynucleotide

<400> SEQUENCE: 79
atgggagttt ctgatgtgcc gcgcgacctg gaagtggttg ctgccacccc caccagcctg     60
ctgatcagct ggccgccgcc gtctcatggt tacggttatt accgcatcac ttacggcgaa    120
acaggaggca atagccctgt ccaggagttc actgtgccgc ctggtaaagg tacagctacc    180
atcagcggcc ttaaacctgg cgttgattat accatcactg tgtatgctgt cgaatacccg    240
tacaaacatt ctggttacta ccatcgtcca atttccatta attaccgcac agaaattgac    300
aaaccatgcc agcaccatca ccaccaccac                                    330

<210> SEQ ID NO 80
<211> LENGTH: 25
<212> TYPE: PRT
<213> ORGANISM: Artificial Sequence
<220> FEATURE:
<223> OTHER INFORMATION: Synthetic peptide

<400> SEQUENCE: 80

Gly Gly Gly Gly Ser Gly Gly Gly Ser Gly Gly Gly Ser Gly
1               5                   10                  15

Gly Gly Ser Gly Gly Gly Gly Ser
            20                  25

<210> SEQ ID NO 81
<211> LENGTH: 5
<212> TYPE: PRT
<213> ORGANISM: Artificial Sequence
<220> FEATURE:
<223> OTHER INFORMATION: Synthetic peptide

<400> SEQUENCE: 81

Gln Pro Asp Glu Pro
1               5

<210> SEQ ID NO 82

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 82

Pro Val Pro Pro Pro Pro Pro
1               5

<210> SEQ ID NO 83
<211> LENGTH: 11
<212> TYPE: PRT
<213> ORGANISM: Artificial Sequence
<220> FEATURE:
<223> OTHER INFORMATION: Synthetic peptide

<400> SEQUENCE: 83

Glu Asp Glu Asp Glu Asp Glu Asp Glu Asp Glu
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Synthetic peptide

<400> SEQUENCE: 84

Asp Leu Pro Gln Glu Thr Leu Glu Glu Glu Thr Pro Gly Ala
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic peptide

<400> SEQUENCE: 85

Val Pro Ser Thr Pro Pro Thr Pro Ser Pro Ser Thr
1               5                   10

<210> SEQ ID NO 86
<211> LENGTH: 17
<212> TYPE: PRT
<213> ORGANISM: Artificial Sequence
<220> FEATURE:
<223> OTHER INFORMATION: Synthetic peptide

<400> SEQUENCE: 86

Glu Leu Gln Leu Glu Glu Ser Ala Ala Glu Ala Gln Glu Gly Glu Leu
1               5                   10                  15

Glu

<210> SEQ ID NO 87
<211> LENGTH: 18
<212> TYPE: PRT
<213> ORGANISM: Artificial Sequence
<220> FEATURE:
<223> OTHER INFORMATION: Synthetic peptide

<400> SEQUENCE: 87

Glu Ser Pro Lys Ala Gln Ala Ser Ser Val Pro Thr Ala Gln Pro Gln
1               5                   10                  15

Ala Glu
```

<210> SEQ ID NO 88
<211> LENGTH: 6
<212> TYPE: PRT
<213> ORGANISM: Artificial Sequence
<220> FEATURE:
<223> OTHER INFORMATION: Synthetic peptide

<400> SEQUENCE: 88

Pro Ala Val Pro Pro Pro
1               5

<210> SEQ ID NO 89
<211> LENGTH: 15
<212> TYPE: PRT
<213> ORGANISM: Artificial Sequence
<220> FEATURE:
<223> OTHER INFORMATION: Synthetic peptide

<400> SEQUENCE: 89

Glu Pro Lys Ser Ser Asp Lys Thr His Thr Cys Pro Pro Cys Pro
1               5                   10                  15

<210> SEQ ID NO 90
<211> LENGTH: 13
<212> TYPE: PRT
<213> ORGANISM: Artificial Sequence
<220> FEATURE:
<223> OTHER INFORMATION: Synthetic peptide

<400> SEQUENCE: 90

Val Pro Ser Thr Pro Pro Thr Pro Ser Pro Ser Thr Gly
1               5                   10

<210> SEQ ID NO 91
<211> LENGTH: 20
<212> TYPE: PRT
<213> ORGANISM: Artificial Sequence
<220> FEATURE:
<223> OTHER INFORMATION: Synthetic peptide

<400> SEQUENCE: 91

Val Pro Ser Thr Pro Pro Thr Pro Ser Pro Ser Thr Pro Pro Thr Pro
1               5                   10                  15

Ser Pro Ser Gly
            20

<210> SEQ ID NO 92
<211> LENGTH: 16
<212> TYPE: PRT
<213> ORGANISM: Artificial Sequence
<220> FEATURE:
<223> OTHER INFORMATION: Synthetic peptide

<400> SEQUENCE: 92

Gly Arg Gly Gly Glu Glu Lys Lys Lys Glu Lys Glu Lys Glu Glu Gly
1               5                   10                  15

<210> SEQ ID NO 93
<211> LENGTH: 25
<212> TYPE: PRT
<213> ORGANISM: Artificial Sequence
<220> FEATURE:
<223> OTHER INFORMATION: Synthetic peptide

<400> SEQUENCE: 93

```
Gly Arg Gly Gly Glu Glu Lys Lys Glu Lys Glu Lys Glu Glu Gln
1               5                   10                  15

Glu Glu Arg Glu Thr Lys Thr Pro Gly
            20                  25
```

<210> SEQ ID NO 94
<211> LENGTH: 10
<212> TYPE: PRT
<213> ORGANISM: Artificial Sequence
<220> FEATURE:
<223> OTHER INFORMATION: Synthetic peptide

<400> SEQUENCE: 94

```
Glu Ser Pro Lys Ala Gln Ala Ser Ser Gly
1               5                   10
```

<210> SEQ ID NO 95
<211> LENGTH: 19
<212> TYPE: PRT
<213> ORGANISM: Artificial Sequence
<220> FEATURE:
<223> OTHER INFORMATION: Synthetic peptide

<400> SEQUENCE: 95

```
Glu Ser Pro Lys Ala Gln Ala Ser Ser Val Pro Thr Ala Gln Pro Gln
1               5                   10                  15

Ala Glu Gly
```

<210> SEQ ID NO 96
<211> LENGTH: 23
<212> TYPE: PRT
<213> ORGANISM: Artificial Sequence
<220> FEATURE:
<223> OTHER INFORMATION: Synthetic peptide

<400> SEQUENCE: 96

```
Ser Val Glu Glu Lys Lys Lys Glu Lys Glu Lys Glu Glu Gln Glu Glu
1               5                   10                  15

Arg Glu Thr Lys Thr Pro Gly
            20
```

<210> SEQ ID NO 97
<211> LENGTH: 24
<212> TYPE: PRT
<213> ORGANISM: Artificial Sequence
<220> FEATURE:
<223> OTHER INFORMATION: Synthetic peptide

<400> SEQUENCE: 97

```
Pro Ser Val Glu Glu Lys Lys Lys Glu Lys Glu Lys Glu Glu Gln Glu
1               5                   10                  15

Glu Arg Glu Thr Lys Thr Pro Gly
            20
```

<210> SEQ ID NO 98
<211> LENGTH: 24
<212> TYPE: PRT
<213> ORGANISM: Artificial Sequence
<220> FEATURE:
<223> OTHER INFORMATION: Synthetic peptide

<400> SEQUENCE: 98

```
Gly Ser Val Glu Glu Lys Lys Lys Glu Lys Glu Lys Glu Glu Gln Glu
1               5                   10                  15
```

Glu Arg Glu Thr Lys Thr Pro Gly
            20

<210> SEQ ID NO 99
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 99

Glu Pro Arg Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 100
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 100

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 101
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 101

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly
225                 230

<210> SEQ ID NO 102
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 102

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Gln Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 103
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 103

Glu Pro Arg Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro

```
            20                  25                  30
Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 104
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 104

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
```

```
                145                 150                 155                 160
Trp Glu Ser Asn Gly Gln Pro Glu Asn Tyr Lys Thr Thr Pro Pro
                    165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 105
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 105

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 106
<211> LENGTH: 232
<212> TYPE: PRT
<213> ORGANISM: Artificial Sequence
<220> FEATURE:
<223> OTHER INFORMATION: Synthetic polypeptide
```

<400> SEQUENCE: 106

```
Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 107
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 107

```
Glu Pro Lys Ser Ser Asp Lys Thr His Thr Ser Pro Pro Ser Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

Leu Pro Ser Ser Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 108
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 108

Glu Pro Lys Ser Ser Asp Lys Thr His Thr Ser Pro Pro Ser Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Gly
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 109
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 109

Glu Pro Lys Ser Ser Asp Lys Thr His Thr Ser Pro Pro Ser Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Gly
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 110
<211> LENGTH: 229
<212> TYPE: PRT
<213> ORGANISM: Artificial Sequence
<220> FEATURE:
<223> OTHER INFORMATION: Synthetic polypeptide

<400> SEQUENCE: 110

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Lys Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

```
Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 111
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 111

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Gln Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Arg Leu Thr Val Asp Lys Ser Arg Trp Gln Glu Gly Asn Val Phe
        195                 200                 205
```

Ser Cys Ser Val Met His Glu Ala Leu His Asn His Tyr Thr Gln Lys
    210                 215                 220

Ser Leu Ser Leu Ser Leu Gly Lys
225                 230

<210> SEQ ID NO 112
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 112

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Ala Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 113
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 113

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val

```
                    35                  40                  45
Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn Ala Tyr Thr Gln Lys
    210                 215                 220

Ser Leu Ser Leu Ser Pro Gly Lys
225                 230

<210> SEQ ID NO 114
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 114

Glu Pro Lys Ser Ser Asp Lys Thr His Thr Cys Pro Pro Cys Pro Ala
 1               5                  10                  15

Pro Glu Ala Glu Gly Ala Pro Ser Val Phe Leu Phe Pro Pro Lys Pro
                 20                  25                  30

Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Gln Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ser Ser Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
```

```
                165                 170                 175
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 115
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 115

Glu Pro Lys Ser Ser Asp Lys Thr His Thr Ser Pro Pro Ser Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Ala Leu Gly
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 116
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 116
```

```
Glu Pro Lys Ser Ser Asp Lys Thr His Thr Ser Pro Ser Pro Ala
1               5                   10                  15

Pro Glu Leu Leu Gly Gly Pro Ser Val Phe Leu Phe Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Ala Leu Gly
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 117
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 117

Glu Pro Lys Ser Ser Asp Lys Thr His Thr Cys Pro Pro Cys Pro Ala
1               5                   10                  15

Pro Glu Ala Gly Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Ser Ile Glu Lys Thr Ile Ser Lys Ala Lys Gly Gln Pro
            115                 120                 125
```

```
Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly Lys
225                 230
```

<210> SEQ ID NO 118
<211> LENGTH: 233
<212> TYPE: PRT
<213> ORGANISM: Mus sp.

<400> SEQUENCE: 118

```
Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
                20                  25                  30

Ile Lys Asp Val Leu Met Ile Ser Leu Ser Pro Ile Val Thr Cys Val
                35                  40                  45

Val Val Asp Val Ser Glu Asp Asp Pro Asp Val Gln Ile Ser Trp Phe
50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
                100                 105                 110

Asp Leu Pro Ala Pro Ile Glu Arg Thr Ile Ser Lys Pro Lys Gly Ser
            115                 120                 125

Val Arg Ala Pro Gln Val Tyr Val Leu Pro Pro Glu Glu Glu Met
    130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
                180                 185                 190

Tyr Ser Lys Leu Arg Val Glu Lys Lys Asn Trp Val Glu Arg Asn Ser
            195                 200                 205

Tyr Ser Cys Ser Val Val His Glu Gly Leu His Asn His His Thr Thr
210                 215                 220

Lys Ser Phe Ser Arg Thr Pro Gly Lys
225                 230
```

<210> SEQ ID NO 119
<211> LENGTH: 238
<212> TYPE: PRT
<213> ORGANISM: Mus sp.

<400> SEQUENCE: 119

```
Glu Pro Arg Val Pro Ile Thr Gln Asn Pro Cys Pro Pro Leu Lys Glu
1               5                   10                  15

Cys Pro Pro Cys Ala Ala Pro Asp Leu Leu Gly Gly Pro Ser Val Phe
            20                  25                  30

Ile Phe Pro Pro Lys Ile Lys Asp Val Leu Met Ile Ser Leu Ser Pro
        35                  40                  45

Met Val Thr Cys Val Val Val Asp Val Ser Glu Asp Asp Pro Asp Val
50                  55                  60

Gln Ile Ser Trp Phe Val Asn Asn Val Glu Val His Thr Ala Gln Thr
65                  70                  75                  80

Gln Thr His Arg Glu Asp Tyr Asn Ser Thr Leu Arg Val Val Ser Ala
                85                  90                  95

Leu Pro Ile Gln His Gln Asp Trp Met Ser Gly Lys Glu Phe Lys Cys
            100                 105                 110

Lys Val Asn Asn Arg Ala Leu Pro Ser Pro Ile Glu Lys Thr Ile Ser
        115                 120                 125

Lys Pro Arg Gly Pro Val Arg Ala Pro Gln Val Tyr Val Leu Pro Pro
130                 135                 140

Pro Ala Glu Glu Met Thr Lys Lys Glu Phe Ser Leu Thr Cys Met Ile
145                 150                 155                 160

Thr Gly Phe Leu Pro Ala Glu Ile Ala Val Asp Trp Thr Ser Asn Gly
                165                 170                 175

Arg Thr Glu Gln Asn Tyr Lys Asn Thr Ala Thr Val Leu Asp Ser Asp
            180                 185                 190

Gly Ser Tyr Phe Met Tyr Ser Lys Leu Arg Val Gln Lys Ser Thr Trp
        195                 200                 205

Glu Arg Gly Ser Leu Phe Ala Cys Ser Val Val His Glu Gly Leu His
210                 215                 220

Asn His Leu Thr Thr Lys Thr Ile Ser Arg Ser Leu Gly Lys
225                 230                 235
```

<210> SEQ ID NO 120
<211> LENGTH: 233
<212> TYPE: PRT
<213> ORGANISM: Artificial Sequence
<220> FEATURE:
<223> OTHER INFORMATION: Synthetic polypeptide

<400> SEQUENCE: 120

```
Glu Pro Arg Ser Pro Thr Ile Lys Pro Cys Pro Pro Cys Lys Cys Pro
1               5                   10                  15

Ala Pro Asn Leu Glu Gly Gly Pro Ser Val Phe Ile Phe Pro Pro Lys
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Ala Phe Ala Cys Ala Val Asn Asn Lys
            100                 105                 110
```

```
Asp Leu Pro Ala Pro Ile Glu Arg Thr Ile Ser Lys Pro Lys Gly Ser
            115                 120                 125

Val Arg Ala Pro Gln Val Tyr Val Leu Pro Pro Glu Glu Glu Met
130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230

<210> SEQ ID NO 121
<211> LENGTH: 238
<212> TYPE: PRT
<213> ORGANISM: Artificial Sequence
<220> FEATURE:
<223> OTHER INFORMATION: Synthetic polypeptide

<400> SEQUENCE: 121

Glu Pro Arg Ser Pro Ile Thr Gln Asn Pro Cys Pro Pro Leu Lys Glu
1               5                   10                  15

Cys Pro Pro Cys Ala Ala Pro Asp Leu Glu Gly Gly Pro Ser Val Phe
                20                  25                  30

Ile Phe Pro Pro Lys Ile Lys Asp Val Leu Met Ile Ser Leu Ser Pro
            35                  40                  45

Met Val Thr Cys Val Val Val Asp Val Ser Glu Asp Asp Pro Asp Val
50                  55                  60

Gln Ile Ser Trp Phe Val Asn Asn Val Glu Val His Thr Ala Gln Thr
65                  70                  75                  80

Gln Thr His Arg Glu Asp Tyr Asn Ser Thr Leu Arg Val Val Ser Ala
                85                  90                  95

Leu Pro Ile Gln His Gln Asp Trp Met Ser Gly Lys Ala Phe Ala Cys
            100                 105                 110

Ala Val Asn Asn Arg Ala Leu Pro Ser Pro Ile Glu Lys Thr Ile Ser
        115                 120                 125

Lys Pro Arg Gly Pro Val Arg Ala Pro Gln Val Tyr Val Leu Pro Pro
130                 135                 140

Pro Ala Glu Glu Met Thr Lys Lys Glu Phe Ser Leu Thr Cys Met Ile
145                 150                 155                 160

Thr Gly Phe Leu Pro Ala Glu Ile Ala Val Asp Trp Thr Ser Asn Gly
                165                 170                 175

Arg Thr Glu Gln Asn Tyr Lys Asn Thr Ala Thr Val Leu Asp Ser Asp
            180                 185                 190

Gly Ser Tyr Phe Met Tyr Ser Lys Leu Arg Val Gln Lys Ser Thr Trp
        195                 200                 205

Glu Arg Gly Ser Leu Phe Ala Cys Ser Val Val His Glu Gly Leu His
    210                 215                 220

Asn His Leu Thr Thr Lys Thr Ile Ser Arg Ser Leu Gly Lys
225                 230                 235
```

<210> SEQ ID NO 122
<211> LENGTH: 329
<212> TYPE: PRT
<213> ORGANISM: Artificial Sequence
<220> FEATURE:
<223> OTHER INFORMATION: Synthetic polypeptide

<400> SEQUENCE: 122

```
Gly Val Ser Asp Val Pro Arg Asp Leu Glu Val Val Ala Ala Thr Pro
1               5                   10                  15

Thr Ser Leu Leu Ile Ser Trp Arg Pro Pro Ile His Ala Tyr Gly Tyr
            20                  25                  30

Tyr Arg Ile Thr Tyr Gly Glu Thr Gly Gly Asn Ser Pro Val Gln Glu
        35                  40                  45

Phe Thr Val Pro Ile Val Glu Gly Thr Ala Thr Ile Ser Gly Leu Lys
    50                  55                  60

Pro Gly Val Asp Tyr Thr Ile Thr Val Tyr Ala Val Glu Tyr Thr Phe
65                  70                  75                  80

Lys His Ser Gly Tyr Tyr His Arg Pro Ile Ser Ile Asn Tyr Arg Thr
                85                  90                  95

Glu Ile Glu Pro Lys Ser Ser Gly Ser Thr His Thr Cys Pro Pro Cys
            100                 105                 110

Pro Ala Pro Glu Leu Leu Gly Gly Ser Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 123
<211> LENGTH: 336
<212> TYPE: PRT
<213> ORGANISM: Artificial Sequence
<220> FEATURE:

<223> OTHER INFORMATION: Synthetic polypeptide

<400> SEQUENCE: 123

Glu Pro Lys Ser Ser Gly Ser Thr His Thr Cys Pro Pro Cys Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Ala Gly Gly Gly Ser Gly Gly Val
225                 230                 235                 240

Ser Asp Val Pro Arg Asp Leu Glu Val Val Ala Ala Thr Pro Thr Ser
                245                 250                 255

Leu Leu Ile Ser Trp Arg Pro Pro Ile His Ala Tyr Gly Tyr Tyr Arg
            260                 265                 270

Ile Thr Tyr Gly Glu Thr Gly Gly Asn Ser Pro Val Gln Glu Phe Thr
        275                 280                 285

Val Pro Ile Val Glu Gly Thr Ala Thr Ile Ser Gly Leu Lys Pro Gly
290                 295                 300

Val Asp Tyr Thr Ile Thr Val Tyr Ala Val Glu Tyr Thr Phe Lys His
305                 310                 315                 320

Ser Gly Tyr Tyr His Arg Pro Ile Ser Ile Asn Tyr Arg Thr Glu Ile
                325                 330                 335

<210> SEQ ID NO 124
<211> LENGTH: 329
<212> TYPE: PRT
<213> ORGANISM: Artificial Sequence
<220> FEATURE:
<223> OTHER INFORMATION: Synthetic polypeptide

<400> SEQUENCE: 124

Gly Val Ser Asp Val Pro Arg Asp Leu Glu Val Val Ala Ala Thr Pro
1               5                   10                  15

```
Thr Ser Leu Leu Ile Ser Trp Ser Pro Ala Asn Gly Tyr Gly Tyr
            20                  25                  30

Tyr Arg Ile Thr Tyr Gly Glu Thr Gly Asn Ser Pro Val Gln Glu
        35                  40                  45

Phe Thr Val Pro Val Gly Arg Gly Thr Ala Thr Ile Ser Gly Leu Lys
 50                  55                  60

Pro Gly Val Asp Tyr Thr Ile Thr Val Tyr Ala Val Glu Tyr Thr Tyr
 65                  70                  75                  80

Lys Gly Ser Gly Tyr Tyr His Arg Pro Ile Ser Ile Asn Tyr Arg Thr
                 85                  90                  95

Glu Ile Glu Pro Lys Ser Ser Gly Ser Thr His Thr Cys Pro Pro Cys
            100                 105                 110

Pro Ala Pro Glu Leu Leu Gly Gly Ser Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 125
<211> LENGTH: 336
<212> TYPE: PRT
<213> ORGANISM: Artificial Sequence
<220> FEATURE:
<223> OTHER INFORMATION: Synthetic polypeptide

<400> SEQUENCE: 125

Glu Pro Lys Ser Ser Gly Ser Thr His Thr Cys Pro Pro Cys Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
        35                  40                  45
```

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala Gly Gly Gly Ser Gly Gly Val
225                 230                 235                 240

Ser Asp Val Pro Arg Asp Leu Glu Val Val Ala Ala Thr Pro Thr Ser
                245                 250                 255

Leu Leu Ile Ser Trp Ser Pro Pro Ala Asn Gly Tyr Gly Tyr Tyr Arg
            260                 265                 270

Ile Thr Tyr Gly Glu Thr Gly Gly Asn Ser Pro Val Gln Glu Phe Thr
        275                 280                 285

Val Pro Val Gly Arg Gly Thr Ala Thr Ile Ser Gly Leu Lys Pro Gly
    290                 295                 300

Val Asp Tyr Thr Ile Thr Val Tyr Ala Val Glu Tyr Tyr Lys Gly
305                 310                 315                 320

Ser Gly Tyr Tyr His Arg Pro Ile Ser Ile Asn Tyr Arg Thr Glu Ile
                325                 330                 335

<210> SEQ ID NO 126
<211> LENGTH: 329
<212> TYPE: PRT
<213> ORGANISM: Artificial Sequence
<220> FEATURE:
<223> OTHER INFORMATION: Synthetic polypeptide

<400> SEQUENCE: 126

Gly Val Ser Asp Val Pro Arg Asp Leu Glu Val Val Ala Ala Thr Pro
1               5                   10                  15

Thr Ser Leu Leu Ile Ser Trp Gly His Tyr Pro Leu His Val Arg Tyr
            20                  25                  30

Tyr Arg Ile Thr Tyr Gly Glu Thr Gly Gly Asn Ser Pro Val Gln Glu
        35                  40                  45

Phe Thr Val Pro Pro Arg Ser His Thr Ala Thr Ile Ser Gly Leu Lys
    50                  55                  60

Pro Gly Val Asp Tyr Thr Ile Thr Val Tyr Ala Val Thr Tyr Tyr Ala
65                  70                  75                  80

Gln Glu Asn Tyr Lys Glu Ile Pro Ile Ser Ile Asn Tyr Arg Thr Glu
            85                  90                  95

Ile Glu Pro Lys Ser Ser Gly Ser Thr His Thr Cys Pro Cys Pro
            100                 105                 110

Ala Pro Glu Leu Leu Gly Gly Ser Ser Val Phe Leu Phe Pro Pro Lys
            115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
            165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
            195                 200                 205

Ala Leu Pro Ala Pro Ile Glu Lys Thr Ile Ser Lys Ala Lys Gly Gln
            210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
            290                 295                 300

Phe Ser Cys Ser Val Met His Glu Ala Leu His Asn His Tyr Thr Gln
305                 310                 315                 320

Lys Ser Leu Ser Leu Ser Pro Gly Lys
            325

<210> SEQ ID NO 127
<211> LENGTH: 336
<212> TYPE: PRT
<213> ORGANISM: Artificial Sequence
<220> FEATURE:
<223> OTHER INFORMATION: Synthetic polypeptide

<400> SEQUENCE: 127

Glu Pro Lys Ser Ser Gly Ser Thr His Thr Cys Pro Pro Cys Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

```
Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala Gly Gly Gly Ser Gly Gly Val
225                 230                 235                 240

Ser Asp Val Pro Arg Asp Leu Glu Val Val Ala Ala Thr Pro Thr Ser
                245                 250                 255

Leu Leu Ile Ser Trp Gly His Tyr Pro Leu His Val Arg Tyr Tyr Arg
            260                 265                 270

Ile Thr Tyr Gly Glu Thr Gly Gly Asn Ser Pro Val Gln Glu Phe Thr
        275                 280                 285

Val Pro Pro Arg Ser His Thr Ala Thr Ile Ser Gly Leu Lys Pro Gly
    290                 295                 300

Val Asp Tyr Thr Ile Thr Val Tyr Ala Val Thr Tyr Tyr Ala Gln Glu
305                 310                 315                 320

Asn Tyr Lys Glu Ile Pro Ile Ser Ile Asn Tyr Arg Thr Glu Ala Ser
                325                 330                 335

<210> SEQ ID NO 128
<211> LENGTH: 330
<212> TYPE: PRT
<213> ORGANISM: Artificial Sequence
<220> FEATURE:
<223> OTHER INFORMATION: Synthetic polypeptide

<400> SEQUENCE: 128

Gly Ser Val Ser Asp Val Pro Arg Asp Leu Glu Val Val Ala Ala Thr
1               5                   10                  15

Pro Thr Ser Leu Leu Ile Ser Trp Arg His Pro His Phe Pro Thr Arg
            20                  25                  30

Tyr Tyr Arg Ile Thr Tyr Gly Glu Thr Gly Gly Asn Ser Pro Val Gln
        35                  40                  45

Glu Phe Thr Val Pro Leu Gln Pro Pro Thr Ala Thr Ile Ser Gly Leu
    50                  55                  60

Lys Pro Gly Val Asp Tyr Thr Ile Thr Val Tyr Ala Val Thr Asp Gly
65                  70                  75                  80

Arg Asn Gly Arg Leu Leu Ser Ile Pro Ile Ser Ile Asn Tyr Arg Thr
                85                  90                  95

Glu Ile Glu Pro Lys Ser Ser Asp Lys Thr His Thr Cys Pro Pro Cys
            100                 105                 110

Pro Ala Pro Glu Leu Leu Gly Gly Ser Ser Val Phe Leu Phe Pro Pro
        115                 120                 125

Lys Pro Lys Asp Thr Leu Met Ile Ser Arg Thr Pro Glu Val Thr Cys
    130                 135                 140
```

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 129
<211> LENGTH: 330
<212> TYPE: PRT
<213> ORGANISM: Artificial Sequence
<220> FEATURE:
<223> OTHER INFORMATION: Synthetic polypeptide

<400> SEQUENCE: 129

Gly Ser Val Ser Asp Val Pro Arg Asp Leu Glu Val Val Ala Ala Thr
1               5                   10                  15

Pro Thr Ser Leu Leu Ile Ser Trp Arg His Pro His Phe Pro Thr Arg
            20                  25                  30

Tyr Tyr Arg Ile Thr Tyr Gly Glu Thr Gly Gly Asn Ser Pro Val Gln
        35                  40                  45

Glu Phe Thr Val Pro Leu Gln Pro Pro Thr Ala Thr Ile Ser Gly Leu
    50                  55                  60

Lys Pro Gly Val Asp Tyr Thr Ile Thr Val Tyr Ala Val Thr Asp Gly
65                  70                  75                  80

Arg Asn Gly Arg Leu Leu Ser Ile Pro Ile Ser Ile Asn Tyr Arg Thr
            85                  90                  95

Glu Ile Glu Pro Lys Ser Ser Asp Lys Thr His Thr Cys Pro Pro Cys
        100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 130
<211> LENGTH: 5
<212> TYPE: PRT
<213> ORGANISM: Artificial Sequence
<220> FEATURE:
<223> OTHER INFORMATION: Synthetic peptide

<400> SEQUENCE: 130

Gly Gly Gly Gly Ser
1               5

<210> SEQ ID NO 131
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: /replace=" "
<220> FEATURE:
<221> NAME/KEY: misc_feature
<222> LOCATION: (1)..(2)
<223> OTHER INFORMATION: /note="Residues given in the sequence have no
      preference with respect to those in the annotations for said
      positions"
<220> FEATURE:
<221> NAME/KEY: VARIANT
<222> LOCATION: (2)..(2)
<223> OTHER INFORMATION: /replace=" "
<220> FEATURE:
<221> NAME/KEY: misc_feature
<222> LOCATION: (3)..(22)
<223> OTHER INFORMATION: /note="This region may encompass 2 to 10
      'Glu Asp' repeating units"

<400> SEQUENCE: 131

Glu Ile Glu Asp Glu Asp Glu Asp Glu Asp Glu Asp Glu Asp Glu Asp
1               5                   10                  15

Glu Asp Glu Asp Glu Asp
            20
```

<210> SEQ ID NO 132
<211> LENGTH: 7
<212> TYPE: PRT
<213> ORGANISM: Artificial Sequence
<220> FEATURE:
<223> OTHER INFORMATION: Synthetic peptide

<400> SEQUENCE: 132

Glu Leu Gln Leu Glu Glu Ser
1               5

<210> SEQ ID NO 133
<211> LENGTH: 21
<212> TYPE: PRT
<213> ORGANISM: Artificial Sequence
<220> FEATURE:
<223> OTHER INFORMATION: Synthetic peptide

<400> SEQUENCE: 133

Gln Lys Ser Leu Ser Leu Ser Pro Gln Pro Asp Glu Pro Gly Val Ser
1               5                   10                  15

Asp Val Pro Arg Asp
            20

<210> SEQ ID NO 134
<211> LENGTH: 23
<212> TYPE: PRT
<213> ORGANISM: Artificial Sequence
<220> FEATURE:
<223> OTHER INFORMATION: Synthetic peptide

<400> SEQUENCE: 134

Gln Lys Ser Leu Ser Leu Ser Pro Ala Gly Gly Gly Ser Gly Gly
1               5                   10                  15

Val Ser Asp Val Pro Arg Asp
            20

<210> SEQ ID NO 135
<211> LENGTH: 23
<212> TYPE: PRT
<213> ORGANISM: Artificial Sequence
<220> FEATURE:
<223> OTHER INFORMATION: Synthetic peptide

<400> SEQUENCE: 135

Gln Lys Ser Leu Ser Leu Ser Pro Pro Val Pro Pro Pro Pro Gly
1               5                   10                  15

Val Ser Asp Val Pro Arg Asp
            20

<210> SEQ ID NO 136
<211> LENGTH: 27
<212> TYPE: PRT
<213> ORGANISM: Artificial Sequence
<220> FEATURE:
<223> OTHER INFORMATION: Synthetic peptide

<400> SEQUENCE: 136

Gln Lys Ser Leu Ser Leu Ser Pro Glu Asp Glu Asp Glu Asp Glu Asp
1               5                   10                  15

Glu Asp Glu Gly Val Ser Asp Val Pro Arg Asp
            20                  25

<210> SEQ ID NO 137

```
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 137

Gln Lys Ser Leu Ser Leu Ser Pro Asp Leu Pro Gln Glu Thr Leu Glu
1               5                   10                  15

Glu Glu Thr Pro Gly Ala Gly Val Ser Asp Val Pro Arg Asp
            20                  25                  30

<210> SEQ ID NO 138
<211> LENGTH: 28
<212> TYPE: PRT
<213> ORGANISM: Artificial Sequence
<220> FEATURE:
<223> OTHER INFORMATION: Synthetic peptide

<400> SEQUENCE: 138

Gln Lys Ser Leu Ser Leu Ser Pro Val Pro Ser Thr Pro Pro Thr Pro
1               5                   10                  15

Ser Pro Ser Thr Gly Val Ser Asp Val Pro Arg Asp
            20                  25

<210> SEQ ID NO 139
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 139

Gln Lys Ser Leu Ser Leu Ser Pro Glu Leu Gln Leu Glu Glu Ser Ala
1               5                   10                  15

Ala Glu Ala Gln Glu Gly Glu Leu Glu Gly Val Ser Asp Val Pro Arg
            20                  25                  30

Asp

<210> SEQ ID NO 140
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 140

Gln Lys Ser Leu Ser Leu Ser Pro Glu Ser Pro Lys Ala Gln Ala Ser
1               5                   10                  15

Ser Val Pro Thr Ala Gln Pro Gln Ala Glu Gly Val Ser Asp Val Pro
            20                  25                  30

Arg Asp

<210> SEQ ID NO 141
<211> LENGTH: 22
<212> TYPE: PRT
<213> ORGANISM: Artificial Sequence
<220> FEATURE:
<223> OTHER INFORMATION: Synthetic peptide

<400> SEQUENCE: 141

Gln Lys Ser Leu Ser Leu Ser Pro Pro Ala Val Pro Pro Pro Gly Val
1               5                   10                  15
```

Ser Asp Val Pro Arg Asp
            20

<210> SEQ ID NO 142
<211> LENGTH: 23
<212> TYPE: PRT
<213> ORGANISM: Artificial Sequence
<220> FEATURE:
<223> OTHER INFORMATION: Synthetic peptide

<400> SEQUENCE: 142

Gln Lys Ser Leu Ser Leu Ser Pro Glu Leu Gln Leu Glu Glu Ser Gly
1               5                   10                  15

Val Ser Asp Val Pro Arg Asp
            20

<210> SEQ ID NO 143
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 143

Gln Lys Ser Leu Ser Leu Ser Pro Glu Leu Gln Leu Glu Glu Ser Ala
1               5                   10                  15

Ala Glu Ala Gln Glu Gly Glu Leu Glu Gly Val Ser Asp Val Pro Arg
            20                  25                  30

Asp

<210> SEQ ID NO 144
<211> LENGTH: 29
<212> TYPE: PRT
<213> ORGANISM: Artificial Sequence
<220> FEATURE:
<223> OTHER INFORMATION: Synthetic peptide

<400> SEQUENCE: 144

Gln Lys Ser Leu Ser Leu Ser Pro Val Pro Ser Thr Pro Pro Thr Pro
1               5                   10                  15

Ser Pro Ser Thr Gly Gly Val Ser Asp Val Pro Arg Asp
            20                  25

<210> SEQ ID NO 145
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 145

Gln Lys Ser Leu Ser Leu Ser Pro Val Pro Ser Thr Pro Pro Thr Pro
1               5                   10                  15

Ser Pro Ser Thr Pro Pro Thr Pro Ser Pro Ser Gly Gly Val Ser Asp
            20                  25                  30

Val Pro Arg Asp
        35

<210> SEQ ID NO 146
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 146

Gln Lys Ser Leu Ser Leu Ser Pro Gly Arg Gly Gly Glu Glu Lys Lys
1               5                   10                  15

Lys Glu Lys Glu Lys Glu Glu Gly Gly Val Ser Asp Val Pro Arg Asp
            20                  25                  30

<210> SEQ ID NO 147
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 147

Gln Lys Ser Leu Ser Leu Ser Pro Gly Arg Gly Gly Glu Glu Lys Lys
1               5                   10                  15

Lys Glu Lys Glu Lys Glu Glu Gln Glu Glu Arg Glu Thr Lys Thr Pro
            20                  25                  30

Gly Gly Val Ser Asp Val Pro Arg Asp
        35                  40

<210> SEQ ID NO 148
<211> LENGTH: 26
<212> TYPE: PRT
<213> ORGANISM: Artificial Sequence
<220> FEATURE:
<223> OTHER INFORMATION: Synthetic peptide

<400> SEQUENCE: 148

Gln Lys Ser Leu Ser Leu Ser Pro Glu Ser Pro Lys Ala Gln Ala Ser
1               5                   10                  15

Ser Gly Gly Val Ser Asp Val Pro Arg Asp
            20                  25

<210> SEQ ID NO 149
<211> LENGTH: 35
<212> TYPE: PRT
<213> ORGANISM: Artificial Sequence
<220> FEATURE:
<223> OTHER INFORMATION: Synthetic polypeptide

<400> SEQUENCE: 149

Gln Lys Ser Leu Ser Leu Ser Pro Glu Ser Pro Lys Ala Gln Ala Ser
1               5                   10                  15

Ser Val Pro Thr Ala Gln Pro Gln Ala Glu Gly Gly Val Ser Asp Val
            20                  25                  30

Pro Arg Asp
        35

<210> SEQ ID NO 150
<211> LENGTH: 39
<212> TYPE: PRT
<213> ORGANISM: Artificial Sequence
<220> FEATURE:
<223> OTHER INFORMATION: Synthetic polypeptide

<400> SEQUENCE: 150

Gln Lys Ser Leu Ser Leu Ser Pro Ser Val Glu Glu Lys Lys Lys Glu
1               5                   10                  15

Lys Glu Lys Glu Glu Gln Glu Glu Arg Glu Thr Lys Thr Pro Gly Gly
            20                  25                  30

Val Ser Asp Val Pro Arg Asp
            35

<210> SEQ ID NO 151
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 151

Gln Lys Ser Leu Ser Leu Ser Pro Pro Ser Val Glu Glu Lys Lys Lys
1               5                   10                  15

Glu Lys Glu Lys Glu Glu Gln Glu Glu Arg Glu Thr Lys Thr Pro Gly
            20                  25                  30

Gly Val Ser Asp Val Pro Arg Asp
            35                  40

<210> SEQ ID NO 152
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 152

Gln Lys Ser Leu Ser Leu Ser Pro Gly Ser Val Glu Glu Lys Lys Lys
1               5                   10                  15

Glu Lys Glu Lys Glu Glu Gln Glu Glu Arg Glu Thr Lys Thr Pro Gly
            20                  25                  30

Gly Val Ser Asp Val Pro Arg Asp
            35                  40

<210> SEQ ID NO 153
<211> LENGTH: 6
<212> TYPE: PRT
<213> ORGANISM: Artificial Sequence
<220> FEATURE:
<223> OTHER INFORMATION: Synthetic peptide:  6xHis tag

<400> SEQUENCE: 153

His His His His His His
1               5

<210> SEQ ID NO 154
<211> LENGTH: 232
<212> TYPE: PRT
<213> ORGANISM: Homo sapiens

<400> SEQUENCE: 154

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

```
Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 155
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 155

Glu Pro Arg Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Cys Lys
            20                  25                  30

Val Ser Asn Lys Ala Leu Pro Ser Ser Ile Glu Lys Thr
        35                  40                  45

<210> SEQ ID NO 156
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 156

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Cys Lys
            20                  25                  30

Val Ser Asn Lys Ala Leu Pro Ser Ser Ile Glu Lys Thr
        35                  40                  45

<210> SEQ ID NO 157
<211> LENGTH: 51
<212> TYPE: PRT
<213> ORGANISM: Artificial Sequence
<220> FEATURE:
<223> OTHER INFORMATION: Synthetic polypeptide

<400> SEQUENCE: 157

Glu Pro Lys Ser Ser Asp Lys Thr His Thr Cys Pro Pro Cys Pro Ala
1               5                   10                  15
```

```
Pro Glu Ala Glu Gly Ala Pro Ser Val Phe Leu Phe Pro Pro Cys Lys
            20                  25                  30

Val Ser Asn Lys Ala Leu Pro Ser Ser Ile Glu Lys Thr Leu Ser Leu
        35                  40                  45

Ser Pro Gly
    50

<210> SEQ ID NO 158
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 158

Glu Pro Lys Ser Cys Asp Lys Thr His Thr Cys Pro Pro Cys Pro Pro
1               5                   10                  15

Arg Glu Glu Gln Tyr Gln Ser Thr Tyr Arg Val Val Ser Val
            20                  25                  30

<210> SEQ ID NO 159
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 159

Glu Pro Arg Ser Ser Asp Lys Thr His Thr Cys Pro Pro Cys Pro
1               5                   10                  15

<210> SEQ ID NO 160
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 160

Asp Lys Thr His Thr Cys Pro Pro Cys Pro
1               5                   10

<210> SEQ ID NO 161
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 161

Glu Pro Lys Ser Ser Asp Lys Thr His Thr Cys Pro Pro Cys Pro
1               5                   10                  15

<210> SEQ ID NO 162
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 162

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro
            20                  25                  30
```

<210> SEQ ID NO 163
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 163

Glu Pro Lys Ser Ser Asp Lys Thr His Thr Ser Pro Pro Ser Pro Ala
1               5                   10                  15

Pro Glu Ala Glu Gly Ala Pro Ser Val Phe Leu Phe Pro Pro Cys Lys
            20                  25                  30

Val Ser Asn Lys Ala Leu Pro Ser Ser Ile Glu Lys Thr
        35                  40                  45

<210> SEQ ID NO 164
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 164

Glu Pro Lys Ser Ser Asp Lys Thr His Thr Ser Pro Pro Ser Pro Ala
1               5                   10                  15

Pro Glu Ala Glu Gly Ala Pro Ser Val Phe Leu Phe Pro Pro Cys Lys
            20                  25                  30

Val Ser Asn Lys Ala Leu Pro Ser Ser Ile Glu Lys Thr Pro Val Leu
        35                  40                  45

Asp Ser Asp Gly Ser Phe Phe Leu Gly Ser Lys Leu
    50                  55                  60

<210> SEQ ID NO 165
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 165

Glu Pro Lys Ser Ser Asp Lys Thr His Thr Ser Pro Pro Ser Pro Pro
1               5                   10                  15

Val Leu Asp Ser Asp Gly Ser Phe Phe Leu Gly Ser Lys Leu
            20                  25                  30

<210> SEQ ID NO 166
<211> LENGTH: 124
<212> TYPE: PRT
<213> ORGANISM: Artificial Sequence
<220> FEATURE:
<223> OTHER INFORMATION: Synthetic polypeptide

<400> SEQUENCE: 166

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Cys Val Val Val Asp
            20                  25                  30

Val Ser Gln Glu Asp Pro Glu Val Gln Phe Pro Arg Glu Glu Gln Phe
        35                  40                  45

Asn Ser Thr Tyr Arg Val Val Ser Val Cys Lys Val Ser Asn Lys Gly
    50                  55                  60

```
Leu Pro Ser Ser Ile Glu Lys Thr Leu Pro Ser Gln Glu Met
 65                  70                  75                  80

Thr Lys Asn Gln Val Ser Leu Pro Val Leu Asp Ser Asp Gly Ser Phe
                 85                  90                  95

Phe Leu Tyr Ser Arg Leu Thr Val Asp Lys Ser Arg Trp Gln Glu Gly
            100                 105                 110

Asn Val Phe Ser Cys Leu Ser Leu Ser Leu Gly Lys
        115                 120

<210> SEQ ID NO 167
<211> LENGTH: 67
<212> TYPE: PRT
<213> ORGANISM: Artificial Sequence
<220> FEATURE:
<223> OTHER INFORMATION: Synthetic polypeptide

<400> SEQUENCE: 167

Glu Pro Lys Ser Ser Asp Lys Thr His Thr Cys Pro Pro Cys Pro Leu
1               5                   10                  15

Pro Pro Ser Gln Glu Glu Met Thr Lys Asn Gln Val Ser Leu Pro Val
            20                  25                  30

Leu Asp Ser Asp Gly Ser Phe Phe Leu Tyr Ser Arg Leu Thr Val Asp
        35                  40                  45

Lys Ser Arg Trp Gln Gly Asn Val Phe Ser Cys Leu Ser Leu Ser
    50                  55                  60

Leu Gly Lys
65

<210> SEQ ID NO 168
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 168

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Ala Pro Pro
            20                  25                  30

<210> SEQ ID NO 169
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 169

Glu Pro Lys Ser Ser Asp Lys Thr His Thr Cys Pro Pro Cys Pro Ser
1               5                   10                  15

Val Met His Glu Ala Leu His Asn His Tyr Thr Gln Lys Ser
            20                  25                  30

<210> SEQ ID NO 170
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 170
```

-continued

Glu Pro Lys Ser Ser Asp Lys Thr His Thr Cys Pro Cys Pro Ala
1               5                   10                  15

Pro Glu Ala Glu Gly Ala Pro Ser Val Phe Leu Phe Pro Pro Arg
            20                  25                  30

Glu Glu Gln Tyr Gln Ser Thr Tyr Arg Val Val Ser Val Cys Lys Val
        35                  40                  45

Ser Asn Lys Ala Leu Pro Ser Ser Ile Glu Lys Thr
    50                  55                  60

<210> SEQ ID NO 171
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 171

Glu Pro Lys Ser Ser Asp Lys Thr His Thr Ser Pro Pro Ser Pro Ala
1               5                   10                  15

Pro Glu Ala Glu Gly Ala Pro Ser Val Phe Leu Phe Pro Pro Cys Lys
            20                  25                  30

Val Ser Asn Lys Ala Leu Pro Ser Ser Ile Glu Lys Thr Pro Val Leu
        35                  40                  45

Asp Ser Asp Gly Ser Phe Ala Leu Ala Ser Lys Leu
    50                  55                  60

<210> SEQ ID NO 172
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 172

Glu Pro Lys Ser Ser Asp Lys Thr His Thr Ser Pro Pro Ser Pro Pro
1               5                   10                  15

Val Leu Asp Ser Asp Gly Ser Phe Ala Leu Ala Ser Lys Leu
            20                  25                  30

<210> SEQ ID NO 173
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 173

Glu Pro Lys Ser Ser Asp Lys Thr His Thr Cys Pro Cys Pro Ala
1               5                   10                  15

Pro Glu Ala Glu Gly Gly Pro Ser Val Phe Leu Phe Pro Pro Cys Lys
            20                  25                  30

Val Ser Asn Lys Ala Leu Pro Ala Ser Ile Glu Lys Thr
        35                  40                  45

<210> SEQ ID NO 174
<211> LENGTH: 233
<212> TYPE: PRT
<213> ORGANISM: Mouse sp.
<220> FEATURE:
<221> NAME/KEY: misc_feature
<223> OTHER INFORMATION: wild type BALB/c mouse gamma - 2a constant
      region Fc

<400> SEQUENCE: 174

Glu Pro Arg Gly Pro Thr Ile Lys Pro Cys Pro Cys Lys Cys Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
            35                  40                  45

Val Val Asp Val Ser Glu Asp Asp Pro Asp Val Gln Ile Ser Trp Phe
50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
            115                 120                 125

Val Arg Ala Pro Gln Val Tyr Val Leu Pro Pro Pro Glu Glu Glu Met
130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
            195                 200                 205

Tyr Ser Cys Ser Val Val His Glu Gly Leu His Asn His His Thr Thr
            210                 215                 220

Lys Ser Phe Ser Arg Thr Pro Gly Lys
225                 230

<210> SEQ ID NO 175
<211> LENGTH: 233
<212> TYPE: PRT
<213> ORGANISM: Artificial Sequence
<220> FEATURE:
<223> OTHER INFORMATION: Synthetic polypeptide

<400> SEQUENCE: 175

Glu Pro Arg Ser Pro Thr Ile Lys Pro Cys Pro Pro Cys Lys Cys Pro
1               5                   10                  15

Ala Pro Asn Leu Glu Gly Gly Pro Ser Val Phe Ile Phe Pro Pro Lys
            20                  25                  30

Ile Lys Asp Val Leu Met Ile Ser Leu Ser Pro Ile Val Thr Cys Val
            35                  40                  45

Val Val Asp Val Ser Glu Asp Asp Pro Asp Val Gln Ile Ser Trp Phe
50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Ala Phe Ala Cys Ala Val Asn Asn Lys
            100                 105                 110

```
Asp Leu Pro Ala Pro Ile Glu Arg Thr Ile Ser Lys Pro Lys Gly Ser
            115                 120                 125

Val Arg Ala Pro Gln Val Tyr Val Leu Pro Pro Glu Glu Glu Met
130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
            195                 200                 205

Tyr Ser Cys Ser Val Val His Glu Gly Leu His Asn His His Thr Thr
            210                 215                 220

Lys Ser Phe Ser Arg Thr Pro Gly Lys
225                 230

<210> SEQ ID NO 176
<211> LENGTH: 238
<212> TYPE: PRT
<213> ORGANISM: Mouse sp.
<220> FEATURE:
<221> NAME/KEY: misc_feature
<223> OTHER INFORMATION: wild type C57BL/6 mouse gamma 2c constant
      region Fc

<400> SEQUENCE: 176

Glu Pro Arg Val Pro Ile Thr Gln Asn Pro Cys Pro Pro Leu Lys Glu
1               5                   10                  15

Cys Pro Pro Cys Ala Ala Pro Asp Leu Leu Gly Gly Pro Ser Val Phe
            20                  25                  30

Ile Phe Pro Pro Lys Ile Lys Asp Val Leu Met Ile Ser Leu Ser Pro
            35                  40                  45

Met Val Thr Cys Val Val Val Asp Val Ser Glu Asp Asp Pro Asp Val
        50                  55                  60

Gln Ile Ser Trp Phe Val Asn Asn Val Glu Val His Thr Ala Gln Thr
65                  70                  75                  80

Gln Thr His Arg Glu Asp Tyr Asn Ser Thr Leu Arg Val Val Ser Ala
                85                  90                  95

Leu Pro Ile Gln His Gln Asp Trp Met Ser Gly Lys Glu Phe Lys Cys
            100                 105                 110

Lys Val Asn Asn Arg Ala Leu Pro Ser Pro Ile Glu Lys Thr Ile Ser
            115                 120                 125

Lys Pro Arg Gly Pro Val Arg Ala Pro Gln Val Tyr Val Leu Pro Pro
130                 135                 140

Pro Ala Glu Glu Met Thr Lys Lys Glu Phe Ser Leu Thr Cys Met Ile
145                 150                 155                 160

Thr Gly Phe Leu Pro Ala Glu Ile Ala Val Asp Trp Trp Ser Asn Gly
                165                 170                 175

Arg Thr Glu Gln Asn Tyr Lys Asn Thr Ala Thr Val Leu Asp Ser Asp
            180                 185                 190

Gly Ser Tyr Phe Met Tyr Ser Lys Leu Arg Val Gln Lys Ser Thr Trp
            195                 200                 205

Glu Arg Gly Ser Leu Phe Ala Cys Ser Val Val His Glu Gly Leu His
            210                 215                 220

Asn His Leu Thr Thr Lys Thr Ile Ser Arg Ser Leu Gly Lys
```

<210> SEQ ID NO 177
<211> LENGTH: 238
<212> TYPE: PRT
<213> ORGANISM: Artificial Sequence
<220> FEATURE:
<223> OTHER INFORMATION: Synthetic polypeptide

<400> SEQUENCE: 177

```
Glu Pro Arg Ser Pro Ile Thr Gln Asn Pro Cys Pro Pro Leu Lys Glu
1               5                   10                  15
Cys Pro Pro Cys Ala Ala Pro Asp Leu Glu Gly Gly Pro Ser Val Phe
            20                  25                  30
Ile Phe Pro Pro Lys Ile Lys Asp Val Leu Met Ile Ser Leu Ser Pro
            35                  40                  45
Met Val Thr Cys Val Val Val Asp Val Ser Glu Asp Asp Pro Asp Val
        50                  55                  60
Gln Ile Ser Trp Phe Val Asn Asn Val Glu Val His Thr Ala Gln Thr
65                  70                  75                  80
Gln Thr His Arg Glu Asp Tyr Asn Ser Thr Leu Arg Val Val Ser Ala
                85                  90                  95
Leu Pro Ile Gln His Gln Asp Trp Met Ser Gly Lys Ala Phe Ala Cys
                100                 105                 110
Ala Val Asn Asn Arg Ala Leu Pro Ser Pro Ile Glu Lys Thr Ile Ser
                115                 120                 125
Lys Pro Arg Gly Pro Val Arg Ala Pro Gln Val Tyr Val Leu Pro Pro
    130                 135                 140
Pro Ala Glu Glu Met Thr Lys Lys Glu Phe Ser Leu Thr Cys Met Ile
145                 150                 155                 160
Thr Gly Phe Leu Pro Ala Glu Ile Ala Val Asp Trp Trp Ser Asn Gly
                165                 170                 175
Arg Thr Glu Gln Asn Tyr Lys Asn Thr Ala Thr Val Leu Asp Ser Asp
                180                 185                 190
Gly Ser Tyr Phe Met Tyr Ser Lys Leu Arg Val Gln Lys Ser Thr Trp
                195                 200                 205
Glu Arg Gly Ser Leu Phe Ala Cys Ser Val Val His Glu Gly Leu His
    210                 215                 220
Asn His Leu Thr Thr Lys Thr Ile Ser Arg Ser Leu Gly Lys
225                 230                 235
```